US009682967B2

(12) United States Patent
Maltas et al.

(10) Patent No.: US 9,682,967 B2
(45) Date of Patent: Jun. 20, 2017

(54) N-SUBSTITUTED-5-SUBSTITUTED PHTHALAMIC ACIDS AS SORTILIN INHIBITORS

(71) Applicant: H. Lundbeck A/S, Valby (DK)

(72) Inventors: Philip James Maltas, Valby (DK); Stephen Watson, Valby (DK); Morten Langgård, Glostrup (DK); Laurent David, Malmö (SE)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 14/763,544

(22) PCT Filed: Jan. 27, 2014

(86) PCT No.: PCT/EP2014/051481
§ 371 (c)(1),
(2) Date: Jul. 27, 2015

(87) PCT Pub. No.: WO2014/114779
PCT Pub. Date: Jul. 31, 2014

(65) Prior Publication Data
US 2015/0368231 A1 Dec. 24, 2015

Related U.S. Application Data

(60) Provisional application No. 61/875,158, filed on Sep. 9, 2013, provisional application No. 61/874,430, filed on Sep. 6, 2013, provisional application No. 61/776,876, filed on Mar. 12, 2013, provisional application No. 61/757,271, filed on Jan. 28, 2013.

(30) Foreign Application Priority Data

Jan. 28, 2013 (DK) .................................. 201300053
Mar. 11, 2013 (DK) .................................. 201300132
Sep. 6, 2013 (DK) .................................. 201300508

(51) Int. Cl.
C07D 409/04 (2006.01)
C07D 213/75 (2006.01)
C07D 215/38 (2006.01)
C07D 333/66 (2006.01)
C07D 401/04 (2006.01)
C07D 403/04 (2006.01)
C07D 237/20 (2006.01)
C07D 239/42 (2006.01)
(Continued)

(52) U.S. Cl.
CPC ............ C07D 409/04 (2013.01); A61K 31/44 (2013.01); A61K 31/4402 (2013.01); A61K 31/4406 (2013.01); C07D 213/40 (2013.01); C07D 213/60 (2013.01); C07D 213/65 (2013.01); C07D 213/75 (2013.01); C07D 215/38 (2013.01); C07D 237/20 (2013.01); C07D 239/42 (2013.01); C07D 241/20 (2013.01); C07D 277/46 (2013.01); C07D 333/66 (2013.01); C07D 333/68 (2013.01); C07D 401/04 (2013.01); C07D 403/04 (2013.01); C07D 417/04 (2013.01)

(58) Field of Classification Search
CPC .. C07D 409/04; C07D 213/40; C07D 213/60; C07D 213/65; C07D 213/75; C07D 215/38; C07D 237/20; C07D 239/42; C07D 241/20; C07D 277/46; C07D 333/68; C07D 333/66; C07D 401/04; C07D 403/04; C07D 417/04; A61K 31/44; A61K 31/4402; A61K 31/4406
See application file for complete search history.

(56) References Cited

U.S. PATENT DOCUMENTS

| 3,847,921 A | 11/1974 | Cotrel et al. |
| 4,086,348 A | 4/1978 | Cotrel et al. |
| 2009/0163545 A1* | 6/2009 | Goldfarb ............. A61K 31/122 514/312 |

FOREIGN PATENT DOCUMENTS

| EP | 1566378 A1 | 8/2005 |
| WO | 99/46267 A2 | 9/1999 |
| WO | 01/81345 A1 | 11/2001 |
| WO | 2006/007864 A1 | 1/2006 |
| WO | 2007/027780 A2 | 3/2007 |

OTHER PUBLICATIONS

X Collin et al., 1998, "Synthesis and Potent Tumour Necrosis Factor-[alpha] Production Inhibitor Activity of N-Pyridinylphthalimides and Derivatives", Pharmacy and Pharmacology Communications, vol. 4, pp. 27-31.

* cited by examiner

Primary Examiner — D M Seaman
(74) Attorney, Agent, or Firm — Jeffrey I. Auerbach; AuerbachSchrot LLC

(57) ABSTRACT

The present invention is directed to N-substituted-5-substituted phthalamic acids which of formula (A). The compounds are considered useful for the treatment of diseases treatment of a neurodegenerative disease, psychiatric disease, motorneuron disease, peripheral neuropathies, pain, neuroinflammation or atherosclerosis such as Alzheimer's disease and Parkinson's disease.

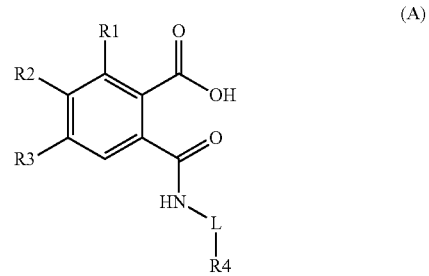

(A)

8 Claims, 2 Drawing Sheets

(51) Int. Cl.
*C07D 241/20* (2006.01)
*C07D 277/46* (2006.01)
*C07D 213/40* (2006.01)
*A61K 31/44* (2006.01)
*A61K 31/4402* (2006.01)
*A61K 31/4406* (2006.01)
*C07D 417/04* (2006.01)
*C07D 213/60* (2006.01)
*C07D 213/65* (2006.01)
*C07D 333/68* (2006.01)

N-SUBSTITUTED-5-SUBSTITUTED PHTHALAMIC ACIDS AS SORTILIN INHIBITORS

CROSS-REFERENCE TO RELATED APPLICATIONS

The present application is a §371 U.S. National Stage Application of PCT International Application No. PCT/EP2014/051481, filed Jan. 27, 2014, which claims benefit of priority under 35 U.S.C. §119(e) of U.S. Provisional Application No. 61/875,158, filed Sep. 9, 2013, U.S. Provisional Application No. 61/874,430, filed Sep. 6, 2013, U.S. Provisional Application No. 61/776,876, filed Mar. 12, 2013, and U.S. Provisional Application No. 61/757,271, filed Jan. 28, 2013 and which claims the benefit of priority under 35 U.S.C. §119(a)-(d) of Danish Application No. PA201300508, filed Sep. 6, 2013, Danish Application No. PA201300132, filed Mar. 11, 2013, and Danish Application No. PA201300053, filed Jan. 28, 2013. Each of these applications is hereby incorporated by reference in its entirety.

FIELD OF THE INVENTION

The present invention relates to certain N-substituted-5-substituted phthalamic acids which are inhibitors of the Sortilin receptor and thus useful in therapy and to pharmaceutical compositions comprising said compounds.

REFERENCE TO SEQUENCE LISTING

This application includes a Sequence Listing pursuant to 37 C.F.R. 1.821 et seq., which is disclosed in both paper and computer-readable media, and which paper and computer-readable disclosures are herein incorporated by reference in their entireties.

BACKGROUND OF THE INVENTION

Sortilin (also called NTR-3 or GP95) is a type I membrane receptor belonging to the Vps10p (vacuolar protein sorting 10 protein) domain family of sorting receptors (Winnow et al, Nat Rev Neurosci, 12:899-909 (2008)) which also comprises SorLA, SorCS1, SorCS2 and SorCS3. The Vps10p family shares the Vps10p extracellular domain of approximately 700 amino acids, originally identified as a sorting receptor in *Saccharomyces cerevisiae*, which in sortilin encompasses the entire extracellular part forming a so-called 10-bladed beta-propeller, the structure of which has been reported (Quistgaard et al, Nat Struct Mol Biol, 1:96-8 (2009)). Sortilin is widely expressed in the peripheral and central nervous system in neurons as well as in other tissues and cells including liver, heart, testis, uterus, kidney, skeletal muscle, T-cells, B-cells and NK cells (Petersen et al., J. Biol. Chem., 272:3599-3605 (1997); Herman-Borgmeyer et al., Mol. Brain Res., 65:216-219 (1999)). Herda et al, Immunity, 37(5):854-66 (2012)). Only a small fraction of the protein is expressed at the cell surface while an estimated 90% is localized intracellularly although the distribution for sortilin may be regulated by ligand interactions.

Sortilin has been shown to mediate pro-apoptotic effects of pro-neurotrophins, including pro-NGF, proNT3 and pro-BDNF which, through binding to a Sortilin-P75 complex, induce degeneration and cell death in cellular and animal models of a number of neurodegenerative disorders (Nykjaer et al, Nature, 427(6977):843-8 (2004)). In addition, sortilin mediates trafficking and sorting of neurotrophin receptors and also is a regulator of proBDNF secretion (Evans et al, J Biol Chem, 86(34):29556-67 (2011)). Thereby, sortilin is considered a key regulator of the balance between generally opposing effects of mature and pro-forms of neurotrophins Targeting sortilin-P75-mediated apoptosis has been suggested as a protective mechanism in neurodegenerative disorders based on studies in cellular and animal models related to acute and chronic neurodegenerative conditions. Specifically, sortilin has been suggested to have beneficial effects in pain as sortilin knockout mice were found to be protected in a spared nerve injury pain model (Nykjaer et al, WO 2009/155932 A2).

Several binding partners for sortilin have been identified in addition to pro-neurotrophins Sortilin has been shown to be a receptor for the neuropeptide neurotensin (Mazella et al, J Biol Chem., 273(41):26273-6 (1998)), and more recently also to function as a receptor for progranulin (PGRN) (Hu et al, Neuron, 68(4):654-67, (2010), Carrasquillo et al, Am J Hum Genet, 87(6):890-7 (2010)). The binding sites of neurotensin and progranulin have been characterized and shown to localize to the same amino acids (Hu et al, Neuron, 68(4):654-67, (2010), Quistgaard et al, Nat Struct Mol Biol, 1:96-8 (2009), Zheng et al, PLoS One. 2011; 6(6):e21023 (2011)) whereas the pro-neurotrophin binding site has been suggested to localize to a separate site from the neurotensin binding site (Senip Andersen et al, J Biol Chem. 285(16): 12210-22 (2010)) although pro-neurotrophin binding is inhibited by neurotensin in functional tests.

Recently, sortilin has been shown to mediate clearance of PGRN by binding followed by cellular uptake and distribution to lysosomes. PGRN has neurotrophic properties and has been linked to frontotemporal lobar degeneration (FTLD), a neurodegenerative disorder characterized by inclusions positive for the RNA binding protein TAR DNA-binding protein 43 (TDP-43). In a subset of FTLD patients, PGRN expression is decreased due to mutations in the GRN gene. In mice, sortilin knock out was reported to increase PGRN levels and sortilin deficiency in PGRN+/−mice was found to increase PGRN to at least WT level. Therefore, targeting of sortilin has been suggested to alleviate or normalize PGRN expression levels to halt or slow neurodegeneration in FTLD (Prudencio et al, Proc Natl Acad Sci USA. 109(52):21510-5 (2012)). A genome-wide screening associated an SNP near the SORT1 gene locus with PGRN expression levels and furthermore, a study of altered expression and splicing after reducing TDP-43 in mouse brain by means of antisense oligonucleotides identified sortilin as being among the several alternatively spliced genes supporting a role for sortilin in ALS and TSDP-43 pathology (Polymenidou et al, Nat Neurosci. 14(4):459-68 (2011), Carrasquillo et al, Am J Hum Genet.; 87(6):890-7 (2010)).

In addition to TDP-43-pathology, PGRN has been attributed to other functions, including in inflammation and tissue repair. PGRN has been reported to bind TNF receptors with high affinity (Tang et al, Science, 332(6028):478-84 (2011)) thereby modulating TNF-alpha binding and showing proinflammatory effect in mouse models of rheumatoid arthritis. Therefore, targeting of sortilin has been suggested to exert anti-inflammatory effects by inhibiting PGRN clearance (Nykjaer and Willnow, Trends Neurosci., 35(4):261-70 (2012))

Sortilin is expressed in immune cells and has been implicated in inflammatory disorders as loss of sortilin was recently reported to reduce IFN-gamma release from CTL and TH1 T-cells and NK cells. It was suggested that sortilin modulates the adaptive and innate immune responses by regulating IFN-gamma secretion and that sortilin may be a target (Herda et al, Immunity, 37(5):854-66 (2012)) in inflammatory bowel disease and other IFN-gamma-dependent inflammatory disorders.

A number of other binding partners for sortilin have been reported. The growth factor CNTF was shown to bind sortilin with high affinity and to be cleared by cellular uptake (Larsen et al, Mol Cell Biol. (17):4175-87 (2010)) whereby sortilin modulated signalling through the GP103/LIFRbeta receptor complex, presumably via a direct interaction with LIFRbeta. A similar effect was observed for the related cytokines CT-1, LIF, OSM, and IL-6. Sortilin therefore is suggested to facilitate LIFRbeta-dependent signalling such that modulation of sortilin may be of benefit in disorders in which CNTF and related cytokines are of importance. Also, sortilin has been reported to mediate internalization of the kappa opioid receptor (Liu-Chen, 2012, poster, Society for Neuroscience annual meeting, 2012) and a peptide, spadin, which is cleaved of from pro-sortilin has been reported to bind TREK-1 potassium channels (Mazella et al, PLoS Biol. 8(4): e1000355, (2010)).

In addition, Sortilin is a major constituent of glucose transporter 4-containing vesicles (Morris et al, J Biol Chem. 273(6):3582-7 (1998)) and is believed to be involved as a cargo adaptor protein in the formation of the intracellular insulin responsive vesicles from the trans-Golgi network (Bogan et al, Curr Opin Cell Biol. (4):506-12 (2010)). Intracellularly, sortilin interacts with Apolipoprotein B100 (apoB100, Kjolby et al, Cell Metab, 12(3):213-23 (2010)). Recently, sortilin-apoB100 interaction was reported to be stimulated by insulin (Chamberlain, Biochem Biophys Res Commun. 50006-291X(12)02182-1 (2012) Epub ahead of print). Sortilin is also involved in the trafficking of prosaposin, acid sphingomye-linase and Cathepsin H and D to lysosomes. Sortilin was recently reported to bind APOE, a major risk factor in Alzheimers Disease as well as to soluble APP in primary hippocampal neurons (Carlo et al, J Neurosci, 33(1):358-70 (2013); Gustafsen et al, J Neurosci, 33(1):64-71 (2013)).

Gene polymorphisms on chromosome 1p13 have linked Sortl with metabolism of low density lipoprotein (LDL) cholesterol and risk of myocardial infarction or coronary artery disease in human patients (Linsel-Nitschke et al, Atherosclerosis., 208(1):183-9 (2010), Musunuru et al, Nature, 466(7307):714-9 (2010)). In one study, increased expression of sortilin associated with the polymorphism rs599839 was found to be correlated with lower levels of plasma LDL-cholesterol and decreased risk of coronary artery disease (Linsel-Nitschke et al, Atherosclerosis., 208 (1):183-9 (2010)). However, other studies suggested that absence of sortilin resulted in decreased plasma cholesterol levels and in decreased plaque formation in aorta in mice deficient for the LDL receptor (Kjolby et al, Cell Metab, 12(3):213-23 (2010))). Thus, the mechanism linking sortilin to LDL metabolism and the net effect of altered sortilin expression is still a matter of debate (Dube et al, Bioessays., 33(6):430-7 (2011), Strong et al, Curr Atheroscler Rep., 14(3):211-8 (2012)) although there is agreement that sortilin associates with levels of circulating cholesterol/LDL and that modulation of sortilin function may represent a strategy to reduce levels of circulating LDL and alleviate cardiovascular risk.

Due to studies associating sortilin function with disease and the binding of sortilin to several proteins implicated in pathologies in the central nervous system as well as in the periphery, sortilin may represent an attractive therapeutic target. However, although the binding site of the sortilin ligands neurotensin and progranulin has been identified, no specific small molecule modulator of sortilin function has been disclosed to date.

The present invention aims at providing compounds which are inhibitors of sortilin and as such useful in the treatment of diseases associated with sortilin.

SUMMARY OF THE INVENTION

The present inventors have surprisingly found certain compounds which are Sortilin inhibitors. Accordingly, in one embodiment the invention provides compounds of Formula A, below

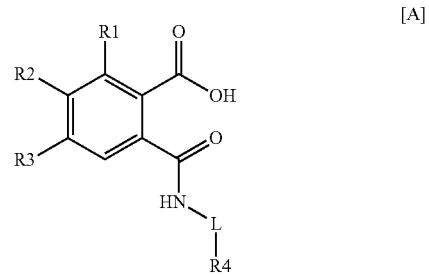

wherein
R1 represents H or F,
R2 represents halogen, $C_1$-$C_6$ alkyl, $C_2$-$C_6$ alkenyl or $C_1$-$C_6$ halogenated alkyl,
R3 represents halogen, H, $C_1$-$C_6$ alkyl or $C_1$-$C_6$ halogenated alkyl,
L is a direct bond or represents $CH_2$,
R4 represents a 5-6 membered heteroaromatic monocyclic ring with 1 or 2 heteroatom(s) or a 8-10 membered bicyclic heterocyclic ring with 1 or 2 heteroatom(s), said heteroaromatic or bicyclic ring may be substituted with C═N, 1 or 2 $C_1$-$C_3$ alkyl, 1 or 2 $C_1$-$C_3$ alkoxy or 1 or 2 halogen(s),
and pharmaceutically acceptable salts or prodrugs thereof with the proviso that the compound is not 5-methyl-2-[[(4-methyl-2-thiazolyl)amino]carbonyl].

In one embodiment, the invention provides a pharmaceutical composition comprising a compound of the above formula A and pharmaceutically acceptable salts thereof together with a pharmaceutically acceptable excipient.

In one embodiment, the invention provides compounds of the above formula A and pharmaceutically acceptable salts thereof for use in therapy.

In one embodiment, the invention provides compounds of the above formula A and pharmaceutically acceptable salts thereof for use in the treatment of a neurodegenerative disease, psychiatric disease, motorneuron disease, peripheral neuropathies, pain, neuroinflammation or atherosclerosis.

In one embodiment, the invention relates to the use of a compound of the above formula A and pharmaceutically acceptable salts thereof in the manufacture of a medicament for use in the treatment of a neurodegenerative disease, psychiatric disease, motorneuron disease, peripheral neuropathies, pain, neuroinflammation or atherosclerosis.

In one embodiment, the invention relates to a method for the treatment of neurodegenerative disease, psychiatric disease, motorneuron disease, peripheral neuropathies, pain, neuroinflammation or atherosclerosis, the method comprising the administration of a therapeutically effective amount of a compound of the above formula A and pharmaceutically acceptable salts thereof to a patient in need thereof.

DETAILED DESCRIPTION OF THE INVENTION

Figure 1:
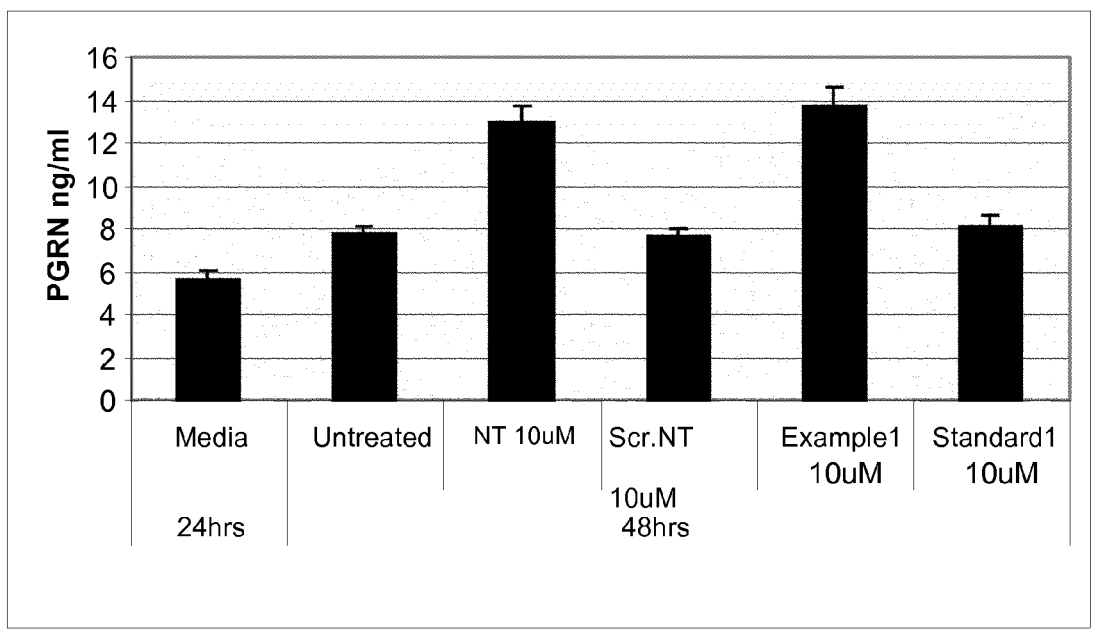
FIG. 1, shows that the addition of Neurotensin (NT) or the compound from Example 1 in the presence of PGRN blocks interaction with sortilin, as seen the figure by the increase in PGRN levels.

In further embodiments, said R4 group in formula A hereinabove may be selected from the group comprising

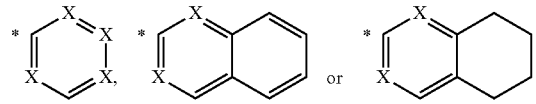

* denotes the attachment point.
which groups may optionally be substituted with C≡N, 1 or 2 $C_1$-$C_3$ alkyl, 1 or 2 halogenated alkyl, 1 or 2 $C_1$-$C_3$ alkoxy or 1 or 2 halogen(s), wherein X denotes C or N and N is present at 1 or 2 positions.

In another embodiment R4 may be

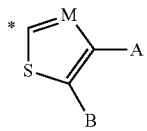

Wherein M represents C, N or CC≡N,
A and B each independently represents H, $C_1$-$C_3$ alkyl, or A and B forms a 5, 6 or 7 membered carbocyclic saturated or unsaturated ring together with the carbon atom they are attached to, and
* denotes the attachment point.

In a yet another embodiment the halogenated $C_1$-$C_6$ halogenated alkyl in R2 and R3 of Formula A may each independently be $CF_3$. In another embodiment R2 may be Cl, Br or $CF_3$ and R3 may be H or Cl.

In still further embodiments, the compound according to Formula A hereinabove may have a R4 group selected from the group comprising

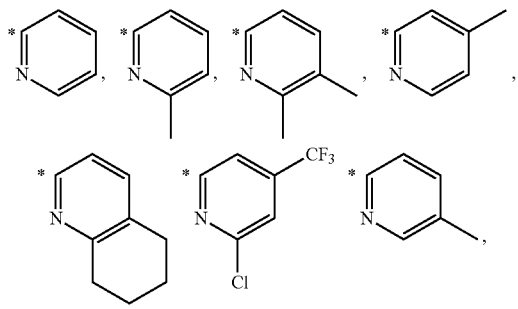

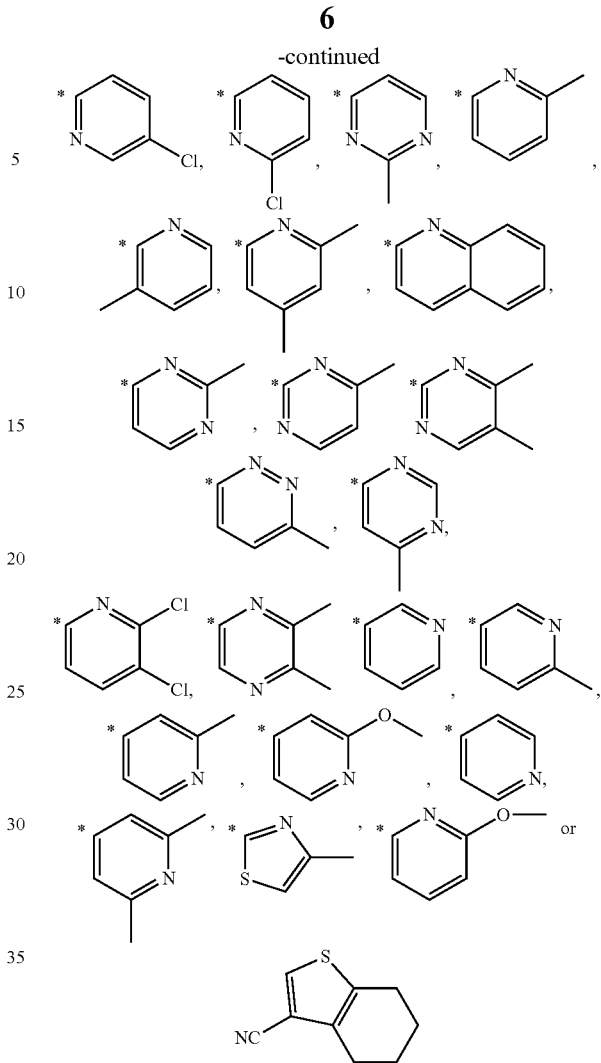

* denotes the attachment point
which groups may optionally be substituted with C≡N, 1 or 2 $C_1$-$C_3$ alkyl, 1 or 2 halogenated alkyl, 1 or 2 $C_1$-$C_3$ alkoxy or 1 or 2 halogen(s).

In a specific embodiment the compound according to Formula A may be selected from the group comprising,
N-(6-Methyl-pyridin-2-yl)-5-trifluoromethyl-phthalamic acid
5-Bromo-N-(6-methyl-pyridin-2-yl)-phthalamic acid
5-Methyl-N-(6-methyl-pyridin-2-yl)-phthalamic acid
5-Chloro-N-(6-methyl-pyridin-2-yl)-phthalamic acid
4,5-Dichloro-N-(6-methyl-pyridin-2-yl)-phthalamic acid
5-Bromo-N-(3-methyl-4,5,6,7-tetrahydro-benzo[b]thiophen-2yl)-phthalamic acid
N-(5,6-Dimethyl-pyridin-2-yl)-5-trifluoromethyl-phthalamic acid
N-(4-methyl-pyridin-2-yl)-5-trifluoromethyl-phthalamic acid
N-(2-methyl-pyridin-4-yl)-5-trifluoromethyl-phthalamic acid
4,5-Dichloro-N-(4-methyl-pyridin-2-yl)-phthalamic acid
4,5-Dichloro-N-(5,6-Dimethyl-pyridin-2-yl)-phthalamic acid
4,5-Dichloro-N-(2-methyl-pyridin-4-yl)-phthalamic acid
4,5-Dichloro-N-(2-methyl-pyrimidin-4-yl)-phthalamic acid
5-Chloro-6-fluoro-N-(6-methyl-pyridin-2-yl)-phthalamic acid 4,5-Dimethyl-N-(6-methyl-pyridin-2-yl)-phthalamic acid
2-((3-chloro-5-(trifluoromethyl)pyridin-2-yl)carbamoyl)-5-(trifluoromethyl)benzoic acid
2-((4-methylpyrimidin-2-yl)carbamoyl)-5-(trifluoromethyl)benzoic acid
2-((5,6-dimethylpyrazin-2-yl)carbamoyl)-5-(trifluoromethyl)benzoic acid
5-Bromo-N-(5-methyl-pyridin-2-yl)-phthalamic acid
5-Bromo-N-(5-chloro-pyridin-2-yl)-phthalamic acid
5-Bromo-N-pyridin-2-yl-phthalamic acid
5-Bromo-N-(6-chloro-pyridin-2-yl)-phthalamic acid
5-Bromo-N-(5,6-dimethyl-pyridin-2-yl)-phthalamic acid
5-Bromo-N-(4-methyl-pyridin-2-yl)-phthalamic acid
5-Bromo-N-(2-methyl-pyridin-4-yl)-phthalamic acid
5-Bromo-N-pyridin-3-yl-phthalamic acid
5-Bromo-N-(3-methyl-pyridin-2-yl)-phthalamic acid
5-Bromo-N-(4-methyl-thiazol-2-yl)-phthalamic acid
5-Bromo-N-quinolin-2-yl-phthalamic acid
5-Bromo-N-(5,6-dichloro-pyridin-2-yl)-phthalamic acid
5-Bromo-N-(6-methyl-pyridin-3-yl)-phthalamic acid
5-Bromo-N-(6-methyl-pyridazin-3-yl)-phthalamic acid
5-Bromo-N-(4,6-dimethyl-pyridin-2-yl)-phthalamic acid
5-Bromo-N-(2-methyl-pyrimidin-4-yl)-phthalamic acid
5-Bromo-N-(6-methyl-pyrimidin-4-yl)-phthalamic acid
N-(2-Methoxy-pyridin-4-yl)-5-trifluoromethyl-phthalamic acid
N-(6-Methoxy-pyridin-2-yl)-5-trifluoromethyl-phthalamic acid
N-Pyridin-2-ylmethyl-5-trifluoromethyl-phthalamic acid
N-Pyridin-4-ylmethyl-5-trifluoromethyl-phthalamic acid
N-Pyridin-3-ylmethyl-5-trifluoromethyl-phthalamic acid
N-(6-Methyl-pyridin-2-yl)-5-propyl-phthalamic acid
N 5-Isopropenyl-N-(6-methyl-pyridin-2-yl)-phthalamic acid
N 5-Isopropyl-N-(6-methyl-pyridin-2-yl)-phthalamic acid
2-((2-methylpyrimidin-4-yl)carbamoyl)-5-(trifluoromethyl)benzoic acid
2-((4,5-dimethylpyrimidin-2-yl)carbamoyl)-5-(trifluoromethyl)benzoic acid
2-((5,6,7,8-tetrahydroquinolin-2-yl)carbamoyl)-5-(trifluoromethyl)benzoic acid
2-((6-methylpyridin-2-yl)carbamoyl)-4,5-bis(trifluoromethyl)benzoic acid
2-((5,6,7,8-tetrahydroquinolin-2-yl)carbamoyl)-4,5-bis(trifluoromethyl)benzoic acid
2-((5,6-dimethylpyridin-2-yl)carbamoyl)-4,5-bis(trifluoromethyl)benzoic acid
2-((2-methylpyrimidin-4-yl)carbamoyl)-4,5-bis(trifluoromethyl)benzoic acid
2-((2,6-dimethylpyridin-4-yl)carbamoyl)-5-(trifluoromethyl)benzoic acid
or pharmaceutical acceptable salt or prodrug thereof.

The above mentioned compounds may be in a composition as the sole active ingredient or in combination with other active ingredients. Additionally one or more pharmaceutically acceptable carriers or diluents may be in the composition.

In certain aspects the invention also relates to prodrugs of formula A, and thus the use of certain compounds as products in therapy, in particular those of formula B and C disclosed below.

By "prodrug" is intended to mean a medication that is initially administered to the body in an inactive or less than fully active form, which becomes converted to its active form through the normal metabolic processes of the body.

Thus the invention also relates to prodrugs of formula B and the use of these compounds as prodrugs in therapy:

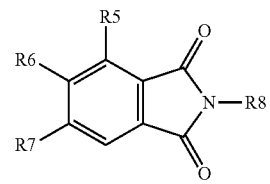

wherein
R5 represents H or F,
R6 represents halogen, $C_1$-$C_6$ alkyl, $C_2$-$C_6$ alkenyl or $C_1$-$C_6$ halogenated alkyl,
R7 represents halogen, H, $C_1$-$C_6$ alkyl or $C_1$-$C_6$ halogenated alkyl,
R8 represents a 5-6 membered heteroaromatic monocyclic ring with 1 or 2 heteroatom(s) or a 8-10 membered bicyclic heterocyclic ring with 1 or 2 heteroatom(s), said heteroaromatic or bicyclic rings may be substituted with C≡N, 1 or 2 $C_1$-$C_3$ alkyl, 1 or 2 halogenated alkyl, 1 or 2 $C_1$-$C_3$ alkoxy or 1 or 2 halogen(s) and pharmaceutically acceptable salts thereof R6 may in certain embodiments represent $CH_3$, Br, Cl or $CF_3$ and R7 may represent H or Cl. Furthermore the prodrug of formula B may have an R5 being H and R6 and R7 which are identical.

R8 may in certain embodiments be selected from the group comprising

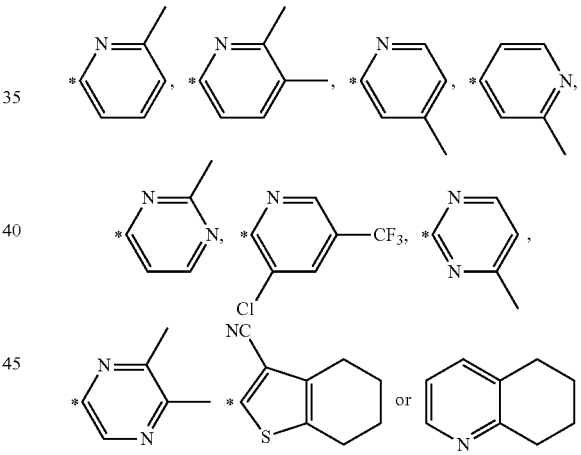

In a specific embodiment the prodrug according to formula B may be selected from the group comprising
2-(6-Methyl-pyridin-2-yl)-5-trifluoromethyl-isoindole-1,3-dione
5-Bromo-2-(6-methyl-pyridin-2-yl)-isoindole-1,3-dione
5-Methyl-2-(6-methyl-pyridin-2-yl)-isoindole-1,3-dione
5-Chloro-2-(6-methyl-pyridin-2-yl)-isoindole-1,3-dione
5,6-Dichloro-2-(6-methyl-pyridin-2-yl)-isoindole-1,3-dione
2-(5-Bromo-1,3-dioxo-1,3-dihydro-isoindol-2-yl)-4,5,6,7-tetrahydro-benzo[b]thiophene-3-carbonitrile
2-(5,6-Dimethyl-pyridin-2-yl)-5-trifluoromethyl-isoindole-1,3-dione
2-(4-Methyl-pyridin-2-yl)-5-trifluoromethyl-isoindole-1,3-dione
2-(2-Methyl-pyridin-4-yl)-5-trifluoromethyl-isoindole-1,3-dione
5,6-Dichloro-2-(4-methyl-pyridin-2-yl)-isoindole-1,3-dione 5,6-Dichloro-2-(5,6-dimethyl-pyridin-2-yl)-isoindole-1,3-dione
5,6-Dichloro-2-(2-methyl-pyridin-4-yl)-isoindole-1,3-dione
5,6-Dichloro-2-(2-methyl-pyrimidin-4-yl)-isoindole-1,3-dione
5-Chloro-4-fluoro-2-(6-methyl-pyridin-2-yl)-isoindole-1,3-dione
5,6-Dimethyl-2-(6-methyl-pyridin-2-yl)-isoindole-1,3-dione
2-(3-Chloro-5-trifluoromethyl-pyridin-2-yl)-5-trifluoromethyl-isoindole-1,3-dione
2-(4-Methyl-pyrimidin-2-yl)-5-trifluoromethyl-isoindole-1,3-dione
2-(5,6-Dimethyl-pyrazin-2-yl)-5-trifluoromethyl-isoindole-1,3-dione
2-(6-Methyl-pyridin-2-yl)-5,6-bis-trifluoromethyl-isoindole-1,3-dione
2-(5,6,7,8-Tetrahydro-quinolin-2-yl)-5,6-bis-trifluoromethyl-isoindole-1,3-dione
or a pharmaceutical acceptable salt thereof In an even further aspect the invention relates to a prodrug according to formula C and the use of these compounds in therapy:

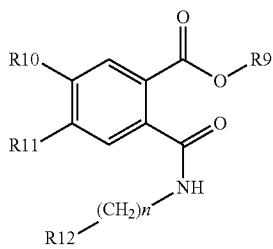

wherein
R9 represents $C_1$-$C_6$ alkyl
R10 represents halogen, $C_1$-$C_6$ alkyl, $C_2$-$C_6$ alkenyl or $C_1$-$C_6$ halogenated alkyl,
R11 represents halogen, H, $C_1$-$C_6$ alkyl or $C_1$-$C_6$ halogenated alkyl,
n is 0 or 1,
R12 represents a 5-6 membered heteroaromatic monocyclic ring with 1 or 2 heteroatom(s) or a 8-10 membered bicyclic heterocyclic ring with 1 or 2 heteroatom(s), said heteroaromatic or bicylic rings may be substituted with C≡N, 1 or 2 $C_1$-$C_3$ alkyl, 1 or 2 halogenated alkyl, 1 or 2 $C_1$-$C_3$ alkoxy or 1 or 2 halogen(s), and pharmaceutically acceptable salts thereof.

In another embodiment R9 represents $C_1$-$C_4$ alkyl
In another embodiment the prodrugs according to formula C may have R10 representing $CH_3$, $CHCH_2$, Br, Cl, Cl, C≡N or $CF_3$ and R7 representing H, $CF_3$ or Cl.
R12 may in certain embodiments be selected from the group comprising

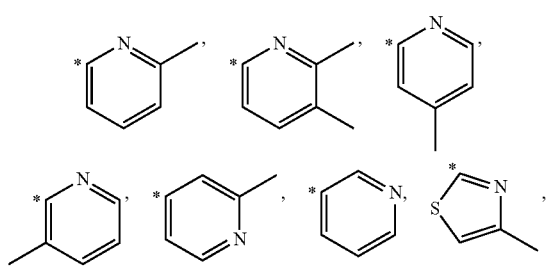

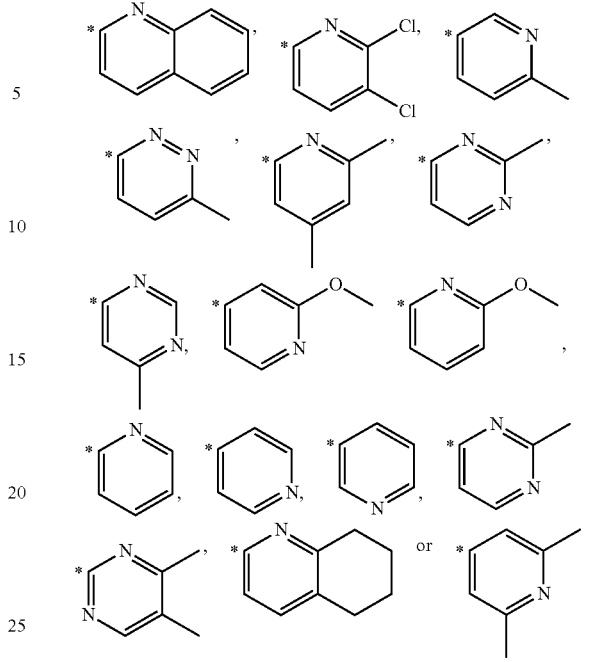

In a specific embodiment the prodrug according to formula C may be selected from the group comprising
5-Bromo-N-(5,6-dimethyl-pyridin-2-yl)-phthalamic acid tert-butyl ester
N-(6-Methyl-pyridin-2-yl)-5-trifluoromethyl-phthalamic acid tert-butyl ester
5-Bromo-N-(6-methyl-pyridin-2-yl)-phthalamic acid tert-butyl ester
5-Bromo-N-(5-methyl-pyridin-2-yl)-phthalamic acid tert-butyl ester
5-Bromo-N-(2-methyl-pyridin-4-yl)-phthalamic acid tert-butyl ester
5-Bromo-N-pyridin-3-yl-phthalamic acid tert-butyl ester
5-Bromo-N-(3-methyl-pyridin-2-yl)-phthalamic acid tert-butyl ester
5-Bromo-N-(4-methyl-thiazol-2-yl)-phthalamic acid tert-butyl ester
5-Bromo-N-quinolin-2-yl-phthalamic acid tert-butyl ester
5-Bromo-N-(5,6-dichloro-pyridin-2-yl)-phthalamic acid tert-butyl ester
5-Bromo-N-(6-methyl-pyridin-3-yl)-phthalamic acid tert-butyl ester
5-Bromo-N-(6-methyl-pyridazin-3-yl)-phthalamic acid tert-butyl ester
5-Bromo-N-(4,6-dimethyl-pyridin-2-yl)-phthalamic acid tert-butyl ester
5-Bromo-N-(2-methyl-pyrimidin-4-yl)-phthalamic acid tert-butyl ester
5-Bromo-N-(6-methyl-pyrimidin-4-yl)-phthalamic acid tert-butyl ester
N-(2-Methoxy-pyridin-4-yl)-5-trifluoromethyl-phthalamic acid tert-butyl ester
N-(6-Methoxy-pyridin-2-yl)-5-trifluoromethyl-phthalamic acid tert-butyl ester
N-Pyridin-2-ylmethyl-5-trifluoromethyl-phthalamic acid tert-butyl ester
N-Pyridin-4-ylmethyl-5-trifluoromethyl-phthalamic acid tert-butyl ester N-Pyridin-3-ylmethyl-5-trifluoromethyl-phthalamic acid tert-butyl ester
Not Applicable—not a pro-drug
5-Isopropenyl-N-(6-methyl-pyridin-2-yl)-phthalamic acid tert-butyl ester
N-(6-Methyl-pyridin-2-yl)-5-propyl-phthalamic acid tert-butyl ester
N-(2-Methyl-pyrimidin-4-yl)-5-trifluoromethyl-phthalamic acid tert-butyl ester
N-(4,5-Dimethyl-pyrimidin-2-yl)-5-trifluoromethyl-phthalamic acid tert-butyl ester
N-(5,6,7,8-Tetrahydro-quinolin-2-yl)-5-trifluoromethyl-phthalamic acid tert-butyl ester
5-Isopropyl-N-(6-methyl-pyridin-2-yl)-phthalamic acid tert-butyl ester
N-(2,6-Dimethyl-pyridin-4-yl)-5-trifluoromethyl-phthalamic acid tert-butyl ester
4,5-Dichloro-N-(6-methyl-pyridin-2-yl)-phthalamic acid tert-butyl ester
4,5-Dichloro-N-(6-methyl-pyridin-2-yl)-phthalamic acid isopropyl ester
4,5-Dichloro-N-(6-methyl-pyridin-2-yl)-phthalamic acid methyl ester
4,5-Dichloro-N-(2-methyl-pyrimidin-4-yl)-phthalamic acid isopropyl ester
4,5-Dichloro-N-(2-methyl-pyrimidin-4-yl)-phthalamic acid ethyl ester
N-(5,6-Dimethyl-pyridin-2-yl)-4,5-bis-trifluoromethyl-phthalamic acid methyl ester
or a pharmaceutical acceptable salt thereof.

It is envisaged that the prodrugs of formula C or B may be administered in a pharmaceutical formulations together with one or more pharmaceutical acceptable carriers of diluents. The use of these prodrugs are envisaged for the same medical conditions as those compounds of formula A.

The compounds of the present invention may have one or more asymmetric centres and it is intended that any optical isomers (i.e. enantiomers or diastereomers) as separated, pure or partially purified optical isomers and any mixtures thereof including racemic mixtures, i.e. a mixture of stereoisomeres, are included within the scope of the invention.

In this context is understood that when specifying the diastereomers form, the compound is in diastereomers excess, e.g. essentially in a pure form. Accordingly, one embodiment of the invention relates to a compound of the invention having an diastereomers excess of at least 60%, at least 70%, at least 80%, at least 85%, at least 90%, at least 96%, preferably at least 98%.

Racemic forms can be resolved into the optical antipodes by known methods, for example by separation of diastereomeric salts thereof with an optically active acid, and liberating the optically active amine compound by treatment with a base. Another method for resolving racemates into the optical antipodes is based upon chromatography on an optically active matrix. The compounds of the present invention may also be resolved by the formation of diastereomeric derivatives. Additional methods for the resolution of optical isomers, known to those skilled in the art, may be used. Such methods include those discussed by J. Jaques, A. Collet and S. Wilen in "Enantiomers, Racemates, and Resolutions", John Wiley and Sons, New York (1981). Optically active compounds can also be prepared from optically active starting materials.

Furthermore, when a double bond or a fully or partially saturated ring system is present in the molecule geometric isomers may be formed. It is intended that any geometric isomers as separated, pure or partially purified geometric isomers or mixtures thereof are included within the scope of the invention. Likewise, molecules having a bond with restricted rotation may form geometric isomers. These are also intended to be included within the scope of the present invention.

Furthermore, some of the compounds of the present invention may exist in different tautomeric forms and it is intended that any tautomeric forms that the compounds are able to form are included within the scope of the present invention.

In the present context, "pharmaceutically acceptable salts" include pharmaceutical acceptable acid addition salts, pharmaceutically acceptable metal salts, ammonium and alkylated ammonium salts. Acid addition salts include salts of inorganic acids as well as organic acids.

Examples of metal salts include lithium, sodium, potassium, magnesium salts and the like.

Examples of ammonium and alkylated ammonium salts include ammonium, methyl-, dimethyl-, trimethyl-, ethyl-, hydroxyethyl-, diethyl-, n-butyl-, sec-butyl-, tert-butyl-, tetramethylammonium salts and the like.

In the present context, "alkyl" and "alkenyl" is intended to indicate a straight or branched saturated hydrocarbon. The term "alkenyl" embraces radicals having at least one carbon-carbon double bond. In particular, $C_{1-6}$-alkyl or $C_{2-6}$-alkenyl are intended to indicate such hydrocarbon having 1, 2, 3, 4, 5 or 6 carbon atoms or 2, 3, 4, 5 or 6 carbon atoms, respectively, and likewise $C_{1-3}$-alkyl or $C_{2-3}$-alkenyl is intended to indicate a hydrocarbon having 1, 2 or 3 carbon atoms or 2 or 3 carbon atoms, respectively.

Typical alkyl groups include, but are not limited to, methyl, ethyl, propyl, isopropyl, butyl, isobutyl, t-butyl, pentyl, isopentyl, hexyl and the like. The "alkyl" group may be substituted with one or more, such as 1, 2 or 3, halogen(s), thus constituting a halogenated alkyl such as fluoroethyl, trifluoromethyl or trifluoroethyl.

The term "alkoxy" as used herein refers to a group of formula —O— alkyl, wherein alkyl is defined as above. In particular, $C_1$-$C_3$-akoxy is intended to indicate such hydrocarbon having 1, 2 or 3 carbon atoms. Examples of alkoxy groups include methoxy, ethoxy, n-propoxy, and isopropoxy.

In the present context, "halogen" is intended to indicate members of the $7^{th}$ main group of the periodic table of the elements, such as fluoro, chloro, bromo and iodo.

By "heteroatom" is intended to mean sulfur, oxygen or nitrogen.

The term "aromatic" refers to a cyclic or polycyclic moiety having a conjugated unsaturated $(4n+2)\pi$ electron system (where n is a positive integer), sometimes referred to as a delocalized $\pi$ electron system.

The term "heterocyclic" as used herein, alone or in combination, refers to saturated or unsaturated aromatic or nonaromatic rings containing from 5 to 6 ring atoms where 1 or 2 of the ring atoms are heteroatom(s).

The term "heteroaromatic" as used herein, alone or in combination, refers to an aromatic ring containing from 5 to 6 ring atoms where 1 or 2 of the ring atoms are heteroatom(s).

The term "bicyclic heterocyclic ring" refers to 2 fused cyclic rings wherein each may be saturated or unsaturated to form a "bicyclic heterocyclic ring" of a total of 8-10 members. This bicyclic heterocyclic ring may have 1 or 2 heteroatom(s) in one or both of the rings. In one embodiment the bicyclic ring constitute a heteroaromatic ring fused to a saturated or unsaturated carbocyclic ring (i.e. a cyclic ring in which all of the ring members are carbon atoms) or heterocyclic ring.

The terms "substituents" or "substituted" as used herein, alone or in combination, refer to groups which may be used to replace hydrogen. The substituted molecule may itself be further substituted in some embodiments of the invention.

In the present context, the term "therapeutically effective amount" of a compound is intended to indicate an amount sufficient to cure, alleviate or partially arrest the clinical manifestations of a given disease and its complications in a therapeutic intervention comprising the administration of said compound. An amount adequate to accomplish this is defined as "therapeutically effective amount". Effective amounts for each purpose will depend on the severity of the disease or injury as well as the weight and general state of the subject. It will be understood that determining an appropriate dosage may be achieved using routine experimentation, e.g. by constructing a matrix of values and testing different points in the matrix, which is all within the ordinary skills of a trained physician.

In the present context, the term "treatment" and "treating" means the management and care of a patient for the purpose of combating a disease. The term is intended to include the full spectrum of treatments for a given disease from which the patient is suffering, such as administration of the active compound to alleviate the symptoms or complications, to delay the progression of the disease, to alleviate or relief the symptoms and complications, and/or to cure or eliminate the disease. The patient to be treated is preferably a mammal, in particular a human being. In the present context, "disease" can be used synonymous with disorder, condition, malfunction, dysfunction and the like.

As established above, Sortilin inhibitors may by used in the treatment of neurodegenerative disease, psychiatric disease, motorneuron disease, peripheral neuropathies, pain, neuroinflammation or atherosclerosis.

Thus, the compounds as outlined in Formula A, the compounds of formula B and C as prodrugs, or composition comprising said compounds may be used in a method for treatment selected from the group comprising Alzheimer's disease, Parkinson's disease, stroke, traumatic brain injury, retinal degeneration, light-induced photoreceptor degeneration, epilepsy, bipolar disorder, Amyotrophic lateral sclerosis (ALS), Frontotemporal lobar degeneration (FTLD), spinal muscular atrophy, peripheral neuropathy, diabetic neuropathy, acute and chronic pain, prevention and treatment of established pain, neuropathic pain, lower back pain, post operative pain, inflammatory pain, rheumatoid arthritis, Crohns disease, ulcerative colitis, multiple sclerosis and atherosclerosis.

In one embodiment, the compound of the present invention is administered in an amount from about 0.001 mg/kg body weight to about 100 mg/kg body weight per day. In particular, daily dosages may be in the range of 0.01 mg/kg body weight to about 50 mg/kg body weight per day. The exact dosages will depend upon the frequency and mode of administration, the sex, the age the weight, and the general condition of the subject to be treated, the nature and the severity of the condition to be treated, any concomitant diseases to be treated, the desired effect of the treatment and other factors known to those skilled in the art.

A typical oral dosage for adults will be in the range of 1-1000 mg/day of a compound of the present invention, such as 1-500 mg/day.

The compounds of the present invention may be administered alone as a pure compound or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 21 Edition, PA, 2005. In the present context, "excipient", "carrier", "diluent", "adjuvant" and the like are used synonymously and are intended to mean the same.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings.

Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use.

Other suitable administration forms include suppositories, sprays, ointments, cremes, gels, inhalants, dermal patches, implants, etc.

Conveniently, the compounds of the invention are administered in a unit dosage form containing said compounds in an amount of about 0.1 to 500 mg, such as 10 mg, 50 mg 100 mg, 150 mg, 200 mg or 250 mg of a compound of the present invention.

For parenteral administration, solutions of the compound of the invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospho lipids, fatty acids, fatty acid amines, polyoxyethylene and water. The pharmaceutical compositions formed by combining the compound of the invention and the pharmaceutical acceptable carriers are then readily administered in a variety of dosage forms suitable for the disclosed routes of administration.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

If a solid carrier is used for oral administration, the preparation may be tablet, e.g. placed in a hard gelatine capsule in powder or pellet form or in the form of a troche or lozenge. The amount of solid carrier may vary but will usually be from about 25 mg to about 1 g.

If a liquid carrier is used, the preparation may be in the form of a syrup, emulsion, soft gelatine capsule or sterile injectable liquid such as an aqueous or non-aqueous liquid suspension or solution.

Tablets may be prepared by mixing the active ingredient with ordinary adjuvants and/or diluents followed by the compression of the mixture in a conventional tabletting machine. Examples of adjuvants or diluents comprise: Corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law), regardless of any separately provided incorporation of particular documents made elsewhere herein.

The use of the terms "a" and "an" and "the" and similar referents in the context of describing the invention are to be construed to cover both the singular and the plural, unless otherwise indicated herein or clearly contradicted by context. For example, the phrase "the compound" is to be understood as referring to various "compounds" of the invention or particular described aspect, unless otherwise indicated.

The description herein of any aspect or aspect of the invention using terms such as "comprising", "having," "including," or "containing" with reference to an element or elements is intended to provide support for a similar aspect or aspect of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

Experimental

Abbreviations and Chemicals Used aq=aqueous. Brine=saturated aq solution of sodium chloride (e.g. Sigma-Aldrich S7653). CDCl$_3$=deuterated chloroform (e.g. Aldrich 225789). DCM=methylene chloride/dichloromethane (e.g. Sigma-Aldrich 270997). DIPEA=di-iso-propyl ethyl amine (e.g. Sigma-Aldrich 387649). DMF=dimethyl formamide (e.g. Sigma-Aldrich 227056). DMSO-d6=deutorated dimethyl sulfoxide (e.g. Aldrich 296147). Et$_3$N=triethylamine (e.g. Sigma-Aldrich T0886). Et$_2$O=diethyl ether (e.g. Sigma-Aldrich 346136). EtOAc=ethyl acetate (e.g. Fluka 34972). EtOH=ethanol (e.g. Sigma-Aldrich 459844). h=hour(s). HART=O-(7-azabenzotriazol-1-yl)-N,N,N',N'-tetramethyluronium hexafluorophosphate. Heptanes (e.g. Sigma-Aldrich 730491). K$_3$PO$_4$ (e.g. Sigma-Aldrich P5629). LCMS=liquid chromatography/mass spectrometry. LiOH=lithium hydroxide (e.g. Sigma-Aldrich 545856). MeOH=methanol (e.g. Sigma.Aldrich 34860). MgSO$_4$ (e.g. Sigma-Aldrich M7506). Microwave=a Biotage initiator microwave reactor. Min=minute(s). NaHCO$_3$ (e.g. Sigma-Aldrich S6014). NaOt-Bu=sodium tert-butoxide (e.g. Aldrich 359270). Na$_2$SO$_4$=sodium sulfate (e.g. Sigma-Aldrich 238597). NMP=1-methyl-2-pyrrolidinone (e.g. Sigma-Aldrich 443778). NMR=nuclear magnetic resonance. PDA=photo diode array. Pd(OAc)$_2$=palladium(II) acetate (e.g. Aldrich 683124). Pd(PPh$_3$)$_2$Cl$_2$=bis(triphenylphosphine)palladium (II) dichloride (e.g. Aldrich 208671). Petroleum ether (e.g. Sigma-Aldrich 77379). POCl$_3$=phosphoryl chloride (e.g. Aldrich 262099). Prep. HPLC=preparative high performance liquid chromatography. Pyridine (e.g. Sigma-Aldrich 270970). Rt=room temperature. Silica gel=particle size 100-200 mesh (75-150 μm). SFC=Supercritical Fluid Chromatography. SOCl$_2$=thionyl chloride (e.g. Sigma-Aldrich 320536). TFA=trifluoroacetic acid (e.g. Sigma-Aldrich T6508). THF=tetrahydrofuran (e.g. Sigma-Aldrich 401757). TLC=thin layer chromatography. Toluene (e.g. Sigma-Aldrich 244511). tR=retention time.

Names

Chemical names were obtained using the software MDL ISIS/DRAW 2.5 from MDL information systems.

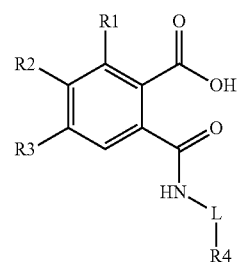

Compounds of general formula 1 can be prepared according to Scheme 1 where a corresponding phthalimide intermediate X is hydrolysed with a base such as, for example, lithium hydroxide.

For illustrative purposes A and B groups are used in the below schemes.

It will be appreciated that wherein substituent A≠B a mixture of two isomers 1 and 1a may be obtained (scheme 1), these isomers can be separated to afford the pure compounds via, for example, preparative HPLC.

Wherein B=H only isomer 1 is the subject of this invention, and the alternative isomer 1a can be discarded.

Wherein A=B, only a single compound will be obtained i.e. 1 and 1a are identical. Individual isomers 1 and 1a can be unambiguously characterised by NMR techniques.

Scheme 1

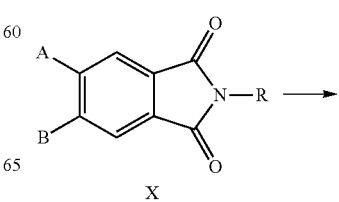

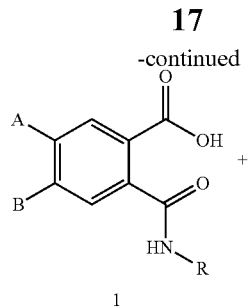

Phthalimide intermediates of general formula X can in turn be prepared by treatment of the corresponding phthalic anhydride W with the corresponding amino compound V in, for example, acetic acid at reflux (scheme 2).

Scheme 2

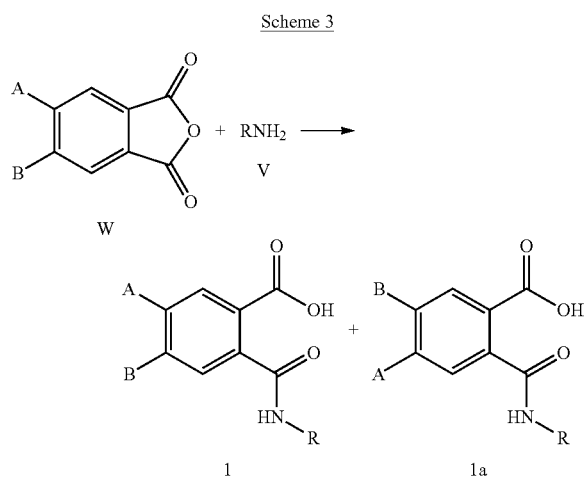

Alternatively compounds of general formula 1 (and 1a) can also be prepared by direct reaction of an amino compound V and the corresponding phthalic anhydride W in, for example, acetone (scheme 3).

Scheme 3

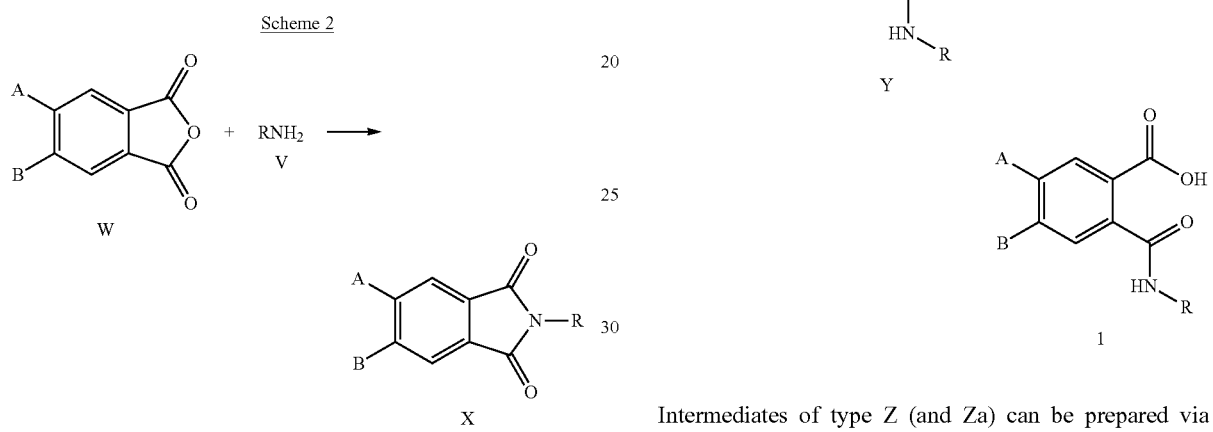

Alternatively compounds of general formula 1 can be prepared according to the chemistry of scheme 4. Coupling an amino compound V using, for example, a coupling agent such as HATU, to an intermediate of general formula Z affords an intermediate Y, from which the compound of general formula 1 may be obtained by debutylation of the ester using, for example, TFA.

Scheme 4

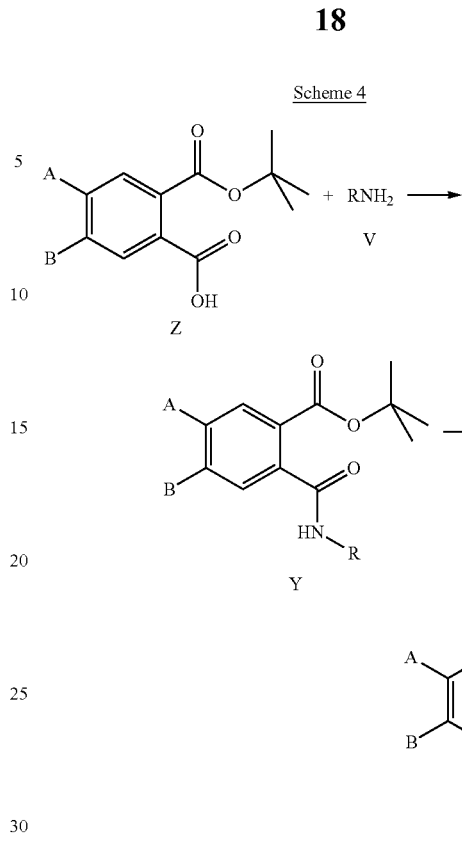

Intermediates of type Z (and Za) can be prepared via alchoholysis of a corresponding phthalic anhydride W with, for example, the alkoxide in water, and separation of the isomers Z and Za via supercritical fluid chromatography (SFC) (scheme 5).

Scheme 5

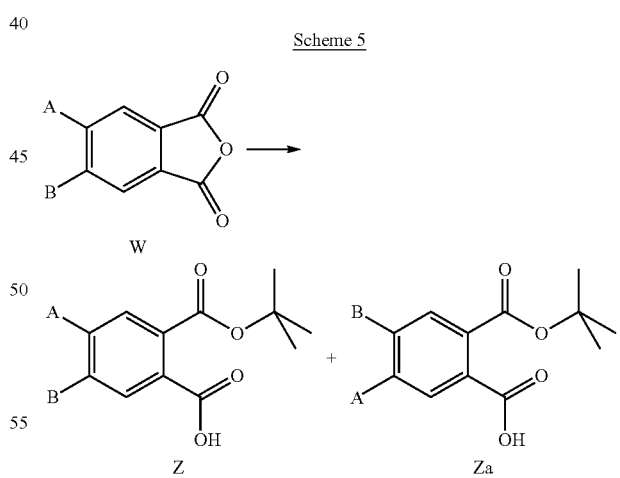

Intermediates of type Y may also be prepared by modification or functionalisation of one of the substituents of another intermediate of type Y, e.g. an intermediate of type Y' (scheme 6). For example, in an intermediate of type Y' wherein the substituent A' contains an alkene or alkyne, the substituent A' may be reduced with for example hydrogen and palladium on carbon catalyst to an alternative substituent A (scheme 6) to afford intermediate Y.

Scheme 6

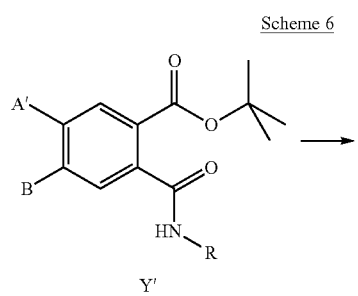

Moreover an intermediate of type Z may also be prepared by modification or functionalisation of one of the substituents of another intermediate of type Z, e.g. an intermediate of type Z' (scheme 7). For example, wherein the substituent A' of an intermediate of type Z' is a bromine atom, the bromine may be converted to another substituent A (scheme 7) using, for example, transition metal catalysed coupling, to afford an intermediate of type Z.

Scheme 7

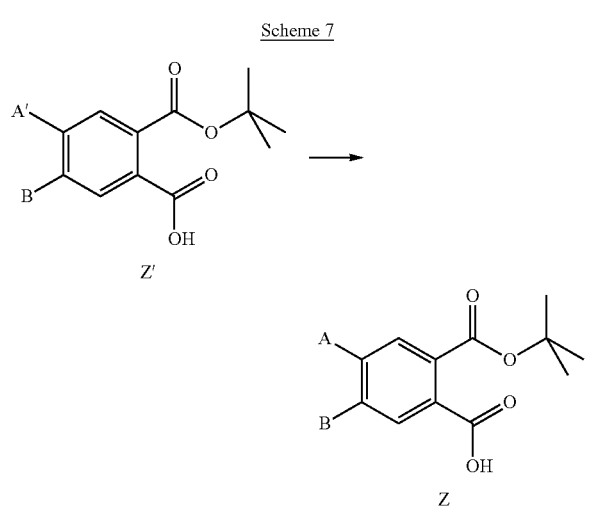

Additionally, compounds of general formula 1 can be prepared according to the chemistry of scheme 8. Coupling an amino compound V using, for example, a coupling agent such as HATU, to a symmetrical intermediate (i.e. A=B) of general formula T can afford compounds of general formula 1 directly.

Scheme 8

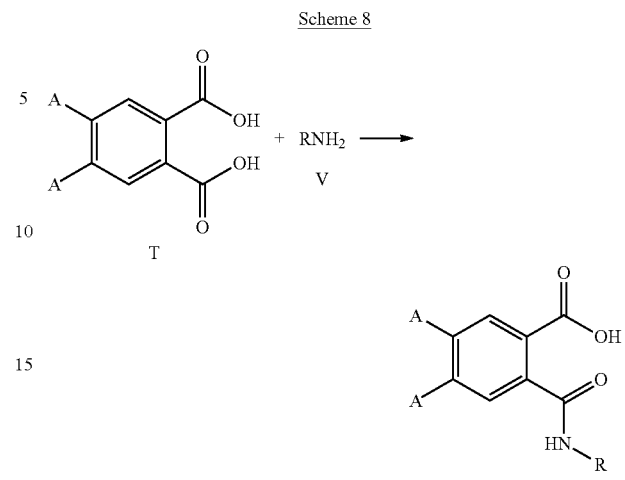

Additionally, compounds of general formula 1 can be prepared according to the chemistry of scheme 9. Coupling an amino compound V using, for example, trimethylaluminium, to a symmetrical intermediate (i.e. A=B) of general formula R affords an intermediate S. The compound of general formula 1 may now be obtained by hydrolysis of the ester using, for example, lithium hydroxide.

Scheme 9

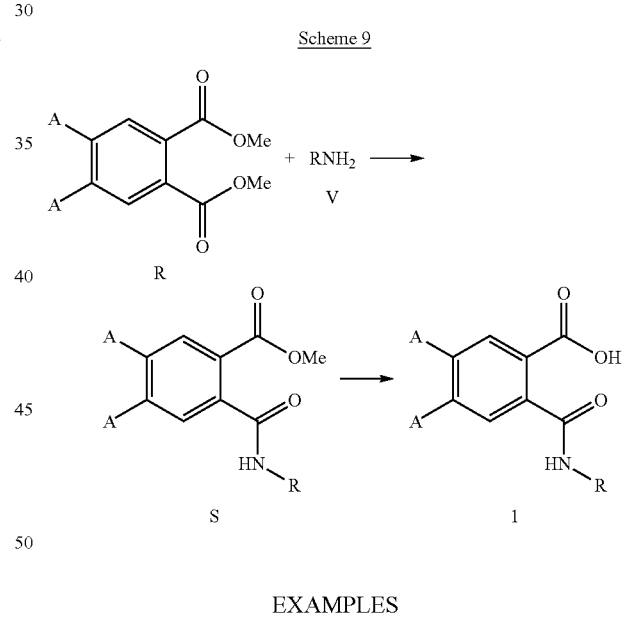

EXAMPLES

The invention will be illustrated by the following non-limiting examples.

Analytical Methods
LC-MS
Method A:
LC-MS were run on Waters Aquity UPLC-MS consisting of Waters Aquity including column manager, binary solvent manager, sample organizer, PDA detector (operating at 254 nM), ELS detector, and SQ-MS equipped with APPI-source operating in positive ion mode.

LC-conditions: The column was Acquity UPLC BEH C18 1.7 µm; 2.1×50 mm operating at 60° C. with 1.2 ml/min of a binary gradient consisting of water+0.1% formic acid (A) and acetonitrile+5% water+0.1% formic acid.

| Gradient: | 0.00 min | 10% B |
|---|---|---|
| | 1.00 min | 99.9% B |
| | 1.01 min | 10% B |
| | 1.15 min | 10% B |
| Total run time: | 1.15 min | |

Method B:

LC-MS were run on Waters Aquity UPLC-MS consisting of Waters Aquity including column manager, binary solvent manager, sample organizer, PDA detector (operating at 254 nM), ELS detector, and TQ-MS equipped with APPI-source operating in positive ion mode.

LC-conditions: The column was Acquity UPLC BEH C18 1.7 μm; 2.1×50 mm operating at 55° C. with 0.4 ml/min of a binary gradient consisting of water+0.1% formic acid (A) and acetonitrile+0.1% formic acid (B).

| Gradient: | 0.00 min | 3% B |
|---|---|---|
| | 0.50 min | 3% B |
| | 1.50 min | 90% B |
| | 1.80 min | 90% B |
| | 2.20 min | 95% B |
| | 3.20 min | 95% B |
| | 4.00 min | 3% B |
| Total run time: | 4.00 min | |

Method C:

LC-MS were run on Waters Aquity UPLC-MS consisting of Waters Aquity including column manager, binary solvent manager, sample organizer, PDA detector (operating at 254 nM), ELS detector, and TQ-MS equipped with APPI-source operating in positive ion mode.

LC-conditions: The column was ZORBAX RX C18 1.8μ; 2.1×50 mm operating at 55° C. with 0.4 ml/min of a binary gradient consisting of water+0.01% formic acid (A) and acetonitrile+0.01 formic acid (B).

| Gradient: | 0.00 min | 5% B |
|---|---|---|
| | 1.00 min | 5% B |
| | 4.00 min | 95% B |
| | 6.00 min | 95% B |
| | 6.10 min | 5% B |
| Total run time: | 6.10 min | |

Method D:

LC-MS were run on Waters Aquity UPLC-MS consisting of Waters Aquity including column manager, binary solvent manager, sample organizer, PDA detector (operating at 254 nM), ELS detector, and TQ-MS equipped with APPI-source operating in positive ion mode.

LC-conditions: The column was BEH C18 1.7μ; 2.1×100 mm operating at 55° C. with 0.4 ml/min of a binary gradient consisting of water+0.1% formic acid (A) and acetonitrile+0.1 formic acid (B).

| Gradient: | 0.00 min | 5% B |
|---|---|---|
| | 0.60 min | 5% B |
| | 3.00 min | 95% B |
| | 5.00 min | 100% B |
| | 6.00 min | 100% B |
| | 6.10 min | 5% B |
| Total run time: | 6.10 min | |

The retention times (tR) are expressed in minutes based on UV-trace at 254 nm.

SFC

SFC were run on a Thar SFC-80 system consisting of sample manager, injector and collector, P-50 pumps for $CO_2$ and Co-Solvent and a Gilson UV-Visible detector (model 151, operating at 235 nm). A Lux Cellulose-2 (250×30 mm) column was used together with 25% of 0.5% DEA in ethanol as co-solvent with a total flow rate of 80 g/min at 160 bar. Samples were loaded at 50 mg/injection.

Prep. HPLC

Method 1:

Prep. HPLC were run on a Gilson GX-281 purification system consisting of sample manager, injector and collector, binary solvent pumps (model 334) and a Gilson UV-Visible detector (model 155, operating at 254 nm and 215 nm). A CHIRALPAK IC 5μ: 250×30 mm column was used eluted with hexane/ethanol (70:30) with a flow rate of 25 mL/min.

Method 2:

Prep. HPLC were run on a Gilson GX-281 purification system consisting of sample manager, injector and collector, binary solvent pumps (model 334) and a Gilson UV-Visible detector (model 155, operating at 254 nm and 215 nm). A CHIRALPAK IC 5μ: 250×30 mm column was used eluted with 0.1% DEA in hexane/ethanol (90:10) with a flow rate of 25 mL/min.

NMR $^1$H NMR spectra were recorded at 400 MHz on Varian-VNMRS-400 or Varian MR-400 instruments or at 600 MHz on a Bruker Avance AV-III-600 instrument. Chemical shift values are expressed in ppm-values relative to tetramethylsilane unless noted otherwise. The following abbreviations or their combinations are used for multiplicity of NMR signals: br=broad, d=doublet, m=multiplet, q=quartet, quint=quintet, s=singlet and t=triplet.

Intermediates

Intermediate X1

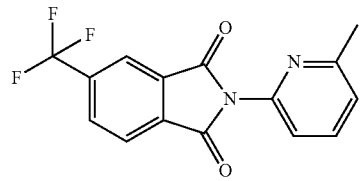 [SMILES: Cc1cccc(N2C(=O)c3ccc(C(F)(F)F)cc3C2=O)n1]

A solution of trifluoromethyl phthalic anhydride (1.5 g, 6.9 mmol) and 2-amino-6-picoline (0.75 g, 6.9 mmol) in acetic acid (10 mL) was heated at reflux for 5 h. After cooling to rt the reaction content was poured into ice cold water and stirred for 10 min during which time a solid precipitated. This solid was collected by filtration, and washed with diethyl ether (25 mL) to afford Intermediate X1 (1.0 g, 3.3 mmol, 48%) as an off-white solid.

$^1$H NMR (DMSO-d6, 400 MHz) δ: 8.32-8.30 (2H, m), 8.20-8.18 (1H, d, J=7.2 Hz), 7.96-7.92 (1H, t, J=7.6 Hz), 7.42-7.41 (1H, d, J=7.2 Hz). 7.37-7.35 (1H, d, J=8.0 Hz), 2.52 (3H, s).

Intermediates X2 to X18 were prepared from the corresponding phthalic anhydrides by a manner analogous to Intermediate X1.

| Intermediate Number | Structure | Condition variations and spectroscopic data |
|---|---|---|
| X2 | 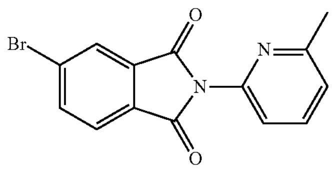 | 6-Methyl-pyridin-2-ylamine and triethylamine (3 eq.) in toluene.<br>$^1$H NMR (CDCl$_3$, 400 MHz) δ: 8.09 (1H, br s), 7.94-7.91 (1H, dd, J = 8.0, 2.0 Hz), 7.83-7.75 (2H, m), 7.26 (1H, s), 7.24-7.19 (1H, m), 2.62 (3H, s). |
| X3 | 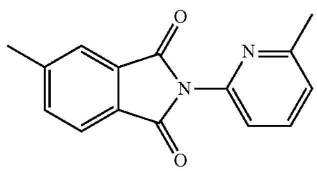 | 6-Methyl-pyridin-2-ylamine and triethylamine (3 eq.) in toluene.<br>$^1$H NMR (CDCl$_3$, 400 MHz) δ: 7.84-7.82 (1H, d, J = 7.6 Hz), 7.78-7.74 (2H, m), 7.58-7.56 (1H, d, J = 7.6 Hz), 7.23-7.19 (2H, m), 2.62 (3H, s), 2.54 (3H, s). |
| X4 | 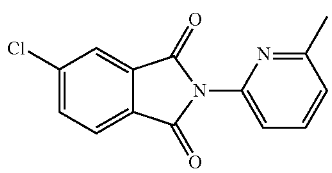 [SMILES: Cc1cccc(N2C(=O)c3ccc(Cl)cc3C2=O)n1] | 6-Methyl-pyridin-2-ylamine and triethylamine (3 eq.) in toluene.<br>$^1$H NMR (CDCl$_3$, 400 MHz) δ: 7.94-7.88 (2H, m), 7.81-7.73 (2H, m), 7.24-7.18 (2H, m), 2.62 (3H, s). |
| X5 | 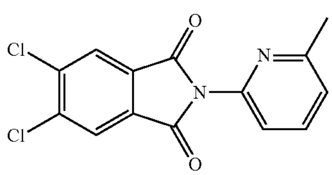 [SMILES: Cc1cccc(N2C(=O)c3cc(Cl)c(Cl)cc3C2=O)n1] | 6-Methyl-pyridin-2-ylamine in acetic acid.<br>$^1$H NMR (DMSO-d6, 400 MHz) δ: 8.30 (2H, s), 7.95-7.91 (1H, t, J = 8.0 Hz), 7.41-7.40 (1H, d, J = 7,.6 Hz), 7.35-7.33 (1H, d, J = 7.6 Hz), 2.51 (3H, s). |
| X6 | 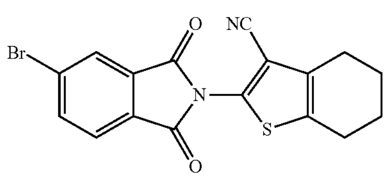 [SMILES: N#Cc1c(N2C(=O)c3ccc(Br)cc3C2=O)sc2c1CCCC2] | 2-amino-4,5,6,7-tetrahydrobenzo[b]thiophene-3-carbonitrile in acetic acid.<br>The crude product was used without purification. |
| X7 | 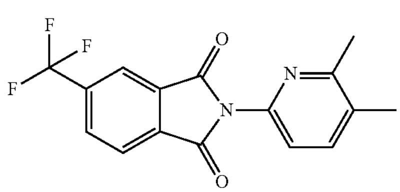 [SMILES: Cc1ccc(N2C(=O)c3ccc(C(F)(F)F)cc3C2=O)nc1C] | 2-amino-5,6-dimethylpyridine in acetic acid.<br>$^1$H NMR (DMSO-d6, 400 MHz) δ: 8.31 (1H, s), 8.29 (1H, s), 8.19-8.17 (1H, d, J = 8.4 Hz), 7.78-7.76 (1H, d, J = 8.0 Hz), 7.29-7.27 (1H, d, J = 8.0 Hz), 2.46 (3H, s), 2.33 (3H, s). |
| X8 | 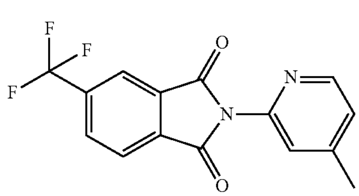 [SMILES: Cc1ccnc(N2C(=O)c3ccc(C(F)(F)F)cc3C2=O)c1] | 2-amino-4-picoline in acetic acid.<br>$^1$H NMR (CDCl$_3$, 400 MHz) δ: 8.55-8.54 (1H, d, J = 4.0 Hz), 8.23 (1H, s), 8.12-8.07 (2H, m), 7.26-7.25 (1H, d, J = 2.4 Hz), 7.23-7.21 (1H, d, J = 4.8 Hz), 2.47 (3H, s). |

-continued

| Intermediate Number | Structure | Condition variations and spectroscopic data |
|---|---|---|
| X9 | (5-trifluoromethyl-2-(2-methylpyridin-4-yl)isoindoline-1,3-dione) | 4-amino-2-picoline in acetic acid. The crude product was used without purification. |
| X10 | (5,6-dichloro-2-(4-methylpyridin-2-yl)isoindoline-1,3-dione) | 4-methyl pyridin-2-amine in acetic acid.<br>$^1$H NMR (CDCl$_3$, 400 MHz) δ: 8.53-8.52 (1H, d, J = 4.8 Hz), 8.04 (2H, s), 7.23 (1H, s), 7.21-7.20 (1H, d, J = 5.2 Hz), 2.45 (3H, s). |
| X11 | (5,6-dichloro-2-(5,6-dimethylpyridin-2-yl)isoindoline-1,3-dione) | 2-amino-5,6-dimethylpyridine in acetic acid.<br>$^1$H NMR (DMSO-d6, 400 MHz) δ: 8.29 (2H, s), 7.77-7.75 (1H, d, J = 8.0 Hz), 7.27-7.25 (1H, d, J = 7.6 Hz), 2.49 (3H, s), 2.32 (3H, s). |
| X12 | (5,6-dichloro-2-(2-methylpyridin-4-yl)isoindoline-1,3-dione) | 4-amino-2-picoline and triethylamine (3 eq.) in toluene.<br>$^1$H NMR (DMSO-d6, 400 MHz) δ: 8.61-8.60 (1H, d, J = 5.2 Hz), 8.33 (2H, s), 7.40 (1H, s), 7.36-7.34 (1H, d, J = 5.2 Hz), 2.54 (3H, s). |
| X13 | (5,6-dichloro-2-(2-methylpyrimidin-4-yl)isoindoline-1,3-dione) | 2-methylpyrimidin-4-amine and triethylamine (3 eq.) in toluene.<br>$^1$H NMR (DMSO-d6, 400 MHz) δ: 8.94-8.92 (1H, d, J = 5.2 Hz), 8.35 (2H, s), 7.48-7.47 (1H, d, J = 5.2 Hz), 2.68 (3H, s). |
| X15 | (5,6-dimethyl-2-(6-methylpyridin-2-yl)isoindoline-1,3-dione) | 2-amino-6-methylpyridine in acetonitrile. 170° C. (microwave) for 10 min. LCMS Method A: tR = 0.65 min, m/z = 267.2 [M + H]$^+$ |
| X16 | (5-trifluoromethyl-2-(3-chloro-5-(trifluoromethyl)pyridin-2-yl)isoindoline-1,3-dione) | 3-chloro-5-(trifluoromethyl)pyridin-2-amine and triethylamine (3 eq.) in toluene.<br>$^1$H NMR (DMSO-d6, 400 MHz) δ: 9.17-9.17 (1H, d, J = 0.8 Hz), 8.93-8.92 (1H, d, J = 1.6 Hz), 8.46 (1H, s), 8.39-8.37 (1H, d, J = 8.0 Hz), 8.31-8.29 (1H, d, J = 8.0 Hz). |
| X17 | (5-trifluoromethyl-2-(4-methylpyrimidin-2-yl)isoindoline-1,3-dione) | 4-methylpyrimidin-2-amine in acetic acid.<br>$^1$H NMR (DMSO-d6, 400 MHz) δ: 8.89-8.88 (1H, d, J = 4.8 Hz), 8.35-8.32 (2H, m), 8.23-8.21 (1H, d, J = 8.0 Hz), 7.60-7.59 (1H, d, J = 4.8 Hz), 2.58 (3H, s). |

| Intermediate Number | Structure | Condition variations and spectroscopic data |
|---|---|---|
| X18 | 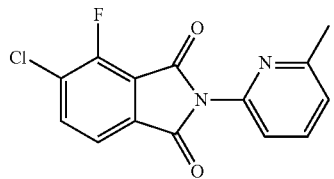 [SMILES: Cc1cccc(N2C(=O)c3ccc(Cl)c(F)c3C2=O)n1] | 5,6-dimethylpyrazin-2-amine in acetic acid.<br>$^1$H NMR (DMSO-d6, 400 MHz) δ: 8.51 (1H, s), 83.6 (1H, s), 8.34-8.32 (1H, d, J = 8.0 Hz), 8.22-8.20 (1H, d, J = 8.0 Hz), 2.58 (3H, s), 2.55 (3H, s). |

Intermediate X14

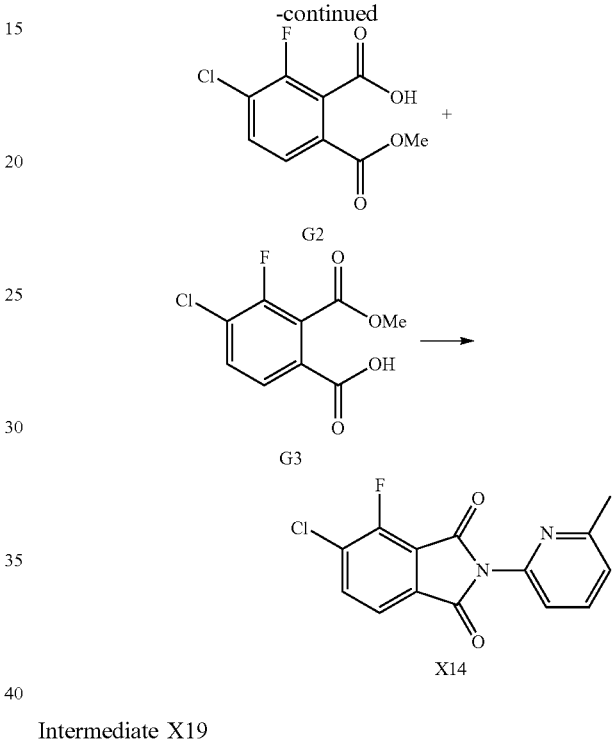

Synthesised according to Scheme 10.

Fuming Sulfuric Acid (30%, 4 mL) was added to 3-chloro-2-fluoro-6-(trifluoromethyl)benzoic acid (G1, 0.294 g, 1.21 mmol) and the resulting brown solution heated to 150° C. for 2 h. After cooling to 0° C., cold MeOH (5 ml) was added and the mixture stirred at rt for 0.5 h. Purification by flash column chromatography (solvent gradient 0-100% EtOAc in heptane over 20 mins) afforded an inseparable ca. 1:1 mixture of 4-chloro-3-fluoro-phthalic acid 1-methyl ester and 3-Chloro-2-fluoro-phthalic acid 1-methyl ester (G2+G3, 0.210 g, 0.91 mmol, 75%).

$^1$H NMR (ca. 1:1 mixture of isomers, CDCl$_3$, 600 MHz) δ: 10.67 (2H, br s), 7.85-7.81 (1H, d, J=7.8 Hz), 7.74-7.71 (1H, d, J=8.6 Hz), 7.57-7.50 (2H, m), 3.96 (3H, s), 3.91 (3H, s).

Phosphoryl chloride (0.060 mL, 0.64 mmol) was added to a solution of 4-Chloro-3-fluoro-phthalic acid 1-methyl ester (0.050 g, 0.21 mmol), 3-Chloro-2-fluoro-phthalic acid 1-methyl ester (0.050 g, 0.21 mmol) and 2-amino-6-methylpyridine (0.046 g, 0.43 mmol) in pyridine (4 mL) at 0° C. The reaction was allowed to warm to rt and stirred for 1 h. Methanol (2 mL) was added and solvents were removed in vacuo to give a crude orange product which was purified by flash column chromatography (solvent gradient 0-100% EtOAc in heptane over 16 min then 5 mins at 100% EtOAc). Intermediate X15 (0.0198 g, 0.068 mmol, 33%) was isolated as a white solid.

$^1$H NMR (DMSO-d6, 600 MHz) δ: 7.81-7.78 (1H, dd, J=7.6, 8.7 Hz), 7.72-7.70 (1H, dd, J=1.1, 8.5 Hz), 7.56-7.54 (1H, d, J=8.7 Hz), 7.45-7.41 (1H, dd, J=7.1, 8.4 Hz), 6.89-6.86 (1H, d, J=7.6 Hz), 2.60 (3H, s).

Scheme 10

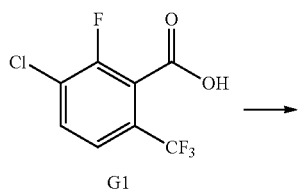

Intermediate X19

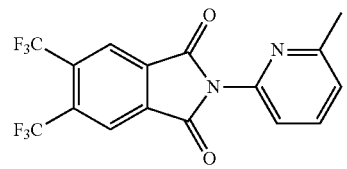 [SMILES: Cc1cccc(N2C(=O)c3cc(C(F)(F)F)c(C(F)(F)F)cc3C2=O)n1]

Synthesised according to Scheme 11.

To a solution of dimethyl 4,5-diiodophthalate (H1, 4.0 g, 8.96 mmol) in DMF (40.0 mL) was added CuI (5.1 g, 26.9 mmol), and FSO$_2$CF$_2$CO$_2$Me (13.77 g, 71.74 mmol) and the mixture was stirred at 80° C. for 18 h. The mixture was then diluted with ice cold water and extracted with EtOAc (100 mL), dried over anhydrous Na$_2$SO$_4$ and concentrated under reduced pressure to afford intermedidate R2 (1.8 g, 61%) as white solid.

$^1$H NMR (DMSO-d6, 400 MHz) δ: 8.18 (2H, s), 3.95 (6H, s).

Trimethylaluminium solution (0.45 mL, 0.909 mmol, 2.0 M toluene) was added to a solution of intermedidate R2 (150 mg, 0.45 mmol) and 6-methylpyridin-2-amine (53.9 mg, 0.49 mmol) in toluene (2.0 mL) and the reaction was stirred at 110° C. for 3 h. The solution was then partitioned between EtOAc and water, the organic layer was separated and solvents were removed under reduced pressure. Purification by column chromatography afforded intermediate X19 (100 mg, 59%) as pale yellow solid.

¹H NMR (DMSO-d6, 400 MHz) δ: 8.45 (2H, s), 7.84-7.80 (1H, t, J=7.6 Hz), 7.31-7.29 (1H, d, J=7.6 Hz), 7.23-7.21 (1H, d, J=8.0 Hz), 2.64 (3H, s).

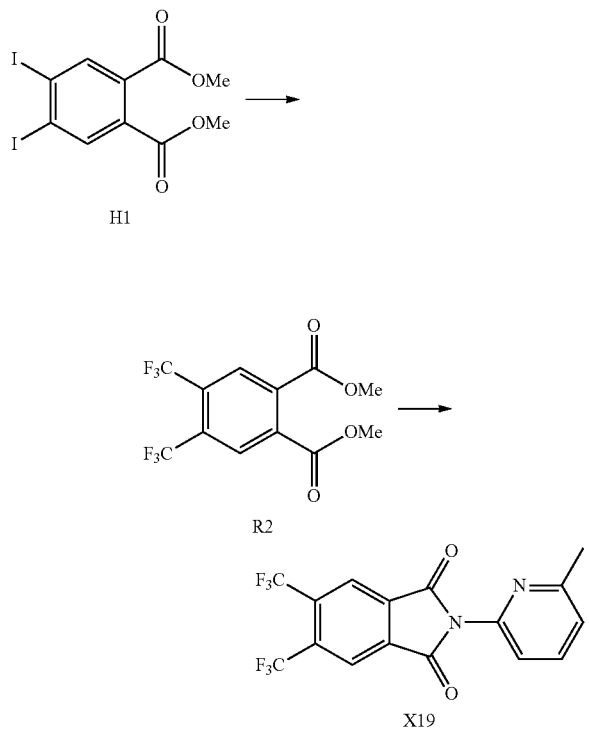

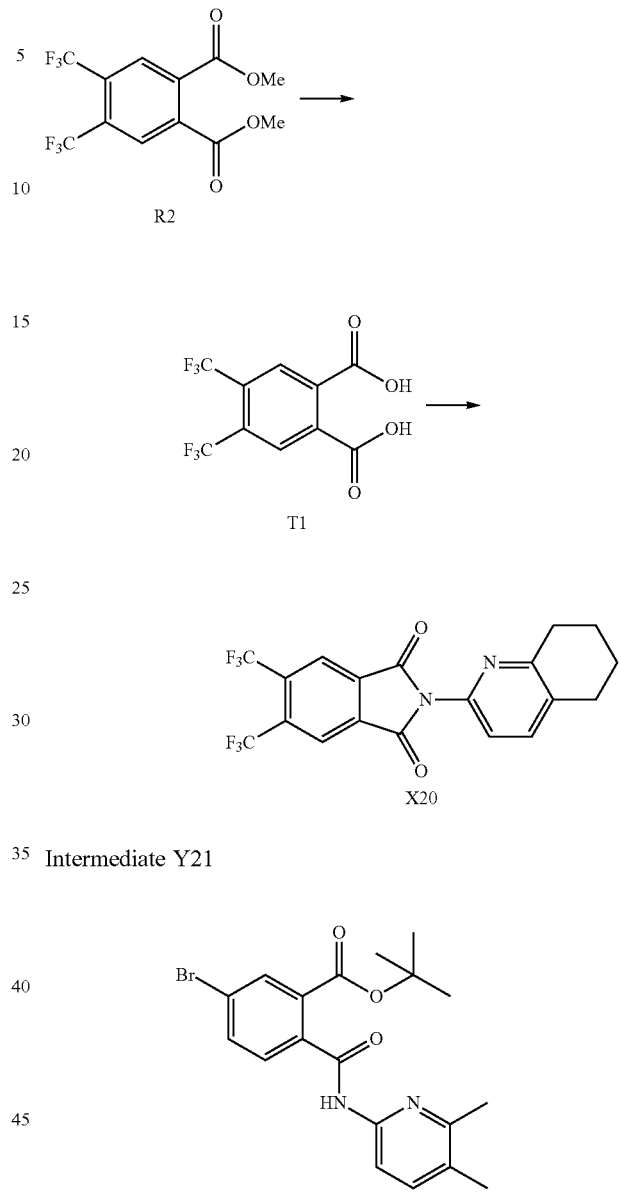

Intermediate Y21

Intermediate X20

Synthesised according to scheme 12

LiOH.H₂O (50 mg, 1.212 mmol) was added to a solution of intermedidate R2 (200 mg, 0.606 mmol) in THF/H₂O (1:1, 6.0 mL) and the reaction mixture was stirred at room temperature for 16 h. THF was then removed under reduced pressure, the crude product was acidified with 1N HCl and the resulting solid was filtered and dried to afford intermedidate T1 (140 mg, 77%) as a white solid.

¹H NMR (DMSO-d6, 400 MHz) δ: 13.50 (2H, br), 8.29 (2H, s).

HATU (283 mg, 0.746 mmol) and DIPEA (0.27 mL, 1.49 mmol) were added to a solution of intermedidate T1 (150 mg, 0.496 mmol) and 5,6,7,8-tetrahydroquinolin-2-amine (73 mg, 0.496 mmol) in DCM (5.0 mL) at 0° C. The reaction mixture was then stirred at rt for 18 h before being quenched with water (50 mL), extracted EtOAc (50 mL), dried over anhydrous Na₂SO₄ and concentrated under reduced pressure. The crude product was purified by column chromatography to afford intermediate X20 (85 mg, 41%) as a pale yellow solid.

¹H NMR (DMSO-d6, 400 MHz) δ: 8.53 (2H, s), 7.74-7.72 (1H, d, J=8.4 Hz), 7.28-7.26 (1H, d, J=8.0 Hz), 2.84-2.83 (4H, m), 1.86-1.79 (4H, m).

DIPEA (0.257 g, 1.99 mmol) was added to a suspension of intermediate Z48 (0.20 g, 0.66 mmol), 5,6-dimethylpyridin-2-amine (0.097 g, 0.80 mmol) and HATU (0.38 g, 1.00 mmol) in DCM (15 mL) at 0° C. The reaction was allowed to warm to rt and was stirred for 18 h before being quenched with water, extracted with DCM (2×40 mL), washed with brine and dried over anhydrous Na₂SO₄. Solvents were removed in vacuo and the crude product was purified by flash column chromatography (10% ethyl acetate in hexane) to afford intermediate Y21 (0.091 g, 0.22 mmol, 34%) as a white solid.

¹H NMR (DMSO-d6, 400 MHz) δ: 10.86 (1H, s), 7.95-7.93 (1H, d, J=8.4 Hz), 7.89-7.88 (1H, d, J=2.0 Hz), 7.81-7.79 (1H, dd, J=8.4 Hz, 2.0 Hz), 7.56-7.54 (1H, d, J=8.4 Hz), 7.47-7.45 (1H, d, J=8.0 Hz), 2.35 (3H, s), 2.22 (3H, s), 1.36 (9H, s).

The following intermediates Y22-42, Y44-Y46 and Y48 were prepared by a manner analogous to Intermediate Y21 from intermediates Z49-Z51.

| Intermediate Number | Structure | Condition variations and spectroscopic data |
|---|---|---|
| Y22 | 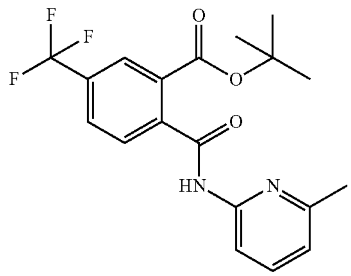 | From Intermediate Z49<br>Synthesised using POCl₃ in pyridine.<br>¹H NMR (DMSO-d6, 400 MHz) δ: 11.09 (1H, s), 8.05-8.00 (3H, m), 7.76-7.72 (2H, m), 7.03-7.01 (1H, d, J = 7.6 Hz), 2.45 (3H, s), 1.37 (9H, s). |
| Y23 | 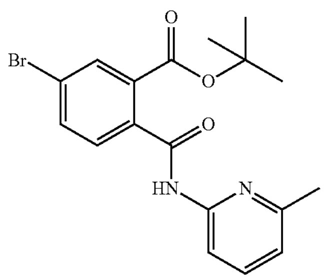 [SMILES: Cc1ccc(NC(=O)c2ccc(Br)cc2C(=O)OC(C)(C)C)nc1C] | From Intermediate Z48<br>Synthesised using POCl₃ in pyridine.<br>¹H NMR (CDCl₃, 400 MHz) δ: 8.15-8.13 (1H, d, J = 8.0 Hz), 8.08 (1H, s) 8.05-8.04 (1H, d, J = 2.0 Hz), 7.68-7.63 (2H, m), 7.41-7.39 (1H, d, J = 8.0 Hz), 6.94-6.92 (1H, d, J = 7.6 Hz), 2.43 (3H, s), 1.43 (9H, s). |
| Y24 | 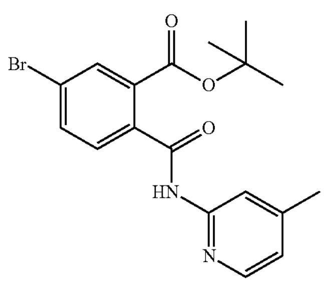 | From Intermediate Z48<br>Synthesised using POCl₃ pyridine.<br>¹H NMR (DMSO-d6, 400 MHz): δ: 10.92 (1H, s), 8.19-8.18 (1H, d, J = 4.8 Hz), 8.05 (1H, s), 7.92-7.91 (1H, d, J = 2.0 Hz), 7.84-7.82 (1H, dd, J = 2.0, 8.0 Hz), 7.48-7.46 (1H, d, J = 8.0 Hz), 6.99-6.98 (1H, d, J = 4.8), 2.35 (3H, s), 1.37 (9H, s). |
| Y25 | 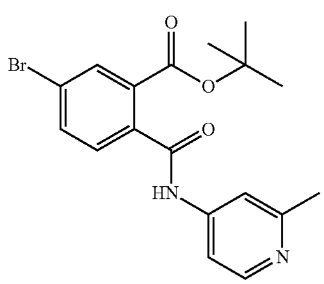 | From Intermediate Z48<br>Synthesised using HATU and DIPEA.<br>Compound was used directly in the next step without purification. |
| Y26 | 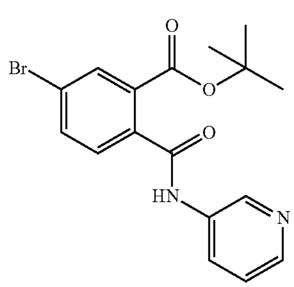 [SMILES: CC(C)(C)OC(=O)c1cc(Br)ccc1C(=O)Nc1cccnc1] | From Intermediate Z48<br>Synthesised using HATU and DIPEA.<br>¹H NMR (DMSO-d6, 400 MHz) δ: 10.69 (1H, s), 8.86-8.85 (1H, d, J = 1.6 Hz), 8.31-8.30 (1H, d, J = 4.0 Hz), 8.17-8.15 (1H, d, J = 8.0 Hz), 7.97-7.96 (1H, d, J = 1.6 Hz), 7.91-7.89 (1H, dd, J = 8.0, 1.6 Hz), 7.58-7.56 (1H, d, J = 8.0 Hz), 7.41-7.38 (1H, dd, J = 8.0, 4.4 Hz), 1.374 (9H, s). |

| Intermediate Number | Structure | Condition variations and spectroscopic data |
|---|---|---|
| Y27 | 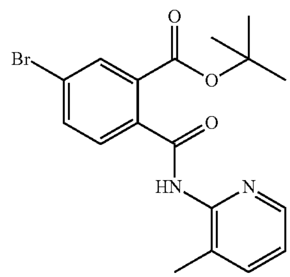 [SMILES: Cc1cccnc1NC(=O)c1ccc(Br)cc1C(=O)OC(C)(C)C] | From Intermediate Z48<br>Synthesised using POCl₃ in pyridine.<br>¹H NMR (DMSO-d6, 400 MHz) δ: 10.56 (1H, s), 8.26-8.25 (1H, d, J = 3.6 Hz), 7.86-7.83 (2H, m), 7.70-7.69 (1H, d, J = 7.2 Hz), 7.59-7.57 (1H, d, J = 8.0 Hz), 7.23-7.20 (1H, dd, J = 4.8, 7.2 Hz), 2.26 (3H, s), 1.45 (9H, s). |
| Y28 | 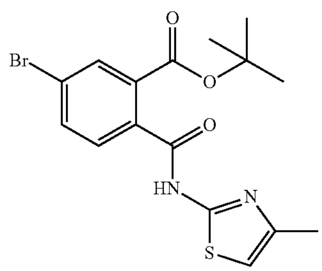 [SMILES: Cc1csc(NC(=O)c2ccc(Br)cc2C(=O)OC(C)(C)C)n1] | From Intermediate Z48<br>Synthesised using HATU and DIPEA.<br>¹H NMR (DMSO-d6, 400 MHz) δ: 12.59 (1H, s), 7.93-7.92 (1H, d, J = 2.4 Hz), 7.89-7.85 (1H, dd, J = 10.8, 2.8 Hz), 7.55-7.52 (1H, d, J = 10.8 Hz), 6.82 (1H, s), 2.28-2.28 (3H, d, J = 1.2 Hz), 1.37 (9H, s). |
| Y29 | 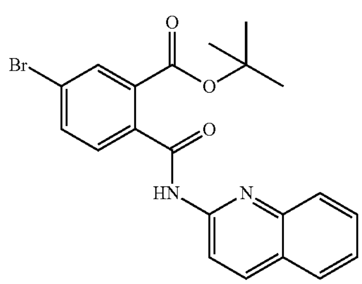 [SMILES: CC(C)(C)OC(=O)c1cc(Br)ccc1C(=O)Nc1ccc2ccccc2n1] | From Intermediate Z48<br>Synthesised using POCl₃ in pyridine.<br>¹H NMR (CDCl₃, 400 MHz) δ: 8.74 (1H, s), 8.58-8.56 (1H, d, J = 8.8 Hz), 8.24-8.22 (1H, d, J = 8.8 Hz), 8.00-7.99 (1H, d, J = 2.0 Hz), 7.81-7.79 (1H, d, J = 8.0 Hz), 7.75-7.73 (1H, d, J = 8.8 Hz), 7.66-7.61 (2H, m), 7.49-7.41 (2H, m), 1.45 (9H, s). |
| Y30 | 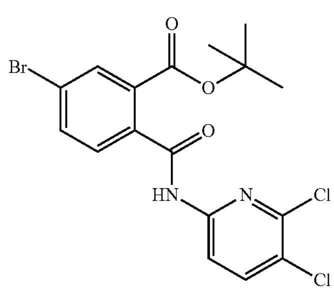 [SMILES: CC(C)(C)OC(=O)c1cc(Br)ccc1C(=O)Nc1ccc(Cl)c(Cl)n1] | From Intermediate Z48<br>Synthesised using POCl₃ in pyridine.<br>¹H NMR (CDCl₃, 400 MHz) δ: 8.29-8.27 (1H, d, J = 8.8 Hz), 8.14 (1H, s), 8.06-8.05 (1H, d, J = 2.0 Hz), 7.83-7.80 (1H, d, J = 8.8 Hz), 7.71-7.69 (1H, dd, J = 1.6, 7.6 Hz), 7.40-7.38 (1H, d, J = 8.4), 1.47 (9H, s). |
| Y31 | 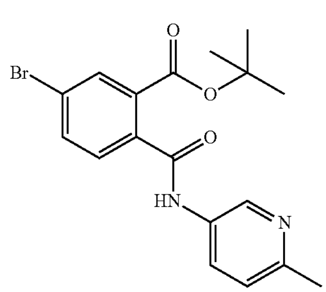 | From Intermediate Z48<br>Synthesised using HATU and DIPEA.<br>¹H NMR (CDCl₃, 400 MHz) δ: 8.51-8.50 (1H, d, J = 3.2 Hz), 8.21-8.18 (1H, dd, J = 3.2, 11.2 Hz), 7.99-7.98 (1H, d, J = 2.0 Hz), 7.90 (1H, s), 7.70-7.67 (1H, dd, J = 2.4, 11.2 Hz), 7.48-7.45 (1H, d, J = 10.8 Hz), 7.18-7.16 (1H, d, J = 11.2 Hz), 2.54 (3H, s), 1.48 (9H, s). |

-continued

| Intermediate Number | Structure | Condition variations and spectroscopic data |
|---|---|---|
| Y32 | 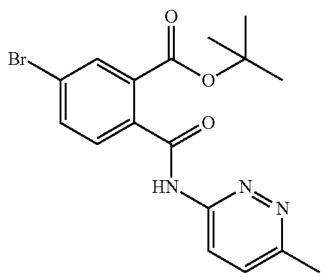 | From Intermediate Z48<br>Synthesised using HATU and DIPEA.<br>LCMS Method C: tR = 3.24 min, m/z = 392.08 [M + H]⁺ |
| Y33 | 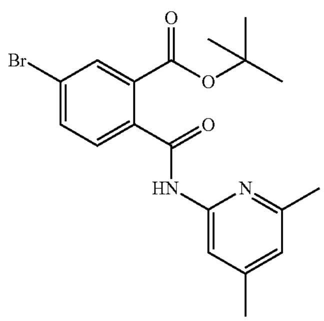 [SMILES: Cc1cc(C)nc(NC(=O)c2ccc(Br)cc2C(=O)OC(C)(C)C)c1] | From Intermediate Z48<br>Synthesised using HATU and DIPEA.<br>¹H NMR (CDCl₃, 400 MHz) δ: 8.19 (1H, s), 8.04-8.03 (1H, d, J = 2.0 Hz), 7.99 (1H, s), 7.66-7.63 (1H, dd, J = 2.0, 8.4 Hz), 7.39-7.37 (1H, d, J = 8.0 Hz), 6.75 (1H, s), 2.36 (3H, s), 2.35 (3H, s), 1.46 (9H, s). |
| Y34 | 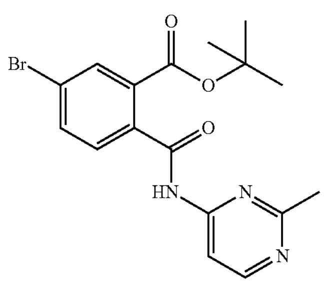 | From Intermediate Z48<br>Synthesised using HATU and DIPEA.<br>¹H NMR (CDCl₃, 400 MHz) δ: 8.61-8.59 (1H, d, J = 6.0 Hz), 8.17 (1H, s), 8.10-8.08 (1H, d, J = 5.6 Hz), 8.07-8.06 (1H, d, J = 1.6 Hz), 7.72-7.69 (1H, dd, J = 2.0, 8.4 Hz), 7.41-7.39 (1H, d, J = 8.0 Hz), 2.61 (3H, s) 1.47 (9H, s). |
| Y35 | 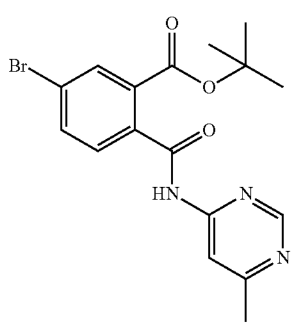 [SMILES: Cc1cc(NC(=O)c2ccc(Br)cc2C(=O)OC(C)(C)C)ncn1] | From Intermediate Z48<br>Synthesised using POCl₃ in pyridine.<br>¹H NMR (DMSO-d6, 400 MHz) δ: 11.37 (1H, s), 8.76 (1H, s), 8.06 (1H, s), 7.96-7.95 (1H, d, J = 6.0 Hz, 7.88-7.85 (1H, dd, J = 2.0, 8.4 Hz), 7.51-7.49 (1H, d, J = 8.0 Hz), 2.47 (3H, s), 1.37 (9H, s). |
| Y36 | 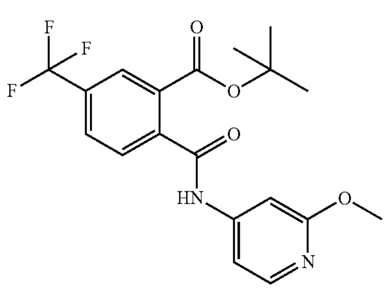 [SMILES: COc1cc(NC(=O)c2ccc(C(F)(F)F)cc2C(=O)OC(C)(C)C)ccn1] | From Intermediate Z49<br>Synthesised using POCl₃ in pyridine.<br>¹H NMR (DMSO-d6, 400 MHz) δ: 10.89 (1H, s), 8.12 (1H, s), 8.09-8.07 (2H, d, J = 5.6 Hz), 7.84-7.82 (1H, d, J = 8.0 Hz), 7.22 (1H, s), 7.20-7.18 (1H, dd, J = 1.2, 5.6 Hz), 3.84 (3H, s), 1.38 (9H, s). |

-continued

| Intermediate Number | Structure | Condition variations and spectroscopic data |
|---|---|---|
| Y37 | 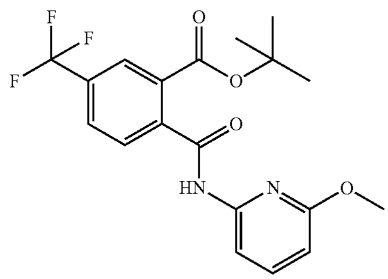 [SMILES: COc1cccc(NC(=O)c2ccc(C(F)(F)F)cc2C(=O)OC(C)(C)C)n1] | From Intermediate Z49<br>Synthesised using POCl₃ in pyridine.<br>¹H NMR (DMSO-d6, 400 MHz, TMS) δ: 10.95 (1H, s), 8.08 (1H, s), 8.03-8.01 (1H, d, J = 8.0 Hz), 7.81-7.73 (3H, m), 6.58-6.56 (1H, d, J = 8.0 Hz), 3.81 (3H, s), 1.38 (9H, s). |
| Y38 | 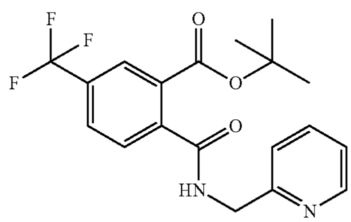 [SMILES: CC(C)(C)OC(=O)c1cc(C(F)(F)F)ccc1C(=O)NCc1ccccn1] | From Intermediate Z49<br>Synthesised using propylphosphonic anhydride and DIPEA.<br>¹H NMR (DMSO-d6, 400 MHz) δ: 9.16-9.13 (1H, t, J = 5.8 Hz), 8.53-8.51 (1H, d, J = 4.8 Hz), 8.01-7.99 (2H, d, J = 8.4 Hz), 7-81-7.75 (2H, m), 7.46-7.44 (1H, d, J = 8.0 Hz), 7.30-7.27 (1H, q, J = 4.0 Hz), 4.56-4.55 (2H, d, J = 6.0 Hz), 1.47 (9H, s). |
| Y39 | 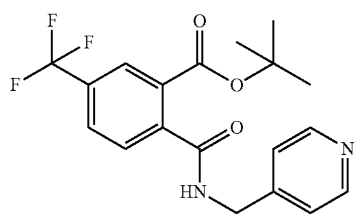 [SMILES: CC(C)(C)OC(=O)c1cc(C(F)(F)F)ccc1C(=O)NCc1ccncc1] | From Intermediate Z49<br>Synthesised using propylphosphonic anhydride and DIPEA.<br>¹H NMR (DMSO-d6, 400 MHz) δ: 9.18-9.15 (1H, t, J = 6.4 Hz), 8.53-8.52 (2H, d, J = 5.2 Hz), 8.02-8.00 (2H, m), 7.78-7.76 (1H, d, J = 8.4 Hz), 7.39-7.38 (2H, d, J = 5.6 Hz), 4.50-4.49 (2H, d, J = 6.4 Hz), 1.47 (9H, s). |
| Y40 | 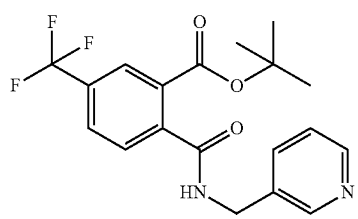 [SMILES: CC(C)(C)OC(=O)c1cc(C(F)(F)F)ccc1C(=O)NCc1cccnc1] | From Intermediate Z49<br>Synthesised using propylphosphonic anhydride and DIPEA.<br>¹H NMR (DMSO-d6, 400 MHz) δ: 9.14-9.12 (1H, t, J = 5.6 Hz), 8.59 (1H, s), 8.48-8.47 (1H, d, J = 4.4 Hz), 7.99-7.97 (2H, d, J = 6.8 Hz), 7.79-7.77 (1H, d, J = 8.0 Hz), 7.72-7.70 (1H, d, J = 8.4 Hz), 7.39-7.36 (1H, q, J = 4.2 Hz), 4.50-4.48 (2H, d, J = 6.0 Hz), 1.46 (9H, s). |
| Y41 | 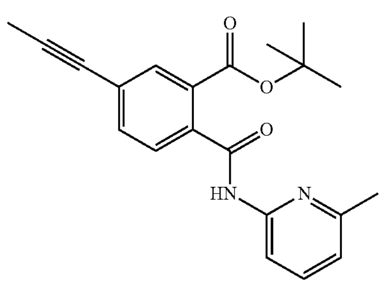 [SMILES: CC#Cc1ccc(C(=O)Nc2cccc(C)n2)c(C(=O)OC(C)(C)C)c1] | From Intermediate Z50<br>Synthesised using POCl₃ in pyridine.<br>¹H NMR (CDCl₃, 400 MHz, TMS) δ: 8.16-8.14 (1H, d, J = 7.6 Hz), 8.09-8.06 (1H, d, J = 11.2 Hz), 7.90 (1H, s), 7.66-7.62 (1H, t, J = 7.8 Hz), 7.53-7.51 (1H, dd, J = 1.6, 8.0 Hz), 7.45-7.43 (1H, d, J = 8.0 Hz), 6.93-6.91 (1H, d, J = 7.6 Hz), 2.43 (3H, s), 2.07 (3H, s), 1.45 (9H, s). |
| Y42 | 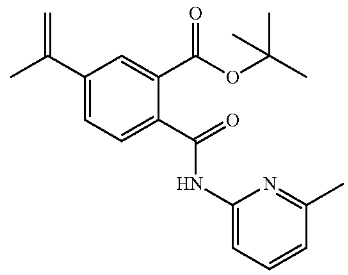 [SMILES: C=C(C)c1ccc(C(=O)Nc2cccc(C)n2)c(C(=O)OC(C)(C)C)c1] | From Intermediate Z51<br>Synthesised using HATU and DIPEA.<br>¹H NMR (CDCl₃, 400 MHz) δ: 8.19-8.17 (1H, d, J = 8.0 Hz), 8.07 (1H, s), 8.00-7.99 (1H, d, J = 1.6 Hz), 7.66-7.60 (2H, m), 7.50-7.48 (1H, d, J = 8.0 Hz), 6.93-6.91 (1H, d, J = 7.6 Hz), 5.47 (1H, s), 5.21 (1H, s), 2.44 (3H, s), 2.18 (3H, s), 1.45 (9H, s). |

| Intermediate Number | Structure | Condition variations and spectroscopic data |
|---|---|---|
| Y44 | 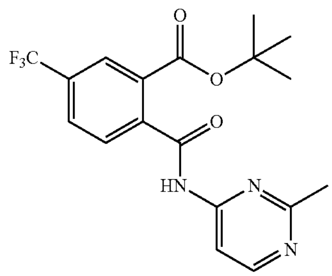 [SMILES: Cc1nccc(NC(=O)c2ccc(C(F)(F)F)cc2C(=O)OC(C)(C)C)n1] | From Intermediate Z49<br>Synthesised using NMI and methanesul-fonylchloride in DCM.<br>$^1$H NMR (DMSO-d6, 400 MHz) δ: 11.55 (1H, s), 8.65-8.63 (1H, d, J = 5.6 Hz), 8.09 (1H, s), 8.06-7.98 (2H, m), 7.80-7.78 (1H, d, J = 7.6 Hz), 2.52 (3H, s), 1.38 (9H, s). |
| Y45 | 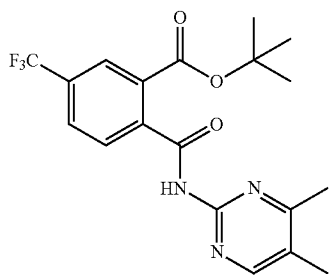 [SMILES: Cc1cnc(NC(=O)c2ccc(C(F)(F)F)cc2C(=O)OC(C)(C)C)nc1C] | From Intermediate Z49<br>Synthesised using NMI and methanesul-fonylchloride in DCM.<br>$^1$H NMR (DMSO-d6, 400 MHz) δ: 11.05 (1H, s), 8.26 (1H, s), 7.99-7.97 (1H, d, J = 8.4 Hz), 7.91-7.89 (1H, d, J = 8.0 Hz), 7.77 (1H, s), 2.28 (3H, br s), 2.13 (3H, s), 1.38 (9H, s). |
| Y46 | 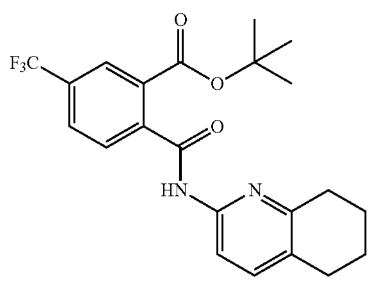 [SMILES: CC(C)(C)OC(=O)c1cc(C(F)(F)F)ccc1C(=O)Nc1ccc2c(n1)CCCC2] | From Intermediate Z49<br>Synthesised using HATU and DIPEA.<br>$^1$H NMR (DMSO-d6, 400 MHz) δ: 8.21 (1H, br s), 8.18 (1H, s), 8.09-8.07 (1H, d, J = 8.4 Hz), 7.79-7.77 (1H, d, J = 9.2 Hz), 7.64-7.62 (1H, d, J = 8.0 Hz), 7.44-7.42 (1H, d, J = 8.0 Hz), 2.75-2.71 (4H, q, J = 6.0 Hz), 1.88-1.76 (4H, m), 1.47 (9H, s). |
| Y48 | 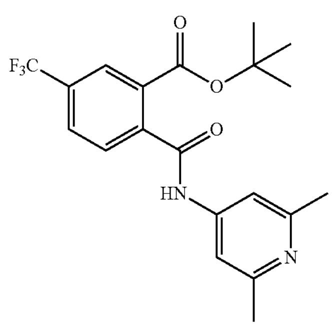 [SMILES: Cc1cc(NC(=O)c2ccc(C(F)(F)F)cc2C(=O)OC(C)(C)C)cc(C)n1] | From Intermediate Z49<br>Synthesised using HATU and DIPEA.<br>$^1$H NMR (DMSO-d6, 400 MHz) δ: 10.78 (1H, s), 8.11-8.06 (2H, m), 7.80-7.78 (1H, d), 7.34 (2H, s), 2.39 (6H, s), 1.38 (9H, s). |
| Y49 | 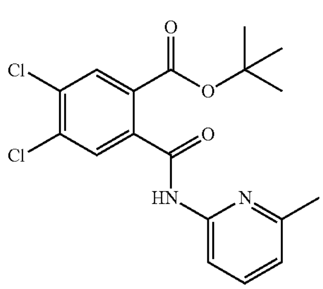 [SMILES: Cc1cccc(NC(=O)c2cc(Cl)c(Cl)cc2C(=O)OC(C)(C)C)n1] | From Intermediate Z52<br>Synthesised using HATU and DIPEA.<br>$^1$H NMR (DMSO-d6, 400 MHz) δ: 11.03 (1H, s), 8.02-8.0 (1H, d, J = 8.0 Hz), 7.96 (1H, s), 7.86 (1H, s), 7.75-7.71 (1H, t, J = 7.6 Hz), 7.03-7.01 (1H, d, J = 7.6 Hz), 2.49 (3H, s), 1.36 (9H, s). |

-continued

| Intermediate Number | Structure | Condition variations and spectroscopic data |
|---|---|---|
| Y50 | 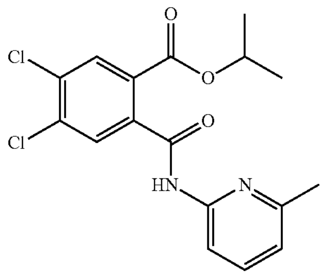 [SMILES: Cc1cccc(NC(=O)c2cc(Cl)c(Cl)cc2C(=O)OC(C)C)n1] | From Intermediate Z53<br>Synthesised using POCl₃ in pyridine.<br>$^1$H NMR (DMSO-d6, 400 MHz) δ: 11.01 (1H, s), 8.01 (1H, s), 7.98 (1H, s), 7.90 (1H, s), 7.75-7.71 (1H, t, J = 8.0 Hz), 7.03-7.01 (1H, d, J = 7.6 Hz), 5.05-4.99 (1H, m), 2.41 (3H, s), 1.14 (6H, d, J = 4.0 Hz). |
| Y51 | 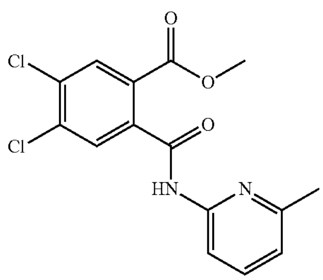 [SMILES: COC(=O)c1cc(Cl)c(Cl)cc1C(=O)Nc1cccc(C)n1] | From Intermediate Z54<br>Synthesised using POCl₃ in pyridine.<br>$^1$H NMR (CDCl₃, 400 MHz) δ: 8.21 (1H, s), 8.11-8.09 (1H, d, J = 7.6 Hz), 8.05 (1H s), 7.67-7.63 (2H, m), 6.95-6.93 (1H, d, J = 7.6 Hz), 3.86 (3H, s), 2.42 (3H, s). |
| Y52 | 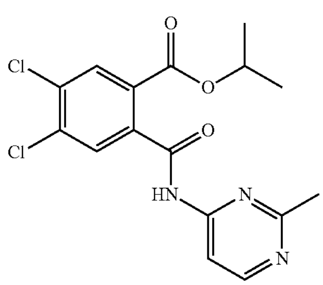 [SMILES: Cc1nccc(NC(=O)c2cc(Cl)c(Cl)cc2C(=O)OC(C)C)n1] | From Intermediate Z53<br>Synthesised using propylphosphonic anhydride and DIPEA.<br>$^1$H NMR (DMSO-d₆, 400 MHz) δ: 11.45 (1H, s), 8.63-8.62 (1H, d, J = 5.6 Hz), 8.04 (1H, s), 7.96 (2H, s), 5.06-5.00 (1H, m), 2.52 (3H, s), 1.15 (6H, d, J = 4.0 Hz). |
| Y53 | 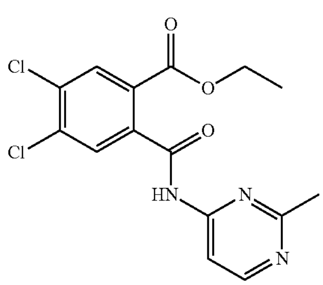 [SMILES: CCOC(=O)c1cc(Cl)c(Cl)cc1C(=O)Nc1ccnc(C)n1] | From Intermediate Z55<br>Synthesised using propylphosphonic anhydride and DIPEA.<br>$^1$H NMR (DMSO-d₆, 400 MHz) δ: 11.44 (1H, s), 8.63-8.61 (1H, d, J = 5.6 Hz), 8.06 (1H, s), 7.97 (1H, s), 7.96-7.95 (1H, d, J = 5.6 Hz), 4.24-4.18 (2H, q, J = 7.2 Hz), 2.52 (3H, s), 1.16-1.13 (3H, t, J = 7.0 Hz). |

Intermediate Y43

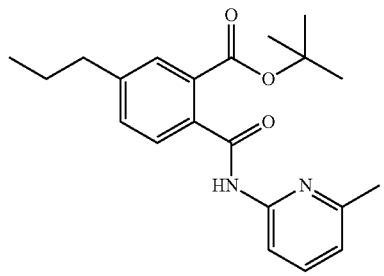 [SMILES: CCCc1ccc(C(=O)Nc2cccc(C)n2)c(C(=O)OC(C)(C)C)c1]

To a solution of Intermediate Y41 (250 mg, 0.71 mmol) in EtOH (2.5 mL) was added 10% palladium on carbon (250 mg) at rt. The reaction mixture was allowed to stir for 8 h at rt under $H_2$ (balloon pressure). After completion of the reaction (monitored by TLC), the reaction mixture was filtered through celite and the filtrate was concentrated under reduced pressure to afford Intermediate Y43 (100 mg, 0.28 mmol, 40%).

$^1$H NMR (CDCl$_3$, 400 MHz) δ: 8.18-8.16 (1H, d, J=7.6 Hz), 8.06 (1H, br s), 7.72-7.71 (1H, d, J=1.6 Hz), 7.65-7.61 (1H, t, J=8.0 Hz), 7.45-7.43 (1H, d, J=7.6 Hz), 7.35-7.32 (1H, dd, J=1.6, 8.0 Hz), 6.92-6.90 (1H, d, J=7.6 Hz), 2.67-2.63 (2H, t, J=7.6 Hz), 2.43 (3H, s), 1.72-1.64 (2H, m), 1.57 (9H, s), 0.96-0.93 (3H, t, J=7.2 Hz).

The following intermediate, Y47, was prepared by a manner analogous to Intermediate Y43.

Intermediate Y47

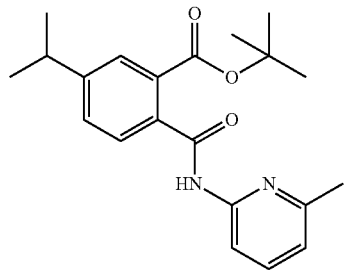 [SMILES: Cc1cccc(NC(=O)c2ccc(C(C)C)cc2C(=O)OC(C)(C)C)n1]

Synthesised from intermediate Y42 in MeOH under an atmosphere of $H_2$ (60 psi).

LCMS Method D: tR=3.47 min, m/z=355.10 [M+H]$^+$

Intermediate Z48

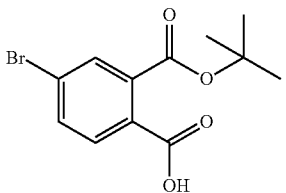 [SMILES: CC(C)(C)OC(=O)c1cc(Br)ccc1C(=O)O]

DMAP (10.8 g, 88 mmol) was added to a solution of 4-bromophthalic anhydride (20 g, 88 mmol) and t-BuOH (8.4 mL, 88 mmol) in DCM (200 mL) at rt. After stirring for 2 h the reaction mixture was diluted with DCM (200 mL) and washed with 2M HCl (150 mL×2). Solvents were removed under reduced pressure to afford a white solid containing intermediate Z48 and its isomer. This mixture was separated by SFC to afford Intermediate Z48 (3.0 g, 10 mmol, 12%) as a white solid.

$^1$H NMR (CDCl$_3$, 400 MHz) δ: 7.76-7.74 (2H, m), 7.67-7.65 (1H, dd J=1.6, 8.0 Hz), 1.57 (9H, s).

The following intermediate, Z49, was prepared by a manner analogous to Intermediate Z48.

Intermediate Z49

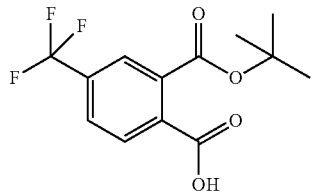 [SMILES: CC(C)(C)OC(=O)c1cc(C(F)(F)F)ccc1C(=O)O]

Synthesised starting from 4-trifluoromethyl phthalic anhydride.

$^1$H NMR (DMSO-d6, 400 MHz) δ: 13.72 (1H, s), 8.01-7.98 (2H, m), 7.83-7.81 (1H, d, J=8.0 Hz), 1.52 (9H, s).

Intermediate Z50

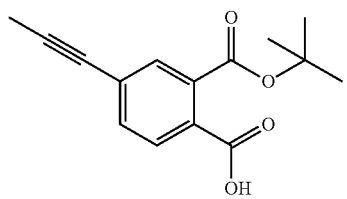 [SMILES: CC#Cc1ccc(C(=O)O)c(C(=O)OC(C)(C)C)c1]

To a solution of intermediate Z48 (500 mg, 1.7 mmol) in DMF (5 mL), was added DIPA (2 mL), Pd(PPh$_3$)$_2$Cl$_2$ (58 mg, 0.083 mmol) and CuI (31 mg, 0.17 mmol) at rt. The reaction mixture was cooled to −78° C. and propyne gas was purged for 20 min before the reaction mixture was heated to 80° C. and stirred for 16 h. On completion of the reaction (monitored by TLC), the reaction mixture was diluted with EtOAc (20 mL), washed with water (20 mL), dried (Na$_2$SO$_4$) and evaporated under reduced pressure. Purification by flash column chromatography (20% EtOAc in pet-ether) afforded intermediate Z50 (300 mg, 1.2 mmol, 68%) as a white solid.

$^1$H NMR (DMSO-d6, 400 MHz) δ: 13.30 (1H, s), 7.64-7.55 (3H, m), 2.08 (3H, s), 1.51 (9H, s).

Intermediate Z51

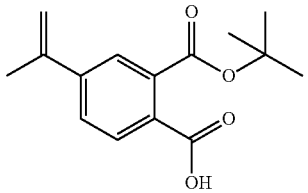 [SMILES: C=C(C)c1ccc(C(=O)O)c(C(=O)OC(C)(C)C)c1]

To a solution of intermediate Z48 (1.0 g, 3.3 mmol) and 2-Isopropenyl-4,4,5,5-tetramethyl-[1,3,2]dioxaborolane (0.80 mL, 6.66 mmol) in DMF/water (10.0 mL, 4:1) was added K$_3$PO$_4$ (1.55 mg, 7.32 mmol) and S-Phos (34 mg, 0.83 mmol) at rt and the reaction mixture was purged with argon for 30 min. Pd(OAc)$_2$ (93 mg, 0.42 mmol) was added and the mixture was heated to 85° C. and stirred for 22 h.

After completion of the reaction (monitored by TLC), the mixture was cooled to rt, diluted with EtOAc (30 mL) and washed with water (20 mL). The organic layer was washed with brine solution (20 mL), dried over anhydrous Na$_2$SO$_4$ and the solvents were evaporated under reduced pressure. Purification by flash column chromatography (50% EtOAc in pet. ether) afforded intermediate Z51 (700 mg, 2.7 mmol, 81%) as a white solid.

$^1$H NMR (DMSO-d6, 400 MHz) □: 13.15 (1H, br s), 7.69-7.68 (2H, d, J=0.8 Hz), 7.62 (1H, s), 5.56 (1H, s), 5.25 (1H, s), 2.13 (3H, s), 1.50 (9H, s). LCMS Method C: tR=3.34 min, m/z=263.16 [M−H]$^+$ Intermediate Z52

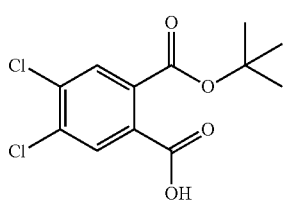 [SMILES: CC(C)(C)OC(=O)c1cc(Cl)c(Cl)cc1C(=O)O]

t-BuOH (0.170 g, 2.30 mmol) was added to a solution of 5,6-dichloroisobenzofuran-1,3-dione (0.500 g, 2.30 mmol) and DMAP (0.281 g, 2.304 mmol) in DCM (10 mL) at 0° C. The reaction temperature was stirred at rt for 12 h before concentration in vacuo to afford intermediate Z52 (0.631 g, 94%). The crude product was used without further purification.

Intermediate Z53

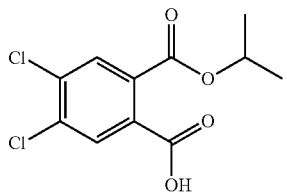 [SMILES: CC(C)OC(=O)c1cc(Cl)c(Cl)cc1C(=O)O]

A solution of 5,6-dichloroisobenzofuran-1,3-dione (500 mg, 2.3 mmol) in 2-propanol (5 ml) was heated to reflux for 18 h. The reaction was concentrated in vacuo to afford intermediate Z3 (500 mg, 79%) as white solid.

$^1$H NMR (DMSO, 400 MHz) δ: 13.73 (1H, s, br), 7.97 (1H, s), 7.92 (1H, s), 5.12-5.06 (1H, m), 1.29 (6H, d, J=4.0 Hz).

Intermediate Z54

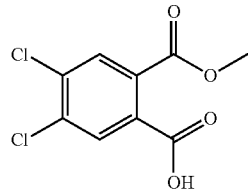

A solution of 5,6-dichloroisobenzofuran-1,3-dione (200 mg, 0.921 mmol) in MeOH (2 mL) was heated to reflux for 18 h. The reaction mixture was concentrated in vacuo to afford intermediate Z54 (200 mg, 87%) as a white solid.

$^1$H NMR (DMSO, 400 MHz) δ: 13.77 (1H, s, br), 8.00 (1H, s), 7.96 (1H, s), 3.81 (3H, s).

Intermediate Z55

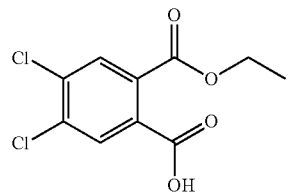 [SMILES: CCOC(=O)c1cc(Cl)c(Cl)cc1C(=O)O]

A mixture of 5,6-dichloroisobenzofuran-1,3-dione (600 mg, 2.76 mmol) in EtOH (20.0 mL) was heated at 100° C. for 16 h. After completion of the reaction (monitored by TLC), the reaction mixture was concentrated in vacuo to afford intermediate Z55 (600 mg, 83%).

$^1$H NMR (DMSO-d$_6$, 400 MHz) δ: 13.73 (1H, br), 7.99 (1H, s), 7.94 (1H, s), 4.30-4.25 (2H, q, J=7.0 Hz), 1.30-1.26 (3H, t, J=7.2 Hz).

Intermediate S52

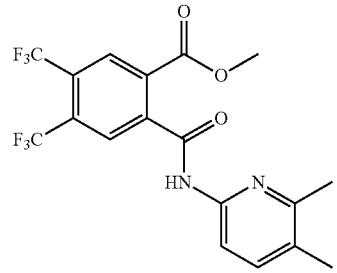 [SMILES: COC(=O)c1cc(C(F)(F)F)c(C(F)(F)F)cc1C(=O)Nc1ccc(C)c(C)n1]

To a solution of intermediate R2 (100 mg, 0.303 mmol) and 5,6-dimethylpyridin-2-amine (43 mg, 0.333 mmol) in toluene (2.0 mL) was added trimethyl aluminium (2.0 M in toluene, 0.29 mL, 0.606 mmol) at 0° C. The reaction mixture was stirred at 100° C. for 3 h. After completion of the reaction (monitored by TLC), the reaction mixture was quenched with water, extracted EtOAc (50 mL), dried over anhydrous Na$_2$SO$_4$ and the solvent was evaporated under reduced pressure. The crude product was purified by column chromatography to afford intermediate S52 (60 mg, 47%) as a pale yellow solid.

$^1$H NMR (DMSO-d6, 400 MHz) δ: 11.12 (1H, s), 8.35 (1H, s), 8.29 (1H, s), 7.91-7.89 (1H, d, J=8.0 Hz), 7.59-7.57 (1H, d, J=7.6 Hz), 3.82 (3H, s), 2.38 (3H, s), 2.23 (3H, s).

Prodrugs

It will be appreciated that an intermediate of type X could function as a pro-drug of a compound of formula [A], in that after administration, an intermediate of type X would be converted in vivo to afford a compound of formula A, indeed in an analogous process to the synthesis of compounds of formula A and type 1 according to scheme 1. It will be appreciated that wherein substituent A≠B a mixture of two isomers 1 and 1a may be obtained. Wherein B=H only isomer 1 is the subject of this invention, and the alternative isomer 1a is not so subject. Wherein A=B, only a single compound will be obtained.

For example intermediate X1 could afford example 1 and the corresponding regiosomer which is not a subject of this invention, in a ratio which may be determined by the exact conditions of the conversion in vivo. Symmetrically substituted intermediates X10, 11, 12, 13, 15, 19 and 20 could afford the single product examples 10, 11, 12, 13, 15, 47 and 48 respectively.

Similarly simple esters of molecules of formula A might act as pro-drugs from which a compound of formula A is liberated in vivo. Such esters may include, but not be limited to intermediates of type Y and S.

EXAMPLES

Example 1

N-(6-Methyl-pyridin-2-yl)-5-trifluoromethyl-phthalamic acid

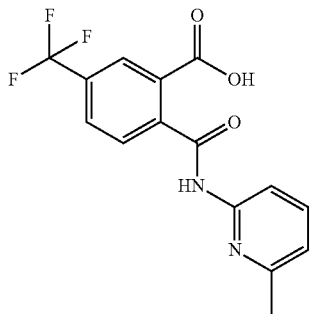 [SMILES: Cc1cccc(NC(=O)c2ccc(C(F)(F)F)cc2C(=O)O)n1]

Lithium hydroxide monohydrate (0.27 g, 6.5 mmol) was added to a suspension of intermediate X1 (1.0 g, 3.3 mmol) in THF/H$_2$O (1:1, 10 ml) and the mixture was stirred for 1 h at rt. The reaction was then acidified with saturated citric acid solution, and the resulting precipitate was filtered and washed with diethyl ether (20 mL). The solid was dried under vacuum to afford a mixture of product isomers as a white solid. Separation of the isomers by prep. HPLC (method 1) afforded the title compound (0.075 g, 0.23 mmol, 7%) as a white solid.

$^1$H NMR (DMSO-d6, 400 MHz) δ: 13.51 (1H, s), 10.96 (1H, s), 8.12 (1H, s), 8.01-7.98 (2H, m), 7.75-7.69 (2H, m), 7.02-7.00 (1H, d, J=7.6 Hz), 2.40 (3H, s). LCMS Method A: tR=0.46 min, m/z=325.1 [M+H]$^+$ In an analogues manner to the preparation of Example 1 of intermediates, Example 2-18, 47 and 48 were prepared from intermediates X2-20.

Example 2

5-Bromo-N-(6-methyl-pyridin-2-yl)-phthalamic acid

From Intermediate X2

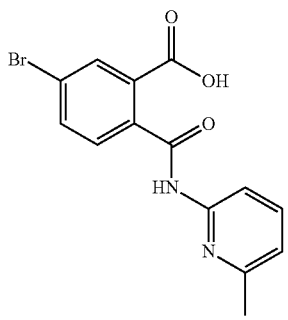

Synthesised using sodium hydroxide in ethanol/water (2:1)

$^1$H NMR (DMSO-d6, 400 MHz) δ: 10.80 (1H, br s), 7.95-7.94 (2H, m), 7.83-7.80 (1H, dd, J=8.4, 2.0 Hz), 7.72-7.68 (1H, t, J=7.8 Hz), 7.48-7.46 (1H, d, J=8.0 Hz), 7.00-6.98 (1H, d, J=7.2 Hz), 2.39 (3H, s).

LCMS Method A: tR=0.41 min, m/z=335.0 [M+H]$^+$

Example 3

5-Methyl-N-(6-methyl-pyridin-2-yl)-phthalamic acid

From Intermediate X3

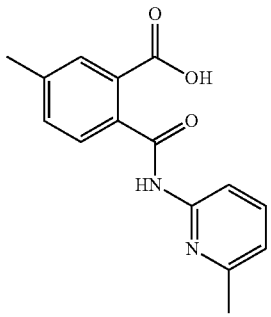 [SMILES: Cc1ccc(C(=O)Nc2cccc(C)n2)c(C(=O)O)c1]

Synthesised using sodium hydroxide in MeOH/water (2:1)

$^1$H NMR (DMSO-d6, 400 MHz) δ: 12.87 (1H, br s), 10.70 (1H, s), 7.97-7.95 (1H, d, J=8.4 Hz), 7.70-7.66 (1H, t, J=7.8 Hz), 7.63 (1H, s), 7.40 (2H, s), 6.98-6.97 (1H, d, J=7.2 Hz), 2.39 (6H, s).

LCMS Method A: tR=0.36 min, m/z=271.2 [M+H]$^+$

Example 4

5-Chloro-N-(6-methyl-pyridin-2-yl)-phthalamic acid

From Intermediate X4

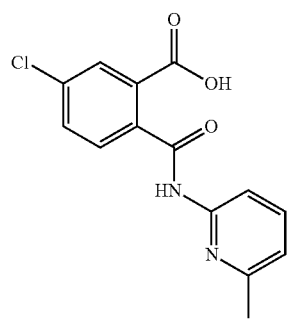 [SMILES: Cc1cccc(NC(=O)c2ccc(Cl)cc2C(=O)O)n1]

Synthesised using sodium hydroxide in MeOH/water (2:1)

$^1$H NMR (DMSO-d6, 400 MHz) δ: 13.32 (1H, br s), 10.89 (1H, s), 7.97-7.95 (1H, d, J=7.2 Hz), 7.82-7.81 (1H, d, J=2.0 Hz) 7.72-7.67 (2H, m), 7.55-7.53 (1H, d, J=8.4 Hz), 7.00-6.98 (1H, d, J=7.6 Hz), 2.40 (3H, s).

LCMS Method A: tR=0.39 min, m/z=291.1 [M+H]$^+$

Example 5

4,5-Dichloro-N-(6-methyl-pyridin-2-yl)-phthalamic acid

From Intermediate X5

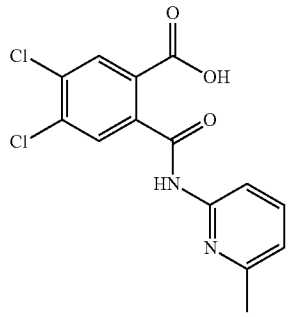 [SMILES: Cc1cccc(NC(=O)c2cc(Cl)c(Cl)cc2C(=O)O)n1]

Synthesised using lithium hydroxide monohydrate in THF/water (1:1)

$^1$H NMR (DMSO-d6, 400 MHz) δ: 13.48 (1H, s), 10.97 (1H, s), 8.00 (1H, s), 7.97-7.95 (1H, d, J=8.0 Hz), 7.85 (1H, s), 7.72-7.68 (1H, t, J=8.0 Hz), 7.01-6.99 (1H, d, J=7.6 Hz), 2.40 (3H, s).

LCMS Method A: tR=0.51 min, m/z=325.0 [M+H]$^+$

Example 6

5-Bromo-N-(3-methyl-4,5,6,7-tetrahydro-benzo[b]thiophen-2yl)-phthalamic acid

From Intermediate X6

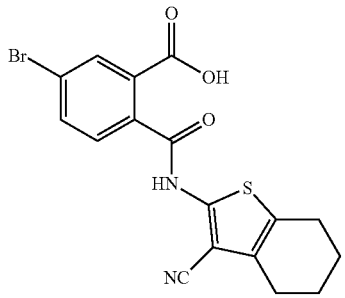 [SMILES: N#Cc1c(NC(=O)c2ccc(Br)cc2C(=O)O)sc2c1CCCC2]

Synthesised using lithium hydroxide monohydrate in THF/water (1:1)

$^1$H NMR (DMSO-d6, 400 MHz) δ: 13.55 (1H, br s), 12.19 (1H, br s), 8.06-8.04 (1H, d, J=2.1 Hz), 7.91-7.88 (1H, dd, J=8.2, 2.1 Hz), 7.51-7.49 (1H, d, J=8.2 Hz), 2.65-2.61 (2H, m), 2.53-2.49 (2H, m), 1.80-1.74 (4H, m).

LCMS Method B: tR=1.71 min, m/z=403.3 [M−H]$^+$

Example 7

N-(5,6-Dimethyl-pyridin-2-yl)-5-trifluoromethyl-phthalamic acid

From Intermediate X7

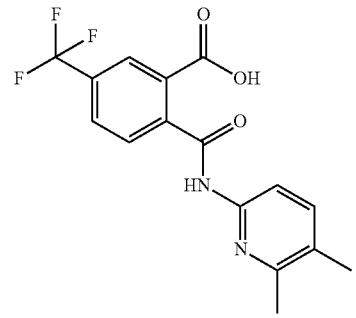 [SMILES: Cc1ccc(NC(=O)c2ccc(C(F)(F)F)cc2C(=O)O)nc1C]

Synthesised using lithium hydroxide monohydrate in THF/water (1:1)

$^1$H NMR (DMSO-d6, 400 MHz) δ: 13.48 (1H, br s), 10.87 (1H, s), 8.10 (1H, s), 8.00-7.98 (1H, d, J=7.6 Hz), 7.91-7.89 (1H, d, J=8.4 Hz), 7.74-7.72 (1H, d, J=7.6 Hz), 7.56-7.54 (1H, d, J=8.4 Hz), 2.35 (3H, s), 2.22 (3H, s).

LCMS Method A: tR=0.46 min, m/z=339.1 [M+H]$^+$

Example 8

N-(4-methyl-pyridin-2-yl)-5-trifluoromethyl-phthalamic acid

From Intermediate X8

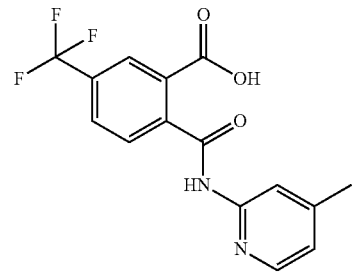 [SMILES: Cc1ccnc(NC(=O)c2ccc(C(F)(F)F)cc2C(=O)O)c1]

Synthesised using lithium hydroxide monohydrate in THF/water (1:1)

$^1$H NMR (DMSO-d6, 400 MHz) δ: 13.53 (1H, br s), 10.94 (1H, s), 8.19-8.17 (1H, d, J=4.8 Hz), 8.13 (1H, s), 8.03-8.01 (2H, m), 7.76-7.74 (1H, d, J=7.6 Hz), 7.00-6.98 (1H, d, J=4.8 Hz), 2.35 (3H, s).

LCMS Method A: tR=0.42 min, m/z=325.1 [M+H]$^+$

Example 9

N-(2-methyl-pyridin-4-yl)-5-trifluoromethyl-phthalamic acid

From Intermediate X9

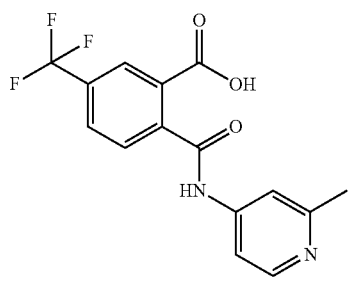 [SMILES: Cc1cc(NC(=O)c2ccc(C(F)(F)F)cc2C(=O)O)ccn1]

Synthesised using lithium hydroxide monohydrate in THF/water (1:1) $^1$H NMR (DMSO-d6, 400 MHz) δ: 13.80 (1H, br, s), 10.89 (1H, s), 8.34-8.33 (1H, d, J=6.0 Hz), 8.17 (1H, s), 8.08-8.06 (1H, d, J=8.0 Hz), 7.83-7.81 (1H, d, J=8.0 Hz), 7.54 (1H, s), 7.42-7.41 (1H, d, J=4.4 Hz), 2.44 (3H, s). LCMS Method A: tR=0.40 min, m/z=325.1 [M+H]$^+$

Example 10

4,5-Dichloro-N-(4-methyl-pyridin-2-yl)-phthalamic acid

From Intermediate X10

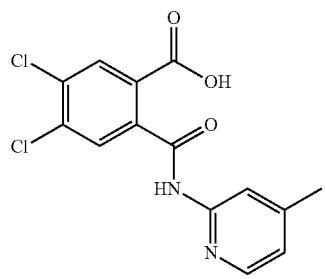 [SMILES: Cc1ccnc(NC(=O)c2cc(Cl)c(Cl)cc2C(=O)O)c1]

Synthesised using lithium hydroxide monohydrate in THF/water (1:1)
$^1$H NMR (DMSO-d6, 400 MHz) δ: 13.50 (1H, s), 10.93 (1H, s), 8.19-8.17 (1H, d, J=4.8 Hz), 8.02 (2H, s), 7.86 (1H, s), 6.99-6.98 (1H, d, J=4.8 Hz), 2.40 (3H, s).
LCMS Method A: tR=0.46 min, m/z=325.0 [M+H]$^+$

Example 11

4,5-Dichloro-N-(5,6-Dimethyl-pyridin-2-yl)-phthalamic acid

From Intermediate X11

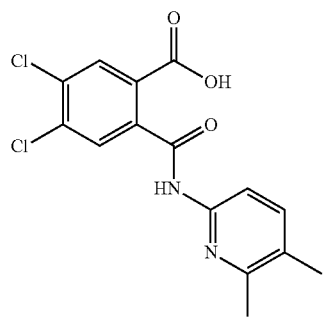 [SMILES: Cc1ccc(NC(=O)c2cc(Cl)c(Cl)cc2C(=O)O)nc1C]

Synthesised using lithium hydroxide monohydrate in THF/water (1:1)
$^1$H NMR (DMSO-d6, 400 MHz) δ: 13.46 (1H, br s), 10.84 (1H, s), 7.99 (1H, s), 7.89-7.87 (1H, d, J=8.4 Hz), 7.83 (1H, s), 7.55-7.53 (1H, d, J=8.4 Hz), 2.35 (3H, s), 2.22 (3H, s).
LCMS Method A: tR=0.50 min, m/z=339.1 [M+H]$^+$

Example 12

4,5-Dichloro-N-(2-methyl-pyridin-4-yl)-phthalamic acid

From Intermediate X12

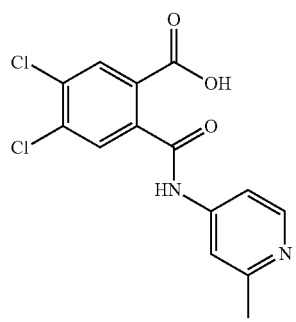 [SMILES: Cc1cc(NC(=O)c2cc(Cl)c(Cl)cc2C(=O)O)ccn1]

Synthesised using lithium hydroxide monohydrate in THF/H$_2$O (1:1)
$^1$H NMR (DMSO-d6, 400 MHz) δ: 13.66 (1H, br s), 10.96 (1H, s), 8.34-8.33 (1H, d, J=6.0 Hz), 8.06 (1H, s), 7.95 (1H, s), 7.52 (1H, s), 7.41-7.40 (1H, d, J=4.4 Hz), 2.49 (3H, s).
LCMS Method A: tR=0.45 min, m/z=325.0 [M+H]$^+$

Example 13

4,5-Dichloro-N-(2-methyl-pyrimidin-4-yl)-phthalamic acid

From Intermediate X13

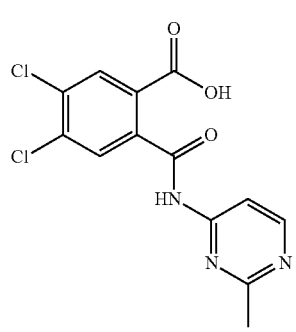 [SMILES: Cc1nccc(NC(=O)c2cc(Cl)c(Cl)cc2C(=O)O)n1]

Synthesised using lithium hydroxide monohydrate in THF/water (1:1)
$^1$H NMR (DMSO-d6, 400 MHz) δ: 13.61 (1H, s), 11.38 (1H, s), 8.61-8.59 (1H, d, J=5.6 Hz), 8.04 (1H, s), 7.95-7.93 (1H, d, J=5.2 Hz), 7.91 (1H, s), 2.51 (3H, s).
LCMS Method A: tR=0.46 min, m/z=326.0 [M+H]$^+$

Example 14

5-Chloro-6-fluoro-N-(6-methyl-pyridin-2-yl)-phthalamic acid

From Intermediate X14

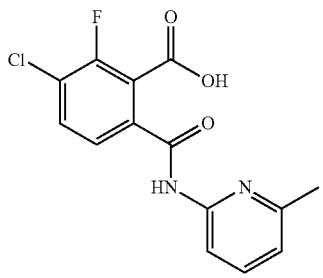 [SMILES: Cc1cccc(NC(=O)c2ccc(Cl)c(F)c2C(=O)O)n1]

Synthesised using lithium hydroxide monohydrate in THF/water (1:1)

$^1$H NMR (DMSO-d6, 600 MHz) □: 11.11 (1H, s), 7.92-7.89 (1H, d, J=8.6 Hz), 7.82-7.78 (1H, t, J=7.5 Hz), 7.74-7.70 (1H, t, J=7.5 Hz), 7.63-7.59 (1H, d, J=9.7 Hz), 7.06-7.03 (1H, d, J=7.5 Hz), 2.43 (3H, s).

LCMS Method A: tR=0.37 min, m/z=309.1 [M+H]$^+$

Example 15

4,5-Dimethyl-N-(6-methyl-pyridin-2-yl)-phthalamic acid

From Intermediate X15

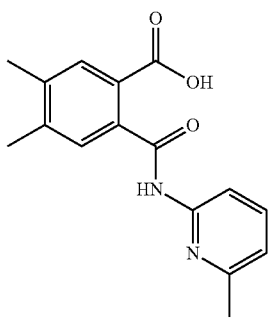 [SMILES: Cc1cccc(NC(=O)c2cc(C)c(C)cc2C(=O)O)n1]

Synthesised using lithium hydroxide monohydrate in THF/water (1:1)

$^1$H NMR (DMSO-d6, 600 MHz) δ: 12.77 (1H, br s), 10.67 (1H, s), 8.00-7.95 (1H, br d, J=7.0 Hz), 7.71-7.67 (1H, t, J=7.0 Hz), 7.62 (1H, s), 7.28 (1H, s), 6.99-6.96 (1H, d, J=7.0 Hz), 2.40 (3H, s), 2.29 (6H, s).

LCMS Method A: tR=0.41 min, m/z=285.2 [M+H]$^+$

Example 16

2-((3-chloro-5-(trifluoromethyl)pyridin-2-yl)carbamoyl)-5-(trifluoromethyl)benzoic acid From Intermediate X16

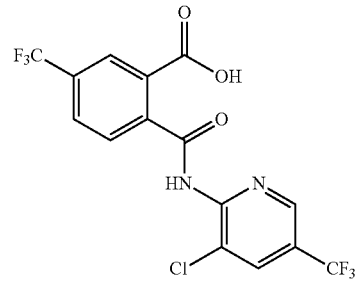 [SMILES: O=C(O)c1cc(C(F)(F)F)ccc1C(=O)Nc1ncc(C(F)(F)F)cc1Cl]

Synthesised using lithium hydroxide monohydrate in THF/H$_2$O (1:1)

$^1$H NMR (DMSO-d6, 400 MHz) δ: 13.65 (1H, s), 11.20 (1H, s), 8.79 (1H, s), 8.55-8.54 (1H, d, J=1.6 Hz), 8.14 (1H, s), 8.07-8.05 (1H, dd, J=8.0, 1.2 Hz), 7.81-7.79 (1H, d, J=8.0 Hz).

LCMS Method A: tR=0.69 min, m/z=413.0 [M+H]$^+$

Example 17

2-((4-methylpyrimidin-2-yl)carbamoyl)-5-(trifluoromethyl)benzoic acid

From Intermediate X17

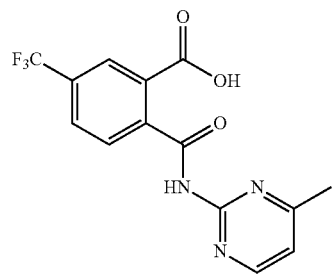 [SMILES: Cc1ccnc(NC(=O)c2ccc(C(F)(F)F)cc2C(=O)O)n1]

Synthesised using lithium hydroxide monohydrate in THF/H$_2$O (1:1) $^1$H NMR (DMSO-d6, 400 MHz) δ: 13.51 (1H, br s), 11.10 (1H, s), 8.39-8.38 (1H, d, J=3.2 Hz), 8.13 (1H, s) 7.99-7.97 (1H, d, J=8.0 Hz), 7.64-7.62 (1H, d, J=8.0 Hz), 7.00-6.99 (1H, d, J=4.4 Hz), 2.22 (3H, s).

LCMS Method A: tR=0.48 min, m/z=326.1 [M+H]$^+$

Example 18

2-((5,6-dimethylpyrazin-2-yl)carbamoyl)-5-(trifluoromethyl)benzoic acid

From Intermediate X18

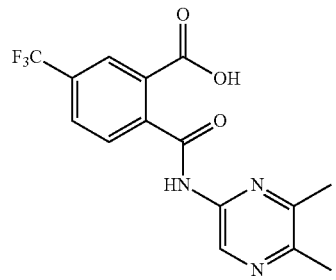 [SMILES: Cc1ncc(NC(=O)c2ccc(C(F)(F)F)cc2C(=O)O)nc1C]

Synthesised using lithium hydroxide monohydrate in THF/H$_2$O (1:1)

$^1$H NMR (DMSO-d6, 400 MHz) δ: 13.58 (1H, br s), 11.17 (1H, s), 9.09 (1H, s), 8.13 (1H, s), 8.04-8.02 (1H, d, J=8.0 Hz), 7.79-7.77 (1H, d, J=8.0 Hz), 2.46 (3H, s), 2.43 (3H, s).

LCMS Method A: tR=0.54 min, m/z=340.1 [M+H]$^+$

Example 19

5-Bromo-N-(5-methyl-pyridin-2-yl)-phthalamic acid

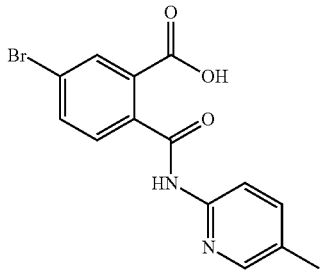 [SMILES: Cc1ccc(NC(=O)c2ccc(Br)cc2C(=O)O)nc1]

A solution of 5-bromo-isobenzofuran-1,3-dione (1.0 g, 4.42 mmol) and 2-amino-5-picoline (0.41 g, 4.42 mmol) in acetone (140 mL) was heated at reflux for 2 h. After cooling to rt, solvents were removed under reduced pressure and the resulting mixture of isomers were separated by prep. HPLC (method 2) to afford the title compound (0.060 g, 0.18 mmol, 4%) as a white solid.

$^1$H NMR (DMSO-d6, 400 MHz) δ: 13.33 (1H, br s), 10.85 (1H, s), 8.15 (1H, br, s), 8.06-8.04 (1H, d, J=8.0 Hz), 7.96-7.95 (1H, d, J=1.6 Hz), 7.83-7.81 (1H, dd, J=2.0, 8.0 Hz) 7.65-7.63 (1H, d, J=6.0 Hz), 7.49-7.47 (1H, d, J=8.4), 2.26 (3H, s).

LCMS Method A: tR=0.40 min, m/z=335.0 [M+H]$^+$

The following examples, 20-22, were prepared in an analogous manner to example 19, starting from 5-bromo-isobenzofuran-1,3-dione.

Example 20

5-Bromo-N-(5-chloro-pyridin-2-yl)-phthalamic acid

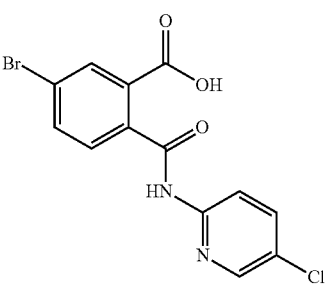 [SMILES: O=C(O)c1cc(Br)ccc1C(=O)Nc1ccc(Cl)cn1]

Synthesised using 2-amino-5-chloropyridine $^1$H NMR (DMSO-d6, 400 MHz) δ: 13.40 (1H, br s), 11.19 (1H, br s), 8.39-8.38 (1H, d, J=2.4 Hz), 8.20-8.18 (1H, d, J=8.4 Hz), 7.98-7.93 (2H, m), 7.85-7.83 (1H, d, J=8.0 Hz), 7.52-7.50 (1H, d, J=8.4 Hz).

LCMS Method A: tR=0.59 min, m/z=354.9 [M+H]$^+$

Example 21

5-Bromo-N-pyridin-2-yl-phthalamic acid

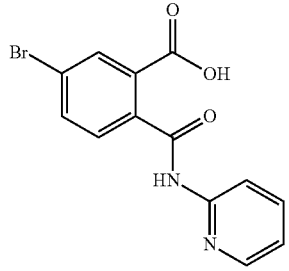 [SMILES: O=C(O)c1cc(Br)ccc1C(=O)Nc1ccccn1]

Synthesised using 2-amino-pyridine $^1$H NMR (DMSO-d6, 400 MHz) δ: 13.36 (1H, br s), 10.92 (1H, s), 8.33-8.32 (1H, d, J=3.6 Hz), 8.16-8.14 (1H, d, J=8.0 Hz), 7.98-7.97 (1H, d, J=2.0 Hz), 7.85-7.80 (2H, m), 7.50-7.48 (1H, d, J=8.0 Hz), 7.15-7.12 (1H, dd, J=4.8, 6.4 Hz).

LCMS Method A: tR=0.38 min, m/z=321.0 [M+H]$^+$

Example 22

5-Bromo-N-(6-chloro-pyridin-2-yl)-phthalamic acid

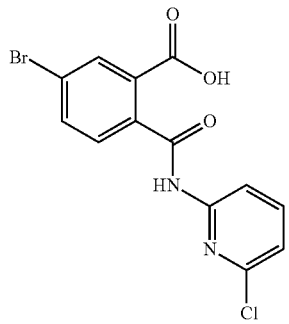 [SMILES: O=C(O)c1cc(Br)ccc1C(=O)Nc1cccc(Cl)n1]

Synthesised using 2-amino-6-chloropyridine $^1$H NMR (DMSO-d6, 400 MHz) δ: 13.41 (1H, br s), 11.25 (1H, s), 8.15-8.13 (1H, d, J=7.6 Hz), 7.98-7.98 (1H, d, J=1.6 Hz), 7.91-7.79 (2H, m), 7.51-7.49 (1H, d, J=8.0 Hz), 7.25-7.23 (1H, d, J=7.6 Hz).

LCMS Method A: tR=0.60 min, m/z=354.9 [M+H]$^+$

Example 23

5-Bromo-N-(5,6-dimethyl-pyridin-2-yl)-phthalamic acid

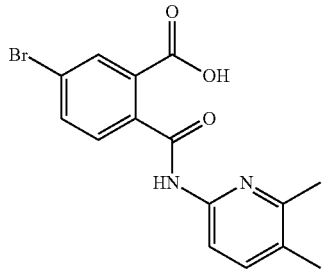 [SMILES: Cc1ccc(NC(=O)c2ccc(Br)cc2C(=O)O)nc1C]

A solution of intermediate Y21 (0.090 g, 0.22 mmol) in TFA/DCM (1:1, 2 mL) was stirred at rt for 4 h. After complete reaction (monitored by TLC), the reaction mixture was concentrated in vacuo to afford a solid which was washed with diethyl ether (6×9 mL) to give the title compound (0.045 g, 0.13 mmol, 59%) as a white solid.

$^1$H NMR (DMSO-d6, 400 MHz) δ: 13.29 (1H, br s), 10.75 (1H, s), 7.95-7.94 (1H, d, J=2.0 Hz), 7.89-7.87 (1H, d, J=8.4 Hz), 7.82-7.79 (1H, dd, J=8.0, 1.6 Hz), 7.54-7.52 (1H, d, J=8.0 Hz), 7.47-7.45 (1H, d, J=8.4 Hz), 2.35 (3H, s), 2.21 (3H, s).

LCMS Method A: tR=0.41 min, m/z=348.9 [M+H]+

The following examples 1, 2, 24-46 and 51 were prepared in an analogous manner to example 23 from the appropriate intermediates Y22-48.

Example 1

N-(6-Methyl-pyridin-2-yl)-5-trifluoromethyl-phthalamic acid

From Intermediate Y22

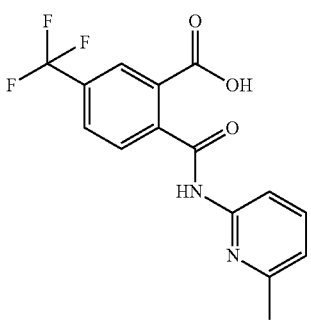 [SMILES: Cc1cccc(NC(=O)c2ccc(C(F)(F)F)cc2C(=O)O)n1]

$^1$H NMR (DMSO-d6, 400 MHz) δ: 13.51 (1H, s), 10.96 (1H, s), 8.12 (1H, s), 8.01-7.98 (2H, m), 7.75-7.69 (2H, m), 7.02-7.00 (1H, d, J=7.6 Hz), 2.40 (3H, s).

LCMS Method A: tR=0.46 min, m/z=325.1 [M+H]$^+$

Example 2

5-Bromo-N-(6-methyl-pyridin-2-yl)-phthalamic acid

From Intermediate Y23

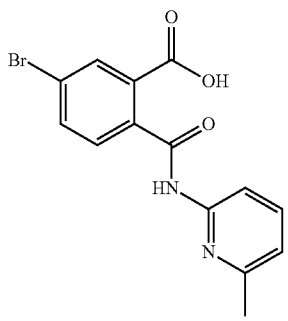

$^1$H NMR (DMSO-d6, 400 MHz) δ: 13.31 (1H, br s), 10.86 (1H, s), 7.95 (2H, m), 7.82-7.70 (2H, m), 7.48-7.46 (1H, d, J=8.0 Hz), 7.00-6.98 (1H, d, J=6.8 Hz), 2.39 (3H, s).

LCMS Method A: tR=0.41 min, m/z=335.0 [M+H]$^+$

Example 24

5-Bromo-N-(4-methyl-pyridin-2-yl)-phthalamic acid

From Intermediate Y24

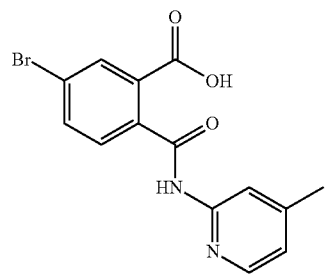 [SMILES: Cc1ccnc(NC(=O)c2ccc(Br)cc2C(=O)O)c1]

$^1$H NMR (DMSO-d6, 400 MHz) δ: 13.34 (1H, br s), 10.84 (1H, s), 8.18-8.17 (1H, d, J=4.8 Hz), 8.01 (1H, s), 7.97-7.96 (1H, d, J=2.0 Hz), 7.84-7.82 (1H, dd, J=2.0, 8.4 Hz) 7.48-7.46 (1H, d, J=8.4 Hz), 6.98-6.97 (1H, d, J=4.8), 2.34 (3H, s).

LCMS Method A: tR=0.37 min, m/z=335.0 [M+H]$^+$

Example 25

5-Bromo-N-(2-methyl-pyridin-4-yl)-phthalamic acid

From Intermediate Y25

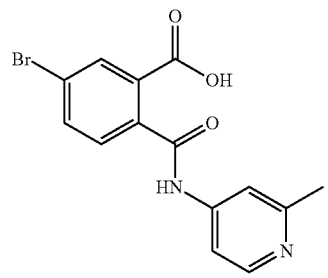 [SMILES: Cc1cc(NC(=O)c2ccc(Br)cc2C(=O)O)ccn1]

$^1$H NMR (DMSO-d6, 400 MHz) δ: 14.20 (1H, br s), 11.33 (1H, s), 8.52-8.50 (1H, d, J=6.4 Hz), 8.07-8.07 (1H, d, J=1.6 Hz), 7.96-7.94 (1H, dd, J=1.6, 8.0 Hz), 7.83 (1H, s), 7.72-7.70 (1H, d, J=8.4 Hz), 7.60-7.57 (1H, d, J=8.0 Hz), 2.58 (3H, s).

LCMS Method A: tR=0.36 min, m/z=335.0 [M+H]$^+$

Example 26

5-Bromo-N-pyridin-3-yl-phthalamic acid

From Intermediate Y26

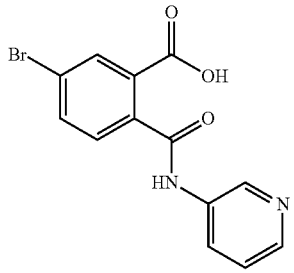 [SMILES: O=C(O)c1cc(Br)ccc1C(=O)Nc1cccnc1]

¹H NMR (DMSO-d6, 400 MHz) δ: 13.47 (1H, br s), 10.60 (1H, s), 8.81-8.80 (1H, d, J=2.4 Hz), 8.31-8.30 (1H, dd, J=4.8, 1.2 Hz), 8.11-8.09 (1H, d, J=8.8 Hz), 8.02-8.01 (1H, d, J=2.0 Hz), 7.91-7.88 (1H, dd, J=8.0, 2.0 Hz), 7.57-7.55 (1H, d, J=8.0 Hz), 7.41-7.38 (1H, dd, J=8.4, 4.8 Hz).

LCMS Method A: tR=0.33 min, m/z=321.0 [M+H]⁺

Example 27

5-Bromo-N-(3-methyl-pyridin-2-yl)-phthalamic acid

From Intermediate Y27

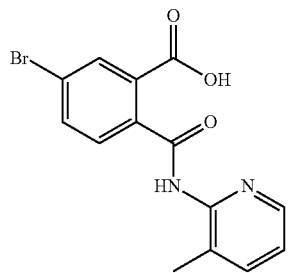 [SMILES: Cc1cccnc1NC(=O)c1ccc(Br)cc1C(=O)O]

¹H NMR (DMSO, 400 MHz) δ: 10.63 (1H, br s), 8.28 (1H, s), 7.96-7.95 (1H, d, J=1.6 Hz), 7.88-7.86 (1H, dd, J=1.6, 8.0 Hz), 7.79-7.77 (1H, d, J=6.8 Hz), 7.57-7.55 (1H, d, J=8.4 Hz), 7.29-7.26 (1H, t, J=5.2 Hz), 2.30 (3H, s).

LCMS Method A: tR=0.36 min, m/z=335.0 [M+H]⁺

Example 28

5-Bromo-N-(4-methyl-thiazol-2-yl)-phthalamic acid

From Intermediate Y28

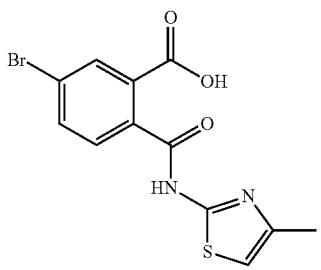 [SMILES: Cc1csc(NC(=O)c2ccc(Br)cc2C(=O)O)n1]

¹H NMR (DMSO-d6, 400 MHz) δ: 13.43 (1H, br s), 12.66 (1H, s), 7.99-7.98 (1H, d, J=2.0 Hz), 7.87-7.84 (1H, dd, J=8.0, 2.0 Hz), 7.56-7.54 (1H, d, J=8.4 Hz), 6.81-6.81 (1H, d, J=0.8 Hz), 2.27 (3H, s).

LCMS Method A: tR=0.52 min, m/z=341.0 [M+H]⁺

Example 29

5-Bromo-N-quinolin-2-yl-phthalamic acid

From Intermediate Y29

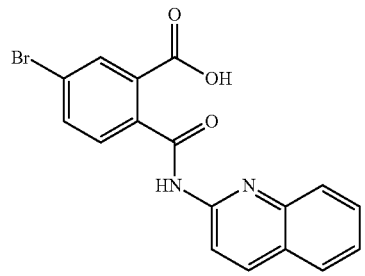 [SMILES: O=C(O)c1cc(Br)ccc1C(=O)Nc1ccc2ccccc2n1]

¹H NMR (DMSO-d6, 400 MHz) δ: 13.40 (1H, br s), 11.27 (1H, s), 8.39 (2H, m), 7.99-7.92 (2H, m), 7.87-7.84 (1H, dd, J=2.0, 8.4 Hz), 7.80-7.50 (4H, m).

LCMS Method A: tR=0.51 min, m/z=370.9 [M+H]⁺

Example 30

5-Bromo-N-(5,6-dichloro-pyridin-2-yl)-phthalamic acid

From Intermediate Y30

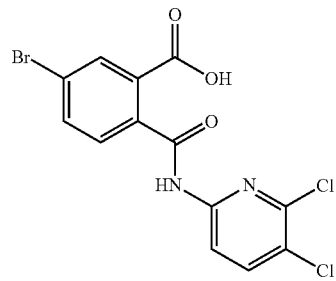 [SMILES: O=C(O)c1cc(Br)ccc1C(=O)Nc1ccc(Cl)c(Cl)n1]

¹H NMR (DMSO-d6, 400 MHz) δ: 13.40 (1H, br s), 11.6 (1H, s), 8.17-8.12 (2H, m), 7.98-7.97 (1H, d, J=2.0 Hz), 7.85-7.83 (1H, dd, J=1.6, 8.0 Hz), 7.53-7.50 (1H, d, J=8.4 Hz).

LCMS Method A: tR=0.68 min, m/z=388.8 [M+H]⁺

Example 31

5-Bromo-N-(6-methyl-pyridin-3-yl)-phthalamic acid

From Intermediate Y31

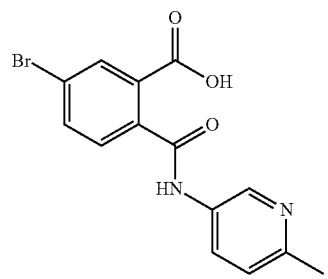 [SMILES: Cc1ccc(NC(=O)c2ccc(Br)cc2C(=O)O)cn1]

¹H NMR (DMSO-d6, 400 MHz) δ: 10.49 (1H, s), 8.67-8.66 (1H, d, J=2.4 Hz), 8.00-7.95 (2H, m), 7.89-7.87 (1H, dd, J=2.0, 8.0 Hz) 7.55-7.53 (1H, d, J=8.0 Hz), 7.24-7.22 (1H, d, J=8.4 Hz), 2.49 (3H, s).

LCMS Method A: tR=0.34 min, m/z=335.0 M+H]⁺

Example 32

5-Bromo-N-(6-methyl-pyridazin-3-yl)-phthalamic acid

From Intermediate Y32

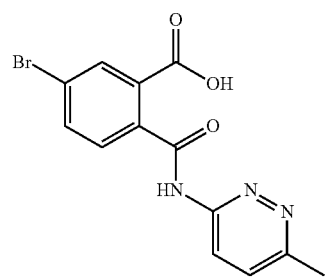 [SMILES: Cc1ccc(NC(=O)c2ccc(Br)cc2C(=O)O)nn1]

¹H NMR (DMSO-d6, 400 MHz) δ: 13.42 (1H, br s), 11.45 (1H, s), 8.27-8.25 (1H, d, J=9.2 Hz), 8.00-7.99 (1H, d, J=2.0 Hz), 7.87-7.85 (1H, dd, J=8.0, 2.0 Hz), 7.61-7.59 (1H, d, J=8.8 Hz), 7.54-7.52 (1H, d, J=8.4 Hz), 2.49 (3H, s).

LCMS Method A: tR=0.39 min, m/z=336.0 [M+H]⁺

Example 33

5-Bromo-N-(4,6-dimethyl-pyridin-2-yl)-phthalamic acid

From Intermediate Y33

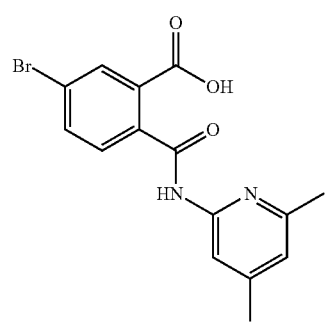 [SMILES: Cc1cc(C)nc(NC(=O)c2ccc(Br)cc2C(=O)O)c1]

¹H NMR (DMSO-d6, 400 MHz) δ: 13.29 (1H, br, s), 10.79 (1H, s), 7.94 (1H, s), 7.82-7.80 (2H, d, J=8.4 Hz), 7.46-7.44 (1H, d, J=7.6 Hz), 6.84 (1H, s), 2.34 (3H, s), 2.29 (3H, s)

LCMS Method A: tR=0.40 min, m/z=348.9 [M+H]⁺

Example 34

5-Bromo-N-(2-methyl-pyrimidin-4-yl)-phthalamic acid

From Intermediate Y34

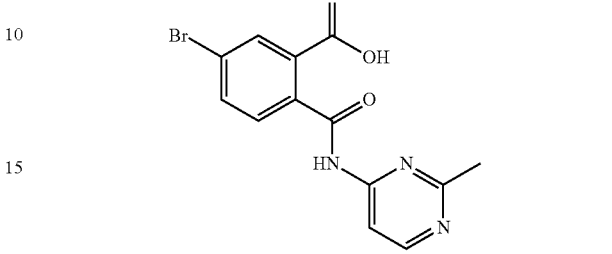

¹H NMR (DMSO-d6, 400 MHz) δ: 13.40 (1H, br s), 11.41 (1H, s), 8.59-8.58 (1H, d, J=5.6 Hz), 7.98-7.94 (2H, m), 7.85-7.83 (1H, dd, J=1.6, 8.0 Hz), 7.51-7.49 (1H, d, J=8.0 Hz), 2.51 (3H, s).

LCMS Method A: tR=0.38 min, m/z=336.0 [M+H]⁺

Example 35

5-Bromo-N-(6-methyl-pyrimidin-4-yl)-phthalamic acid

From Intermediate Y35

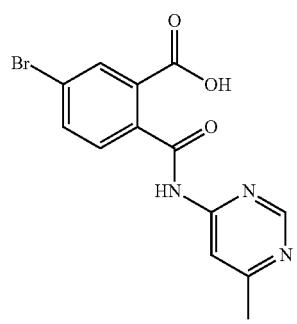

¹H NMR (DMSO-d6, 400 MHz) δ: 13.46 (1H, s), 11.28 (1H, s), 8.74 (1H, s), 8.04 (1H, s), 8.00 (1H, s), 7.87-8.85 (1H, d, J=7.6 Hz), 7.51-7.49 (1H, d, J=8.0 Hz), 2.46 (3H, s).

LCMS Method A: tR=0.41 min, m/z=336.0 [M+H]⁺

Example 36

N-(2-Methoxy-pyridin-4-yl)-5-trifluoromethyl-phthalamic acid

From Intermediate Y36

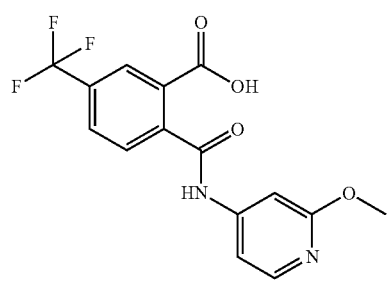 [SMILES: COc1cc(NC(=O)c2ccc(C(F)(F)F)cc2C(=O)O)ccn1]

¹H NMR (DMSO-d6, 400 MHz) δ: 13.69 (1H, br s), 10.78 (1H, s), 8.18 (1H, s), 8.09-8.05 (2H, t, J=7.2 Hz), 7.82-7.80 (1H, d, J=8.0 Hz), 7.17 (1H, s), 7.15-7.14 (1H, d, J=5.6 Hz), 3.83 (3H, s).

LCMS Method A: tR=0.45 min, m/z=341.1 [M+H]⁺

Example 37

N-(6-Methoxy-pyridin-2-yl)-5-trifluoromethyl-phthalamic acid

From Intermediate Y37

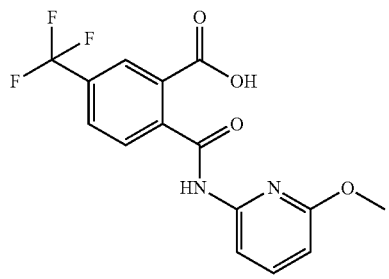 [SMILES: COc1cccc(NC(=O)c2ccc(C(F)(F)F)cc2C(=O)O)n1]

¹H NMR (DMSO-d6, 400 MHz) δ: 13.55 (1H, br s), 10.84 (1H, s), 8.14 (1H, s), 8.01-8.03 (1H, d, J=8.0 Hz), 7.76-7.72 (3H, m), 6.56-6.55 (1H, d, J=6.8 Hz), 3.81 (3H, s).

LCMS Method A: tR=0.62 min, m/z=341.1 [M+H]⁺

Example 38

N-Pyridin-2-ylmethyl-5-trifluoromethyl-phthalamic acid

From Intermediate Y38

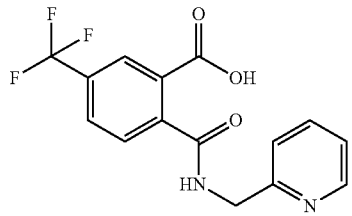 [SMILES: O=C(O)c1cc(C(F)(F)F)ccc1C(=O)NCc1ccccn1]

¹H NMR (DMSO-d6, 400 MHz) δ: 13.55 (1H, br s), 9.11-9.08 (1H, t, J=6.0 Hz), 8.51-8.50 (1H, d, J=4.0 Hz), 8.07 (1H, s), 8.02-8.00 (1H, d, J=8.0 Hz), 7.79-7.73 (2H, m), 7.53-7.51 (1H, d, J=7.6 Hz), 7.29-7.26 (1H, q, J=4.0 Hz), 4.54-4.53 (2H, d, J=6.4 Hz).

LCMS Method A: tR=0.35 min m/z=325.1 [M+H]⁺

Example 39

N-Pyridin-4-ylmethyl-5-trifluoromethyl-phthalamic acid

From Intermediate Y39

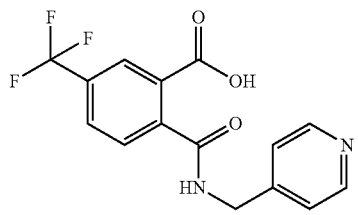 [SMILES: O=C(O)c1cc(C(F)(F)F)ccc1C(=O)NCc1ccncc1]

¹H NMR (DMSO-d6, 400 MHz) δ: 13.62 (1H, s), 9.10-9.07 (1H, t, J=6.0 Hz), 8.52-8.51 (2H, d, J=5.6 Hz), 8.08 (1H, s), 8.02-8.00 (1H, d, J=8.0 Hz), 7.74-7.72 (1H, d, J=8.0 Hz), 7.43-7.41 (2H, d, J=5.6 Hz), 4.49-4.47 (2H, d, J=6.0 Hz).

LCMS method 450: tR=0.34 min, m/z=325.1 [M+H]⁺

Example 40

N-Pyridin-3-ylmethyl-5-trifluoromethyl-phthalamic acid

From Intermediate Y40

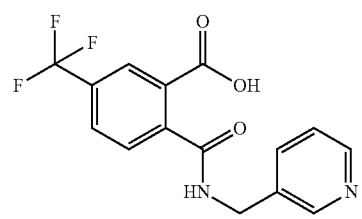 [SMILES: O=C(O)c1cc(C(F)(F)F)ccc1C(=O)NCc1cccnc1]

¹H NMR (DMSO-d6, 400 MHz) δ: 9.12-9.10 (1H, t, J=5.8 Hz), 8.72 (1H, s), 8.64-8.62 (1H, d, J=4.4 Hz), 8.14-8.12 (1H, d, J=8.0 Hz), 8.08 (1H, s), 8.02-8.00 (1H, d, J=7.6 Hz), 7.73-7.71 (1H, d, J=8.0 Hz), 7.67-7.63 (1H, q, J=4.4 Hz), 4.56-4.54 (2H, d, J=6.0 Hz).

LCMS Method A: tR=0.34 min, m/z=325.1 [M+H]⁺

Example 41

N-(6-Methyl-pyridin-2-yl)-5-propyl-phthalamic acid

From Intermediate Y43

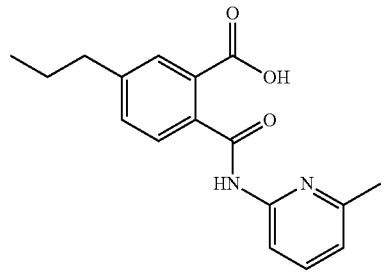 [SMILES: CCCc1ccc(C(=O)Nc2cccc(C)n2)c(C(=O)O)c1]

¹H NMR (DMSO-d6, 400 MHz) δ: 12.88 (1H, br s), 10.70 (1H, s), 7.97-7.95 (1H, d, J=8.0 Hz), 7.70-7.66 (1H, t, J=7.8 Hz), 7.63 (1H, s), 7.42 (2H, s), 6.98-6.97 (1H, d, J=7.6 Hz), 2.66-2.62 (2H, t, J=7.8 Hz), 2.39 (3H, s), 1.66-1.57 (2H, m), 0.92-0.89 (3H, t, J=7.2 Hz).

LCMS Method A: tR=0.48 min, m/z=299.1 [M+H]⁺

Example 42

N 5-Isopropenyl-N-(6-methyl-pyridin-2-yl)-phthalamic acid

From Intermediate Y42

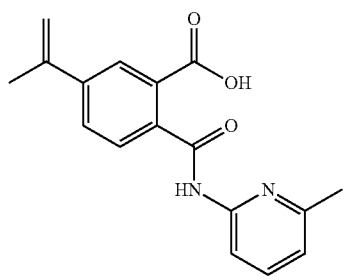 [SMILES: C=C(C)c1ccc(C(=O)Nc2cccc(C)n2)c(C(=O)O)c1]

¹H NMR (DMSO-d6, 400 MHz) δ: 10.81 (1H, s), 7.96-7.95 (1H, m), 7.90 (1H, s), 7.74-7.69 (2H, m), 7.51-7.49 (1H, d, J=8 Hz), 7.01-6.99 (1H, d, J=6.8 Hz), 5.55 (1H, s), 5.23 (1H, s), 2.40 (3H, s), 2.15 (3H, s).

LCMS Method A: tR=0.45 min, m/z=297.2 [M+H]⁺

Example 43

N 5-Isopropyl-N-(6-methyl-pyridin-2-yl)-phthalamic acid

From Intermediate Y47

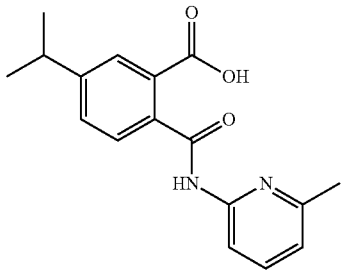 [SMILES: Cc1cccc(NC(=O)c2ccc(C(C)C)cc2C(=O)O)n1]

¹H NMR (DMSO-d6, 400 MHz) δ: 12.90 (1H, br s), 10.70 (1H, s), 7.96-7.94 (1H, d, J=8.0 Hz), 7.70-7.66 (2H, t, J=7.8 Hz), 7.49-7.43 (2H, m), 6.98-6.96 (1 h, d, J=7.6 Hz), 3.17-2.96 (1H, m), 2.39 (3H, s), 1.24 (6H, d, J=8.8 Hz).

LCMS Method A: tR=0.47 min, m/z=299.2 [M+H]⁺

Example 44

2-((2-methylpyrimidin-4-yl)carbamoyl)-5-(trifluoromethyl)benzoic acid

From Intermediate Y44

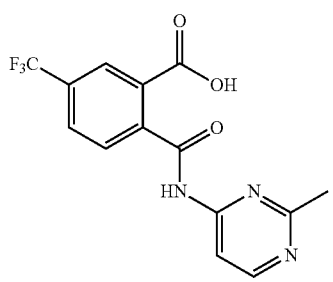 [SMILES: Cc1nccc(NC(=O)c2ccc(C(F)(F)F)cc2C(=O)O)n1]

¹H NMR (DMSO-d6, 400 MHz) δ: 11.52 (1H, s), 8.65-8.63 (1H, d, J=5.6 Hz), 8.15 (1H, s), 8.06-8.04 (1H, d, J=8.0 Hz), 8.01-8.00 (1H, d, J=5.2 Hz), 7.79-7.77 (1H, d, J=7.6 Hz), 2.53 (3H, s).

LCMS Method A: tR=0.43 min, m/z=326.1 [M+H]⁺

Example 45

2-((4,5-dimethylpyrimidin-2-yl)carbamoyl)-5-(trifluoromethyl)benzoic acid

From Intermediate Y45

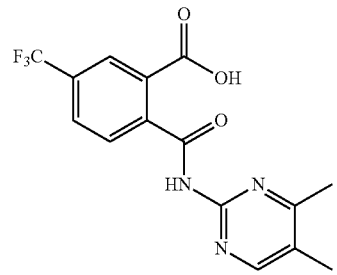 [SMILES: Cc1cnc(NC(=O)c2ccc(C(F)(F)F)cc2C(=O)O)nc1C]

¹H NMR (DMSO-d6, 400 MHz) δ: 13.44 (1H, br s), 10.97 (1H, s), 8.21 (1H, s), 8.12 (1H, s), 7.97-7.96 (1H, d, J=7.2 Hz), 7.62-7.60 (1H, d, J=8.0 Hz), 2.17 (3H, br s), 2.10 (3H, s).

LCMS Method A: tR=0.51 min, m/z=340.1 [M+H]⁺

Example 46

2-((5,6,7,8-tetrahydroquinolin-2-yl)carbamoyl)-5-(trifluoromethyl)benzoic acid

From Intermediate Y46

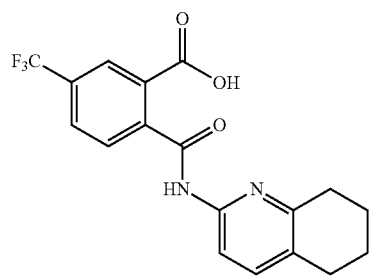 [SMILES: O=C(O)c1cc(C(F)(F)F)ccc1C(=O)Nc1ccc2c(n1)CCCC2]

¹H NMR (DMSO-d6, 400 MHz) δ: 13.49-13.46 (1H, d, J=10 Hz), 10.92 (1H, s), 8.10 (1H, s), 8.00-7.98 (1H, d, J=7.6 Hz), 7.92-7.90 (1H, d, J=7.6 Hz), 7.74-7.72 (1H, d, J=7.6 Hz), 7.50-7.48 (1H, d, J=8.0 Hz), 2.72-2.60 (4H, m), 1.81-1.73 (4H, m).

LCMS Method A: tR=0.51 min, m/z=365.1 [M+H]⁺

Example 47

2-((6-methylpyridin-2-yl)carbamoyl)-4,5-bis(trifluoromethyl)benzoic acid

From Intermediate X19

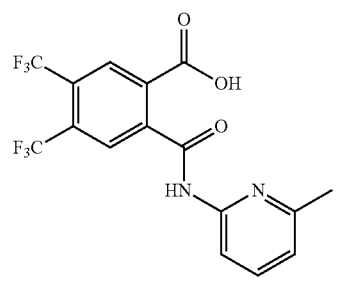 [SMILES: Cc1cccc(NC(=O)c2cc(C(F)(F)F)c(C(F)(F)F)cc2C(=O)O)n1]

Synthesised using lithium hydroxide monohydrate in THF/H$_2$O (1:1)

$^1$H NMR (DMSO-d6, 400 MHz) δ: 14.0 (1H, s, br), 11.29 (1H, s), 8.33 (1H, s), 8.23 (1H, s), 7.98 (1H, s) 7.75-7.71 (1H, t, J=8.0 Hz), 7.039-7.021 (1H, d, J=7.2 Hz), 2.41 (3H, s).

LCMS Method A: tR=0.61 min, m/z=392.9 [M+H]$^+$

Example 48

2-((5,6,7,8-tetrahydroquinolin-2-yl)carbamoyl)-4,5-bis(trifluoromethyl)benzoic acid From Intermediate X20

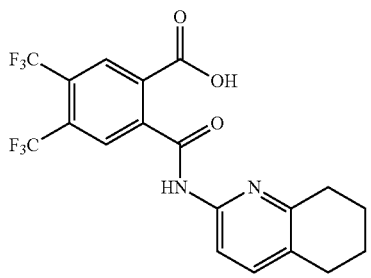 [SMILES: O=C(O)c1cc(C(F)(F)F)c(C(F)(F)F)cc1C(=O)Nc1ccc2c(n1)CCCC2]

Synthesised using lithium hydroxide monohydrate in THF/H$_2$O (1:1)

$^1$H NMR (DMSO-d6, 400 MHz) δ: 13.90 (1H, br), 11.05 (1H, s), 8.33 (1H, s), 8.20 (1H, s), 7.92-7.90 (1H, d, J=8.4 Hz), 7.52-7.50 (1H, d, J=8.0 Hz), 2.72-2.71 (4H, m), 1.76-1.74 (4H, m).

LCMS Method A: tR=0.66 min, m/z=433.1 [M+H]$^+$

Example 49

2-((5,6-dimethylpyridin-2-yl)carbamoyl)-4,5-bis(trifluoromethyl)benzoic acid

From Intermediate S52

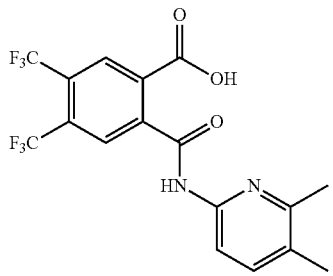 [SMILES: Cc1ccc(NC(=O)c2cc(C(F)(F)F)c(C(F)(F)F)cc2C(=O)O)nc1C]

LiOH.H$_2$O (12 mg, 0.285 mmol) was added to a solution of intermediate S52 (60 mg, 0.142 mmol) in THF/H$_2$O (1:1) (3.0 mL) and the reaction mixture was stirred at rt for 1 h. THF was then removed in vacuo and the crude material was acidified with 1N HCl. The resulting solid was filtered, washed with pentane and dried under reduced pressure to afford the title compound (45 mg, 78%) as a white solid.

$^1$H NMR (DMSO-d6, 400 MHz) δ: 11.41 (1H, s), 8.30 (1H, s), 8.23 (1H, s), 7.92-7.90 (1H, d, J=7.2 Hz), 7.57-7.55 (1H, d, J=8.4 Hz), 2.36 (3H, s), 2.22 (3H, s).

LCMS Method A: tR=0.61 min, m/z=407.0 [M+H]$^+$

Example 50

2-((2-methylpyrimidin-4-yl)carbamoyl)-4,5-bis(trifluoromethyl)benzoic acid

From Intermediate T1

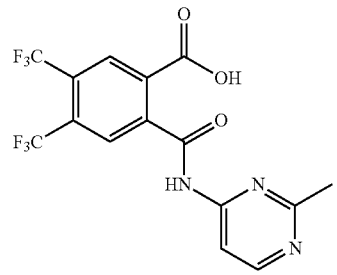 [SMILES: Cc1nccc(NC(=O)c2cc(C(F)(F)F)c(C(F)(F)F)cc2C(=O)O)n1]

To a solution of intermediate T1 (100 mg, 0.331 mmol) and 2-methylpyrimidin-4-amine (36 mg, 0.331 mmol) in DCM (3.0 mL) were added HATU (188 mg, 0.496 mmol) and DIPEA (0.18 mL, 0.993 mmol) at 0° C. The reaction mixture was stirred at room temperature for 18 h. After completion of the reaction (monitored by TLC), the reaction mixture was diluted with water (50 mL), extracted with EtOAc (50 mL) and dried over anhydrous Na$_2$SO$_4$. The crude product was purified by column chromatography to afford the title compound (100 mg, 77%) as a white solid.

$^1$H NMR (DMSO-d6, 400 MHz) δ: 14.07 (1H, br), 11.61 (1H, s), 8.63-8.62 (1H, d, J=6.0 Hz), 8.36 (1H, s), 8.30 (1H, s), 7.95 (1H, s), 2.49 (3H, s).

LCMS Method A: tR=0.55 min, m/z=393.9 [M+H]$^+$

Example 51

2-((2,6-dimethylpyridin-4-yl)carbamoyl)-5-(trifluoromethyl)benzoic acid

From Intermediate Y48

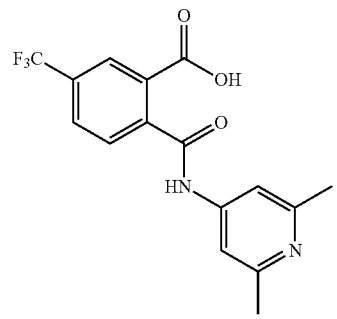 [SMILES: Cc1cc(NC(=O)c2ccc(C(F)(F)F)cc2C(=O)O)cc(C)n1]

$^1$H NMR (DMSO-d6, 400 MHz) δ: 14.0 (1H, br), 11.56 (1H, s), 8.23 (1H, s), 8.16-8.14 (1H, d, J=8.0 Hz), 7.87-7.85 (1H, d, J=8.0 Hz), 7.73 (2H, s), 2.61 (6H, s).

LCMS Method A: tR=0.42 min, m/z=339.0 [M+H]$^+$

Expression and Purification of Proteins

Human Sortilin extracellular domain (78-755) including the propeptide (34-77) of Q99425 and a C-terminal 6×His tag was expressed in HEK 293 cells using the episomal expression vector pCEP-PU. Expressed sortilin-extracellular domain was purified from culture media on a Ni$^{2+}$ NTA-agarose (Qiagen) column according to the manufacturer's instructions.

Human progranulin (P28799; 18-593) was expressed in HEK 293F cells using the pcDNA 3.1(−) expression vector. Purification from culture media was done by capture on capto-Q (GE-healthcare). Fractions eluting from the column was precipitated with 2M Ammonium Sulfate and centrifuged. The precipitate was dissolved in PBS and separated on S200 size-exclusion column. Fractions with progranulin was identified by SDS-PAGE and pooled accordingly.

The propart of human beta nerve growth factor (P01138; 19-121) was expressed as a C-terminal fusion to GST using the pGEX expression plasmid in *e. coli* BL21 cells. Induction was initiated by adding 1 mM IPTG and continued for 4 hours. Cells were harvested by centrifugation and lysed using "block buster protein extraction" kit from Novagen. Cleared lysate was purified using the GSTtrap columns (GE healthcare) according to the instructions from manufacturer.

Mouse his-Sortilin was purchased from R&D Systems.

hSortilin Affinity Assay

The compound affinity was determined by measuring the displacement of 3H-neurotensin binding to hSortilin using a SPA based assay format.

The Sortilin assay was performed in total volume of 40 ul in 50 mM HEPES pH 7.4 assay buffer containing 100 mM NaCl, 2.0 mM $CaCl_2$, 0.1% BSA and 0.1% Tween-20. Varying concentration of compounds where pre-incubated for 30 min at RT with 150 nM of 6his-Sortilin. 5 nM [$^3$H]-Neurotensin was added as radioligand and nonspecific binding defined as the binding in the presence 20 μM of Neurotensin. Ni chelate imaging beads (Perkin Elmer) was added and the plate was slowly shaked in the dark for 60 min. The imaging beads were allowed minimum 6 hours settling time before the plate was read on a ViewLux with 360 sec exposure time. Dose-response evaluation of compounds was performed with 10 concentrations of drugs (covering 3 decades). $IC_{50}$ values were calculated by non-linear regression using the sigmoid concentration-response (variable slope) using Xlfit 4 (IDBS, UK). The results were given as Ki values (nM) derived from computer fitted IC50 values converted to Ki values using the Cheng-Prusoff equation (Ki=IC50/(1+(L/Kd))). Kd for Neurotensin was determined to 100 nM

| Example Number | hSortilin NTS Binding $IC_{50}$ (nM) | hSortilin Ki |
|---|---|---|
| 1 | 450 | 429 |
| 2 | 1200 | 1143 |
| 3 | 6400 | 6095 |
| 4 | 1400 | 1333 |
| 5 | 830 | 790 |
| 6 | 4000 | |
| 7 | 170 | 162 |
| 8 | 1000 | 952 |
| 9 | 700 | 667 |
| 10 | 2200 | 2095 |
| 11 | 480 | 457 |
| 12 | 1800 | 1714 |
| 13 | 480 | 457 |
| 14 | 4200 | 4000 |
| 15 | 3400 | 3238 |
| 16 | 360 | 343 |
| 17 | 360 | 343 |
| 18 | 240 | 229 |
| 19 | 1700 | 1619 |
| 20 | 990 | 943 |
| 21 | 3600 | 3429 |
| 22 | 1600 | 1524 |
| 23 | 570 | 543 |
| 24 | 2400 | 2286 |
| 25 | 1800 | 1714 |
| 26 | 5500 | 5238 |
| 27 | 64%* | |
| 28 | 3600 | 3429 |
| 29 | 1300 | 1238 |
| 30 | 2100 | 2000 |
| 31 | 70%* | |
| 32 | 3200 | 3048 |
| 33 | 970 | 924 |
| 34 | 490 | 467 |
| 35 | 2000 | 1905 |
| 36 | 750 | 714 |
| 37 | 1300 | 1238 |
| 38 | 1600 | 1524 |
| 39 | 7500 | 7143 |
| 40 | 4800 | 4571 |
| 41 | 3600 | 3429 |
| 42 | 5200 | 4952 |
| 43 | 1100 | 1048 |
| 44 | 300 | 286 |
| 45 | 200 | 190 |
| 46 | 88 | 84 |
| 47 | 1200 | 1144 |
| 48 | 760 | 721 |
| 49 | 750 | 734 |
| 50 | 620 | 599 |
| 51 | 640 | 614 |

*Inhibition at 50 μM mSortilin Affinity Assay

The compound affinity was determined by measuring the displacement of 3H-neurotensin binding to msortilin using a SPA based assay format.

The Sortilin assay was performed in total volume of 40 ul in 50 mM HEPES pH 7.4 assay buffer containing 100 mM NaCl, 2.0 mM $CaCl_2$, 0.1% BSA and 0.1% Tween-20. Varying concentration of compounds where pre-incubated for 30 min at RT with 50 nM of 6his-Sortilin. 5 nM [$^3$H]-Neurotensin was added as radioligand and nonspecific binding defined as the binding in the presence 20 μM of Neurotensin. Ni chelate imaging beads (Perkin elmer) was added and the plate was slowly shacked in the dark for 60 min. The imaging beads were allowed minimum 6 hours settling time before the plate was read on a ViewLux with 360 sec exposure time. Dose-response evaluation of compounds was performed with 10 concentrations of drugs (covering 3 decades). $IC_{50}$ values were calculated by non-linear regression using the sigmoid concentration-response (variable slope) using Xlfit 4 (IDBS, UK). The results were given as Ki values (nM) derived from computer fitted IC50 values converted to Ki values using the Cheng-Prusoff equation (Ki=IC50/(1+(L/Kd))). Kd for Neurotensin was determined to 100 nM.

| Example Number | mSortilin NTS Binding $IC_{50}$ (nM) | mSortilin $K_i$ (nM) |
|---|---|---|
| 1 | 220 | 210 |

Inhibition of Pro part of ProNGF to hSortilin

The inhibition of proNGF to Sortilin was determined by measuring the binding of the pro part of proNGF to Sortilin using homogeneous time resolved fluorescence technology. The pro part of proNGF was fused to GST tag and Sortilin was tagged with His. A europium label GST antibody and a XL665 label His antibody was used to detect the binding of pro-GST to his-Sortilin. The signal is generated once the proteins interact with each other to bring the labeled antibodies into proximity.

The pro Sortilin assay was performed in total volume of 20 ul in 50 mM HEPES pH 7.4 assay buffer containing 100 mM NaCl, 2.0 mM $CaCl_2$, 0.1% BSA and 0.1% Tween-20. Varying concentration of compounds where incubated for 15 min at RT with 50 nM of 6his-Sortilin and 6 nM of pro-GST. 4 nM of anti-GST-Eu and 25 nM of anti-His-XL665 were added together with KF (final concentration 200 mM) and following 150 min incubation at room temperature in the dark the fluorescence was measured with excitation of 320 nm and dual emission of 665 and 615 nm on the an envision reader (Perkin Elmer) Signal was expressed in terms of HTRF ratio (fluorescence intensity at 665 nm/fluorescence intensity at 615 nm×10,000) Inhibition of binding of proGST to Sortilin was expressed as a percent inhibition of the control response to 20 µM of Neurotensin (100% inhibition) relative to a buffer basal control (0% inhibition). $IC_{50}$ values were calculated by nonlinear regression using the sigmoid concentration-response (variable slope) using Xlfit 4 (IDBS, UK).

| Example Number | $IC_{50}$ (nM) |
| --- | --- |
| 1 | 260 |

Inhibition of hProgranulin to hSortilin

The inhibition of progranulin to Sortilin was determined by measuring the binding of the progranulin of proNGF to his-Sortilin using homogeneous time resolved fluorescence technology. A europium label progranulin antibody and a XL665 label His antibody was used to detect the binding of progranulin to his-Sortilin. The signal is generated once the proteins interact with each other to bring the labeled antibodies into proximity.

The progranulin Sortilin assay was performed in total volume of 20 ul in 50 mM Phosphate buffer pH 7.0 assay buffer containing 0.1% BSA. Varying concentration of compounds where incubated for 15 min at RT with 50 nM of 6his-Sortilina and 4 nM of Progranulin. 0.7 nM of anti-progranulin-Eu and 7 nM of anti-His-XL665 were added together with KF (final concentration 200 mM) and following 120 min incubation at room temperature in the dark, The plate was kept at 4° C. overnight and next day the fluorescence was measured with excitation of 320 nm and dual emission of 665 and 615 nm on the an envision reader (Perkin Elmer) Signal was expressed in terms of HTRF ratio (fluorescence intensity at 665 nm/fluorescence intensity at 615 nm×10,000) Inhibition of binding of progranulin to Sortilin was expressed as a percent inhibition of the control response to 20 µM of Neurotensin (100% inhibition) relative to a buffer basal control (0% inhibition). $IC_{50}$ values were calculated by nonlinear regression using the sigmoid concentration-response (variable slope) using Xlfit 4 (IDBS, UK).

| Example Number | $IC_{50}$ (nM) |
| --- | --- |
| 1 | 1800 |

Endogenous PGRN Endocytosis Assay

Stable cell lines expressing human sortilin (S-18) were generated by transfecting HEK293 cells with a human sortilin expression vector, followed by few rounds of passage with the appropriate selection agent.

HEK293 cells and S-18 cells were found to secrete PGRN continuously into the media without any stimulation. Progranulin binds to sortilin and is endocytosed (Hu et al. 2010). Blocking sortilin and progranulin interaction results in PGRN accumulation in the media. Compounds that do not block sortilin and progranulin interaction have no effect on PGRN levels in the media.

On day 1, S-18 cells are seeded in a 96 well plate. After 24 hrs, media is completely replaced with either media or one of the test compounds. All compounds were tested at 10 uM unless otherwise specified. Media is collected on day 3 and analyzed using PGRN ELISA (R&D). Cell viability is assessed by Cell TiterGlo (Pro Mega) to evaluate cytotoxic effect of the compounds.

Different compounds were added to S-18 cells to evaluate effect on progranulin. Neurotensin is a natural ligand for sortilin and blocks sortilin binding to progranulin which results in progranulin accumulation in the media. Addition of Neurotensin or Example 1 to S-18 cells shows an increase in PGRN in cell culture media by 85-100% as compared to control wells.

On the other hand, scrambled neurotensin (LIYPR-NEYELRKP; SEQ ID NO:1) or Standard 1 do not bind to sortilin and PGRN levels in the media are similar to untreated wells.

In a similar but slightly different experimental paradigm, PGRN is allowed to accumulate for 24 hrs, so compounds can compete with PGRN to bind sortilin. On day 2, the compounds are added to the cells and incubated for a further 24 hrs, when the media is harvested and PGRN levels analyzed using ELISA kit.

Neurotensin and Example 1, compete with PGRN in media, increase PGRN levels in cell culture media. Scr. NT and Standard 1 did not have any effect on PGRN endocytosis as shown in FIG. 1.

Cellomics Progranulin Assay

Transfected HEK 293 cells (with control or sortilin expression plasmids) or stable HEK293 cells expressing human sortilin (S-18) were used in this assay. Cells are trypsinized and plated in 96 well plates. In the case of transiently transfected cells, they were plated 24 hrs after transfection in 96 well plates. Next day, media was changed completely and test compounds added to cells for 30 min. followed by PGRN for 60 min. At the end of the study (after 1.5 hrs), the cells were fixed and stained for sortilin and progranulin. All stained plates were analyzed by Cellomics Array Scan (Thermo Fischer) and average staining intensity for PGRN and sortilin are calculated per cell in each well.

Progranulin used in this assay was harvested from media following transient transfection of progranulin expression plasmids in HEK 293 cells. PGRN levels were measured using PGRN ELISA kit (R&D).

Figure 2:
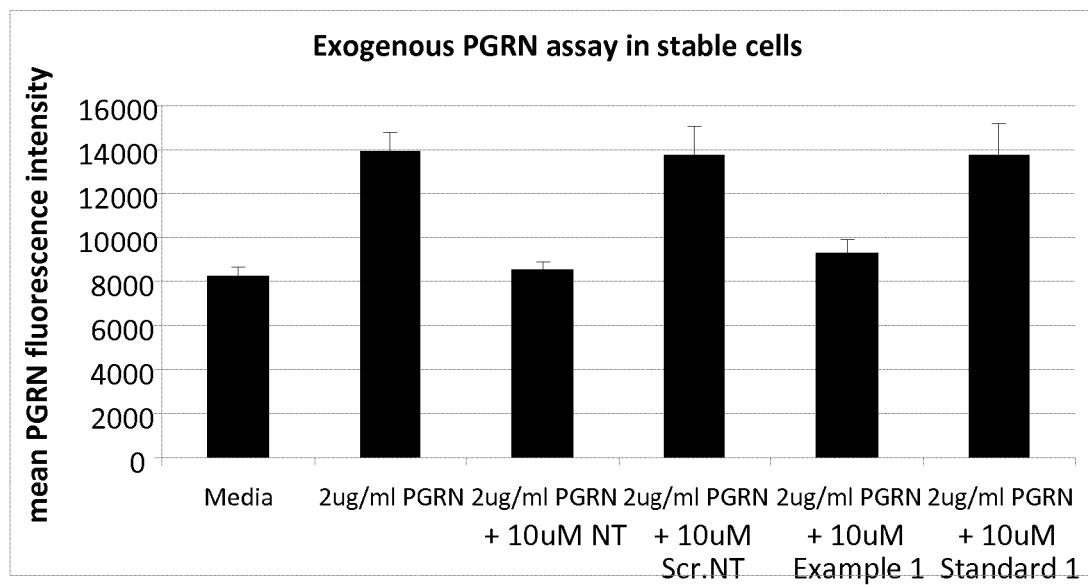
FIG. 2, shows that the addition of Neurotensin or the compound from Example 1 blocks binding or endocytosis of PGRN to sortilin expressing cells.

Addition of PGRN to wells was readily endocytosed and lead to increased fluorescent signal in sortilin transfected wells. Addition of neurotensin, or the compound from Example 1 prevent sortilin bindng to progranulin (FIG. 2) Hence, PGRN was not endocytosed and PGRN fluorescence intensity was similar to control levels.

Scrambled neurotensin did not bind to sortilin and was used as negative control. In wells treated with scrambled neurotensin or Standard 1, PGRN bound sortilin and was endocytosed and fluorescent intensity is significantly increased as seen in wells treated with only PGRN Scrambled neurotensin has the sequence of: LIYPR-NEYELRKP (SEQ ID NO:1)

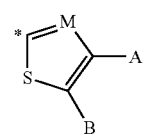
(2)

The invention claimed is:

1. A compound of Formula [A]:

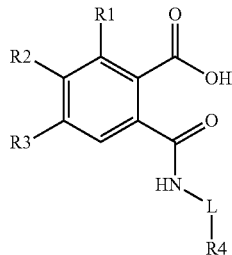

Formula [A]

wherein:

R1 represents H or F,

R2 represents halogen, $C_1$-$C_6$ alkyl, $C_2$-$C_6$ alkenyl or $C_1$-$C_6$ halogenated alkyl, R3 represents halogen, H, $C_1$-$C_6$ alkyl or $C_1$-$C_6$ halogenated alkyl, L is a direct bond or represents $CH_2$, $R_4$ represents:

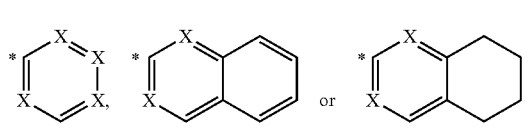
(1)

wherein X represents C or N, wherein N is present at 1 or 2 positions, and

* denotes the attachment point, or wherein:

M represents C, N or CC≡N,

A and B each independently represents H, $C_1$-$C_3$ alkyl, or

A and B form a 5, 6 or 7 membered carbocyclic saturated or unsaturated ring together with the carbon atom they are attached to, and * denotes the attachment point, or (3)

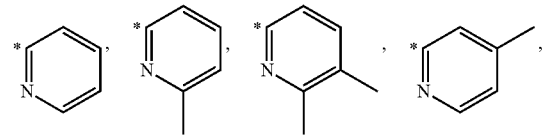

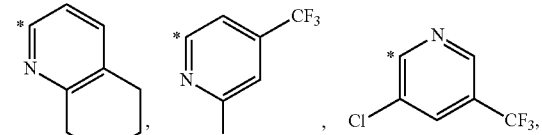

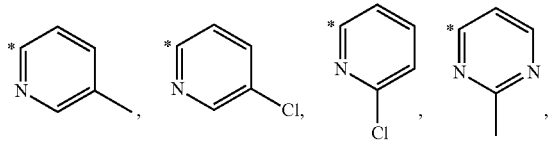

-continued wherein * denotes the attachment point;
that may be substituted with C≡N, 1 or 2 $C_1$-$C_3$ alkyl, 1 or 2 halogenated alkyl, 1 or 2 $C_1$-$C_3$ alkoxy or 1 or 2 halogen(s), or a pharmaceutically acceptable salt or prodrug thereof, with the proviso that the compound is not 5-methyl-2-[[(4-methyl-2-thiazolyl)amino]carbonyl].

2. The compound according to claim 1, wherein the halogenated alkyl is $CF_3$.

3. The compound according to claim 1, wherein R2 is Cl, Br or $CF_3$ and R3 is H or Cl.

4. The compound according to claim 1, wherein said compound is selected from the group consisting of:
N-(6-Methyl-pyridin-2-yl)-5-trifluoromethyl-phthalamic acid;
5-Bromo-N-(6-methyl-pyridin-2-yl)-phthalamic acid;
5-Methyl-N-(6-methyl-pyridin-2-yl)-phthalamic acid;
5-Chloro-N-(6-methyl-pyridin-2-yl)-phthalamic acid;
4,5-Dichloro-N-(6-methyl-pyridin-2-yl)-phthalamic acid;
5-Bromo-N-(3-methyl-4,5,6,7-tetrahydro-benzo[b]thiophen-2yl)-phthalamic acid;
N-(5,6-Dimethyl-pyridin-2-yl)-5-trifluoromethyl-phthalamic acid;
N-(4-methyl-pyridin-2-yl)-5-trifluoromethyl-phthalamic acid;
N-(2-methyl-pyridin-4-yl)-5-trifluoromethyl-phthalamic acid;
4,5-Dichloro-N-(4-methyl-pyridin-2-yl)-phthalamic acid;
4,5-Dichloro-N-(5,6-Dimethyl-pyridin-2-yl)-phthalamic acid;
4,5-Dichloro-N-(2-methyl-pyridin-4-yl)-phthalamic acid;
4,5-Dichloro-N-(2-methyl-pyrimidin-4-yl)-phthalamic acid;
5-Chloro-6-fluoro-N-(6-methyl-pyridin-2-yl)-phthalamic acid;
4,5-Dimethyl-N-(6-methyl-pyridin-2-yl)-phthalamic acid;
2-((3-chloro-5-(trifluoromethyl)pyridin-2-yl)carbamoyl)-5-(trifluoromethyl)benzoic acid;
2-(4-methylpyrimidin-2-yl)carbamoyl)-5-(trifluoromethyl)benzoic acid;
2-((5,6-dimethylpyrazin-2-yl)carbamoyl)-5-(trifluoromethyl)benzoic acid;
5-Bromo-N-(5-methyl-pyridin-2-yl)-phthalamic acid;
5-Bromo-N-(5-chloro-pyridin-2-yl)-phthalamic acid;
5-Bromo-N-pyridin-2-yl-phthalamic acid;
5-Bromo-N-(6-chloro-pyridin-2-yl)-phthalamic acid;
5-Bromo-N-(5,6-dimethyl-pyridin-2-yl)-phthalamic acid;
5-Bromo-N-(4-methyl-pyridin-2-yl)-phthalamic acid;
5-Bromo-N-(2-methyl-pyridin-4-yl)-phthalamic acid;
5-Bromo-N-pyridin-3-yl)-phthalamic acid;
5-Bromo-N-(3-methyl-pyridin-2-yl)-phthalamic acid;
5-Bromo-N-(4-methyl-thiazol-2-yl)-phthalamic acid;
5-Bromo-N-quinolin-2-yl-phthalamic acid;
5-Bromo-N-(5,6-dichloro-pyridin-2-yl)-phthalamic acid;
5-Bromo-N-(6-methyl-pyridin-3-yl)-phthalamic acid;
5-Bromo-N-(6-methyl-pyridazin-3-yl)-phthalamic acid;
5-Bromo-N-(4,6-dimethyl-pyridin-2-yl)-phthalamic acid;
5-Bromo-N-(2-methyl-pyrimidin-4-yl)-phthalamic acid;
5-Bromo-N-(6-methyl-pyrimidin-4-yl)-phthalamic acid;
N-(2-Methoxy-pyridin-4-yl)-5-trifluoromethyl-phthalamic acid;
N-(6-Methoxy-pyridin-2-yl)-5-trifluoromethyl-phthalamic acid;
N-Pyridin-2-ylmethyl-5-trifluoromethyl-phthalamic acid;
N-Pyridin-4-ylmethyl-5-trifluoromethyl-phthalamic acid;
N-Pyridin-3-ylmethyl-5-trifluoromethyl-phthalamic acid;
N-(6-Methyl-pyridin-2-yl)-5-propyl-phthalamic acid;
N 5-Isopropenyl-N-(6-methyl-pyridin-2-yl)-phthalamic acid;
N 5-Isopropyl-N-(6-methyl-pyridin-2-yl)-phthalamic acid;
2-(2-methylpyrimidin-4-yl)carbamoyl)-5-(trifluoromethyl)benzoic acid;
2-(4,5-dimethylpyrimidin-2-yl)carbamoyl)-5-(trifluoromethyl)benzoic acid;
2-(5,6,7,8-tetrahydroquinolin-2-yl)carbamoyl)-5-(trifluoromethyl)benzoic acid;
2-((6-methylpyridin-2-yl)carbamoyl)-4, 5-bis(trifluoromethyl)benzoic acid;
24(5,6,7,8-tetrahydroquinolin-2-yl)carbamoyl)-4,5-bis(trifluoromethyl)benzoic acid;
2-((5,6-dimethylpyridin-2-yl)carbamoyl)-4, 5-bis(trifluoromethyl)benzoic acid;
2-((2-methylpyrimidin-4-yl)carbamoyl)-4, 5-bis(trifluoromethyl)benzoic acid; and
2-((2, 6-dimethylpyridin-4-yl)carbamoyl)-5-(trifluoromethyl)benzoic acid;

or is a pharmaceutically acceptable salt or prodrug thereof.

5. A pharmaceutical composition comprising a compound according to claim 1 and one or more pharmaceutically acceptable carriers or diluents.

6. A pharmaceutical composition comprising a prodrug according to claim 1 and one or more pharmaceutically acceptable carriers or diluents.

7. The compound according to claim 4, wherein said compound is N-(6-Methyl-pyridin-2-yl)-5-trifluoromethyl-phthalamic acid or a pharmaceutically acceptable salt or prodrug thereof.

8. The pharmaceutical composition according to claim 5, wherein said compound is N-(6-Methyl-pyridin-2-yl)-5-trifluoromethyl-phthalamic acid or a pharmaceutically acceptable salt or prodrug thereof.

* * * * *

```
                    SEQUENCE LISTING

<160> NUMBER OF SEQ ID NOS: 1

<210> SEQ ID NO 1
<211> LENGTH: 13
<212> TYPE: PRT
<213> ORGANISM: Artificial Sequence
<220> FEATURE:
<223> OTHER INFORMATION: Scrambled Human Neurotensin

<400> SEQUENCE: 1

Leu Ile Tyr Pro Arg Asn Glu Tyr Glu Leu Arg Lys Pro
1               5                   10
```